United States Patent
Schalk et al.

(10) Patent No.: US 10,000,773 B2
(45) Date of Patent: Jun. 19, 2018

(54) CYTOCHROME P450 AND USE THEREOF FOR THE ENZYMATIC OXIDATION OF TERPENES

(71) Applicant: FIRMENICH SA, Geneva (CH)

(72) Inventors: Michel Schalk, Geneva (CH); Fabienne Deguerry, Geneva (CH)

(73) Assignee: FIRMENICH SA, Geneva (CH)

( * ) Notice: Subject to any disclaimer, the term of this patent is extended or adjusted under 35 U.S.C. 154(b) by 163 days.

(21) Appl. No.: 14/355,840

(22) PCT Filed: Oct. 25, 2012

(86) PCT No.: PCT/EP2012/071096
§ 371 (c)(1),
(2) Date: Aug. 18, 2014

(87) PCT Pub. No.: WO2013/064411
PCT Pub. Date: May 10, 2013

(65) Prior Publication Data
US 2015/0218588 A1    Aug. 6, 2015

(30) Foreign Application Priority Data
Nov. 1, 2011 (EP) .................... 11187409

(51) Int. Cl.
| C12P 5/00 | (2006.01) |
| C12N 9/02 | (2006.01) |
| C12P 7/02 | (2006.01) |
| C12P 7/24 | (2006.01) |
| C12P 7/40 | (2006.01) |

(52) U.S. Cl.
CPC ............ *C12P 5/007* (2013.01); *C12N 9/0071* (2013.01); *C12P 7/02* (2013.01); *C12P 7/24* (2013.01); *C12P 7/40* (2013.01)

(58) Field of Classification Search
CPC ..................................................... C12P 5/007
See application file for complete search history.

(56) References Cited

U.S. PATENT DOCUMENTS 8,163,980 B2    4/2012  Ro et al.
2007/0300327 A1  12/2007  Bouwmeester et al.

FOREIGN PATENT DOCUMENTS

| WO | WO2003025193 A1 | 3/2003 |
| WO | WO2006065126 A2 | 6/2006 |
| WO | WO2010134004 A1 | 11/2010 |
| WO | WO2011061656 A1 | 5/2011 |

OTHER PUBLICATIONS

Guo et al. 2004, PNAS 101(25) pp. 9205-9210.*
International Search Report and Written Opinion, application PCT/EP2012/071096, dated May 10, 2013.
Altschul et al. (1990) J. Mol. Biol. 215, 403-410.
Altschul, (J. Mol. Biol. 219- 555-65, 1991).
Barnes H.J (1996) Method Enzymol. 272, 3-14.
Daviet et al.—Flavor Frang J. 2010 25 123-127.
Halkier et al (1995) Arch. Biochem. Biophys. 322, 369-377.
Haudenschield et al (2000) Arch. Biochem. Biophys. 379, 127-136.
Jensen et al. (2010) Phytochemistry 71, 132-141.
Kolosova et al. Isolation of high-quality RNA from gymnosperm and angiosperm trees. J. Biotechniques, 36(5), 821-4, 2004.
Omura et al., 1964—Journal of biological chemistry 239 (2379-2385).
Rose et al. 1998. Nucleic Acids Research 26(7), 1628-1635).
Schoen et al., Plant cytoplasm localized yield increasing sequence SEQ13040—XP002692602.
Stemmer, Proc Natl Acad Sci U S A. 1994—91(22) 10747-1075.
Tatiana et al, FEMS Microbiol Lett., 1999, 174-247-250, 1999.
Thompson et al. (1994), Nucleic Acids Res. 22, 4673-4680.
Urban et al, 1997. Journal of biological chemistry 272 (19176-19186).
Bohmert, K., 2002, Plant Physiol., vol. 128, pp. 1282-1290.
Bertea, C. et al., Cytochrome P450 [Mentha x gracilis], GenBank Accession No. AAQ18707, Nov. 7, 2003.
Wang, E. et al., Cytochrome P450 [Nicotiana tabacum], GenBank Accession No. AAD47832, May 25, 2001.
Ralston, L. et al., Elicitor-inducible cytochrome P450 [Nicotiana tabacum], GenBank Accession No. AAK62343, Feb. 11, 2002.
Lupien, S. et al., Cytochrome p450 [Mentha spicata], GenBank Accession No. AAD44150, May 1, 2001.
Hutvagner,G. et al., RecName: Full=Cytochrome P450 71D6, GenBank Accession No. P93530, Nov. 26, 2014.
Bertea, C. et al., Limonene-3-hydroxylase [Mentha x gracilis], GenBank Accession No. AAQ18708, Nov. 7, 2003.
Lupien, S. et al., Cytochrome p450 isoform PM17 [Mentha x piperita], GenBank Accession No. AAD44151, May 1, 2001.
Paterson, A.H. et al., Hypothetical protein SORBI_001G235500 [Sorghum bicolor], GenBank Accession No. EER94164, Feb. 11, 2016.
Takahashi, S. et al., Cytochrome P450 hydroxylase [Hyoscyamus muticus], GenBank Accession No. ABS00393, Oct. 23, 2007.

(Continued)

*Primary Examiner* — Russell Kallis

(57) ABSTRACT

The present invention provides the nucleic acid and the amino acid sequences of a cytochrome P450 capable of oxidizing terpene molecules. It also provides a method of oxidizing terpene molecules comprising contacting the cytochrome P450 of the invention with the terpene molecule intended to be oxidized. In particular, said method may be carried out in vitro or in vivo to produce oxidized terpene molecules, which may be used in different technical fields such as for example perfumery and flavoring. The present invention also provides an expression vector containing the nucleic acid. A non-human host organism or a cell transformed with the nucleic acid is also an object of the invention.

23 Claims, 12 Drawing Sheets

(56) References Cited

OTHER PUBLICATIONS

Lupien, S. et al., Cytochrome p450 isoform PM2 [Mentha x piperita], GenBank Accession No. AAD44152, May 1, 2001.
Schneider, M., Cytochrome P450 [Solanum tuberosum], GenBank Accession No. CAC24711, Apr. 15, 2005.

* cited by examiner

Figure 3

VzP521-11:

```
                ....|....|....|....|....|....|....|....|....|....|....|....|
                         10        20        30        40        50        60
Wild-type (SEQ ID NO: 23)      MEDTKIIVAAVSVVCVIEVVLSKIKKSLLLPGAKPKLNLPPGPWTLPVIGSLHHVITYPNLQ
N-term modified (SEQ ID NO: 35) MALLLAVFWSALIILWVTYTISLLINQWRKPKQGKFPPGPWTLPVIGSLHHVITYPNLQ
```

VzP521-16:

```
                ....|....|....|....|....|....|....|....|....|....|....|....|
                         10        20        30        40        50        60
Wild-type (SEQ ID NO: 24)      MEDTKIIVAVVSVVCVVVLSKIKKSLLLGAKPKLNLPPGPWTLPVIGSLHHVITYPNLQ
N-term modified (SEQ ID NO: 36) MALLLAVFWSALIILWVTYTISLLINQWRKPKQGKFP

Figure 5

```
          End of P450                                    RBS                          Start of CPR
    I   A   P   A   G   F   N   *                                            M   G   T   D   S   L   S   D   D
CATTGCGCCGCCGGGTTTTAATTAAGCTGTCGACTAACTTTAAGAAGGAGATATATCCATGGGCACGGATAGCCTGAGCGACGAC    (SEQ ID NO: 54)
                                 SalI                 NcoI
GTAACGCGGCCGCCAAAATTAATTCGACAGCTGATTGAAATTCTTCCTCTATATAGGTACCCGTGCCTATCGGACTCGCTGCTG
```

Figure 6
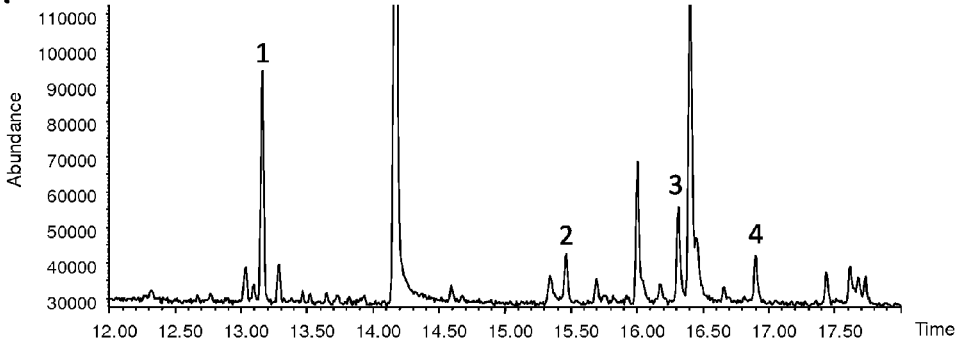
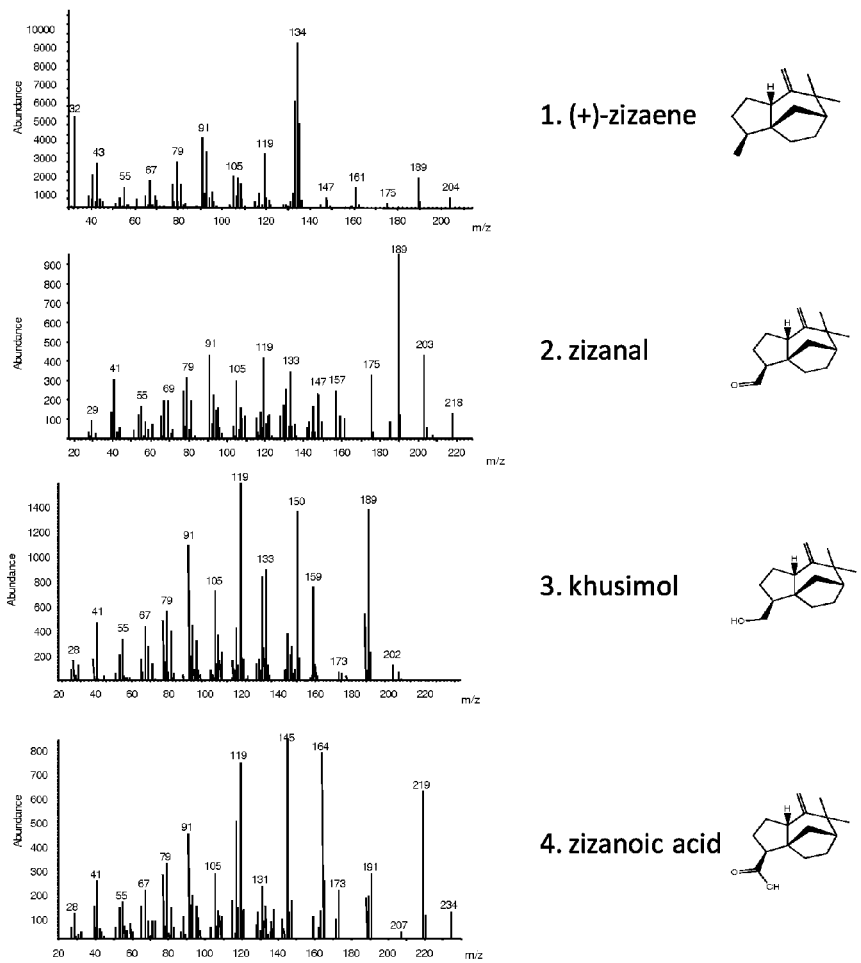
1. (+)-zizaene
2. zizanal
3. khusimol
4. zizanoic acid

US 10,000,773 B2

CYTOCHROME P450 AND USE THEREOF FOR THE ENZYMATIC OXIDATION OF TERPENES

TECHNICAL FIELD

The present invention provides the nucleic acid and the amino acid sequences of a cytochrome P450 capable of oxidizing terpene molecules. It also provides a method of oxidizing terpene molecules comprising contacting the cytochrome P450 of the invention with the terpene molecule intended to be oxidized. In particular, said method may be carried out in vitro or in vivo to produce oxidized terpene molecules, which may be used in different technical fields such as for example perfumery and flavoring. The present invention also provides an expression vector containing the nucleic acid. A non-human host organism or a cell transformed with the nucleic acid is also an object of the invention.

BACKGROUND OF THE INVENTION

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Diterpenes, for example, are widely found in the plant kingdom and over 2500 diterpene structures have been described (Connolly and Hill, Dictionary of terpenoids, 1991, Chapman & Hall, London). Terpene molecules and their oxidized derivatives have been of interest for thousands of years because of their flavor and fragrance properties and their cosmetic, medicinal and antimicrobial effects. Plant extracts obtained by different means such as steam distillation or solvent extraction are used as source of oxidized derivatives of terpene molecules. Alternatively, terpene molecules found in plant extracts or obtained by biosynthetic processes are oxidized using chemical and enzymatic processes.

Enzymatic oxidation of terpenes often involves enzymes called cytochrome P450s (P450s), which are typically capable of catalyzing the transformation of a hydrophobic substrate, such as a terpene molecule, in a more hydrophilic one. Cytochrome P450 enzymes form a superfamily of hemoproteins found in bacteria, archaea and eukaryotes. In one of the most common activities, cytochrome P450 acts as a monooxygenase, by inserting one oxygen atom of molecular oxygen into a substrate molecule, while the other oxygen atom is reduced to water.

This catalytic reaction requires two electrons for the activation of molecular oxygen. P450s from eukaryotes use NADPH as the external reductant and source of electrons. The two electrons are transferred one at a time to the cytochrome P450 active site and this transfer requires an electron donor protein, a cytochrome P450 reductase (CPR). One CPR is not specific for one cytochrome P450. A CPR is the electron donor protein for several P450s in a given organism. In addition, a CPR from one organism can act as the electron donor protein for P450s from other organisms. In some cases P450s can also be coupled to a cytochrome b5 protein that can act as the electron donor protein or can improve the efficiency of the electron transfer from the CPR to the P450. In eukaryotic cells and particularly in plants, P450s and CPRs are generally membrane-bound proteins and are associated with the endoplasmic reticulum. These proteins are anchored to the membrane by a N-terminal trans-membrane helix.

Many P450s have low substrate specificity and are therefore able to catalyze the oxidation of many diverse structures such as for example different terpene molecules. Most of these enzymes have a particular regio- and stereo-selectivity with a given substrate but they often produce a mixture of several products from a particular substrate. Such P450s are usually involved in the breakdown and detoxification of molecules such as xenobiotics and are generally found in bacteria and animals. On the other hand, P450s involved in biosynthetic pathways show usually a specificity for certain types of substrates and regio- and stereo-selectivity. This is the case for most plant P450s.

A large number of P450s can be found in nature and particularly in plants. One plant genome can contain several hundreds of genes encoding for P450s. Many plant P450s have been characterized but considering the extremely large number of P450s present in plants, most of their functions remain unknown.

It is therefore desirable to search for new P450s capable of catalyzing new enzymatic reactions, so as to provide enzymatic production of new oxygenated compounds or for producing oxygenated compounds through different reaction types, for example from different substrates, which may be more easily accessible.

Several P450s have already been characterized. In particular, cytochromes P450 having a certain percentage of sequence identity with the cytochrome P450 of the present invention have been reported to use terpene molecules as substrates.

The closest P450s to that of the present invention are P450s from *Sorghum bicolor*, among which the closest sequence shares 67% identity with the amino acid sequences described herein (Accession number EER94164).

Among the oxygenated terpenes produced by the cytochrome P450 of the present invention, some are very useful in the field of perfumery and flavoring. In particular khusimol, which is produced by hydroxylation of zizaene, is one of the key components of vetiver oil and is in itself a valuable perfuming ingredient. Oxidation of zizaene using the cytochrome P450 of the present invention provides an advantageous alternative to isolation of khusimol from vetiver oil, which is a difficult and expensive process. To the best of our knowledge, no enzymatic process for the production of khusimol is known. Several other valuable perfuming and flavouring ingredients, for which no enzymatic synthesis is known to date, can be prepared using the cytochrome P450 of the present invention as will be described below.

Other oxygenated terpenes produced by the cytochrome P450 of the present invention are useful for other purposes such as drugs or agrochemical products. The cytochrome P450 of the present invention therefore opens a new biosynthetic route to diverse molecules having interesting properties useful in various fields of the industry and being difficult or even impossible to isolate from nature and difficult or impossible to produce by organic synthesis.

It is an objective of the present invention to provide methods for making oxygenated terpenes, in particular khusimol, in an economic way. Accordingly, the present invention has the objective to produce oxygenated terpenes while having little waste, a more energy and resource efficient process and while reducing dependency on fossil fuels. It is a further objective to provide enzymes capable of oxidizing terpene molecules, such oxidized products being useful as perfumery and/or aroma ingredients.

ABBREVIATIONS USED bp base pair
DMAPP dimethylallyl diphosphate
DNA deoxyribonucleic acid
cDNA complementary DNA
CPR cytochrome P450-reductase
dNTP deoxy nucleotide triphosphate
DTT dithiothreitol
EDTA ethylenediaminetetraacetic acid
FAD flavine adenosine dinucleotide
FMN flavine mononucleotide
FPP farnesyl pyrophosphate
GC gaseous chromatograph
IPP isopentenyl diphosphate
IPTG isopropyl-D-thiogalacto-pyranoside
LB lysogeny broth
MS mass spectrometer
mvaK1 mevalonate kinase
mvaK2 mevalonate diphosphate kinase
NADP nicotinamide adenine dinucleotide phosphate
NADPH nicotinamide adenine dinucleotide phosphate, reduced form
P450 cytochrome P450
PCR polymerase chain reaction
3'-/5'-RACE 3' and 5' rapid amplification of cDNA ends
RMCE recombinase-mediated cassette exchange
RT-PCR reverse transcription-polymerase chain reaction
RNA ribonucleic acid
mRNA messenger ribonucleic acid
RBS Ribosome binding site.

DESCRIPTION OF THE INVENTION

The present invention provides a method to enzymatically oxidize terpenes in an economic, reliable and reproducible way.

As intended in the present application, all compounds cited in the present application are defined by the way of their formula as represented in FIG. 1.

A "cytochrome P450" or a "polypeptide having a cytochrome P450 activity" is intended for the purpose of the present application as a polypeptide capable of catalyzing the oxydation of a terpene molecule to form an oxygenated compound such as an alcohol, an aldehyde, a ketone or a carboxylic acid. According to a preferred embodiment, the cytochrome P450 acts as a mono-oxygenase by adding only one oxygen atom to a terpene compound. The ability of a polypeptide to catalyze the oxidation of a particular terpene can be simply confirmed by performing the enzyme assay as detailed in Example 8.

According to the present invention, "polypeptides" are also meant to include truncated polypeptides provided that they keep their cytochrome P450 activity as defined in any of the embodiments of the invention and that they share at least the defined percentage of identity with the corresponding fragment of SEQ ID NO:1 or 2.

The percentage of identity between two peptidic or nucleotidic sequences is a function of the number of amino acids or nucleic acids residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs available on the world wide web. Preferably, the BLAST program (Tatiana et al, FEMS Microbiol Lett., 1999, 174:247-250, 1999) set to the default parameters, available from the National Center for Biotechnology Information (NCBI) at http://www.ncbi.nlm nih gov/BLAST/b12seq/wblast2.cgi, can be used to obtain an optimal alignment of peptidic or nucleotidic sequences and to calculate the percentage of sequence identity.

One object of the present invention is a polypeptide comprising an amino acid sequence at least 70% identical to SEQ ID NO:1 or 2 and having a cytochrome P450 activity.

In a preferred embodiment the polypeptide having a cytochrome P450 activity is intended as a polypeptide capable of catalyzing the oxidation of at least one terpene compound selected from mono- or polycyclic monoterpenes and sesquiterpenes. In a preferred embodiment, said sesquiterpene or monoterpene comprises at least one methyl group as substituent on a cyclic moiety. According to a more preferred embodiment, the cytochrome P450 of the invention oxidizes said methyl substituent to provide a primary alcohol.

According to a preferred embodiment, the terpene compound is selected from the group consisting of zizaene, alpha-cedrene, alpha-longipinene, alpha-funebrene, thujopsene, valencene, beta-chamigrene, alloaromadendrene, alpha-neoclovenene, isosativene, ledene, s-limonene, alpha-humulene, alpha-gurjunene, alpha-pinene, beta-funebrene, R-limonene and beta-pinene. More preferably said terpene compound is selected from zizaene, alpha-cedrene, alpha-funebrene, valencene and thujopsene Most preferably, said terpene compound is zizaene.

In a preferred embodiment, one oxygen atom is added to the methyl group so as to provide a primary alcohol, an aldehyde and/or a carboxylic acid. In a most preferred embodiment, zizaene is oxidized to khusimol, zizanal and/or zizanoic acid.

In the case where an aldehyde and/or a carboxylic acid is formed, said aldehyde and/or a carboxylic acid is formed by further oxidation of the primary alcohol either by the P450 of the invention by one or more enzymes from other families such as for example alcohol dehydrogenases, aldehyde reductases, aldehyde oxidases. The latter enzymes are for example present in any host organism or cell in which the polypeptide of the invention can be expressed.

According to a preferred embodiment, the polypeptide comprises an amino acid sequence at least 75%, preferably at least 80%, preferably at least 85%, preferably at least 89%, preferably at least 90%, more preferably at least 95% and even more preferably at least 98% identical to SEQ ID NO:1 or 2. According to a more preferred embodiment, the polypeptide comprises SEQ ID NO:1 or 2. Even more preferably it consists of SEQ ID NO:1 and 2.

In a preferred embodiment of the invention the sequence also comprises a membrane anchor sequence. The sequence represented by SEQ ID NO:1 or 2, or the derivative thereof having the required percentage of identity is the part of the polypeptide that provides the P450 activity. The membrane anchor sequence is not involved in the catalytic activity of the enzyme. The anchor sequence enables binding to the membrane. Suitable anchor sequences depend from the organism in which the polypeptide is expressed and sequences designed for common types of host organisms are known to the person skilled in the art. Any suitable anchor sequence can be used in combination with the polypeptide of the present invention. Therefore, according to one preferred embodiment, the polypeptide comprises SEQ ID NO:1 or 2, combined with a membrane anchor sequence.

More preferably, the polypeptide of the invention consists of SEQ ID NO:1 or 2, optionally combined with a membrane anchor sequence.

When the polypeptide is not combined with an anchor sequence, such polypeptide will not bind to the cell membrane. In this case, the polypeptide of SEQ ID NO:1 or 2 can preferably be modified in order to improve its solubility in the cytoplasm.

According to another preferred embodiment, the polypeptide comprises an amino acid sequence that is a variant of SEQ ID NO:1 or 2 obtained by genetic engineering. In other terms, said polypeptide comprises an amino acid sequence encoded by a nucleotide sequence that has been obtained by modifying SEQ ID NO:3, 4 or the complement thereof. According to a more preferred embodiment, the polypeptide having a cytochrome P450 activity consists of an amino acid sequence that is a variant of SEQ ID NO:1 or 2 obtained by genetic engineering, i.e. an amino acid sequence encoded by a nucleotide sequence that has been obtained by modifying any one of SEQ ID NO:3, 4 or the complement thereof.

Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends are also encompassed by the polypeptides of the invention. In particular such a fusion can enhance expression of the polypeptides, be useful in the purification of the protein, improve the way the polypeptide can be anchored to a membrane or improve the enzymatic activity of the polypeptide in a desired environment or expression system. Such additional peptide sequences may be a signal peptide, for example. Accordingly, the present invention encompasses variants of the polypeptides of the invention, such as those obtained by fusion with other oligo- or polypeptides and/or those which are linked to signal peptides. Polypeptides resulting from a fusion with another functional protein, such as a protein from the terpene biosynthesis pathway, preferably a terpene synthase, are also encompassed by the polypeptides of the invention. One particularly preferred example of polypeptide of the invention being a variant resulting from fusion with a peptide sequence is a fusion polypeptide comprising both a polypeptide of the invention (having a cytochrome P450 activity) and a CPR.

According to another embodiment, the polypeptide is isolated form *Vetiveria zizanioides* (L.) Nash.

A nucleic acid encoding a polypeptide according to any of the above-described embodiments is also an object of the present invention.

According to a preferred embodiment, the nucleic acid comprises a nucleotide sequence at least 70%, preferably at least 75%, preferably at least 80%, preferably at least 85%, preferably at least 90%, preferably at least 93%, more preferably at least 95% and even more preferably at least 98% identical to SEQ ID NO:3, 4 or the complement thereof. According to a more preferred embodiment, the nucleic acid comprises SEQ ID NO:3, 4 or the complement thereof. According to an even more preferred embodiment, the nucleic acid consists of SEQ ID NO:3, 4 or the complement thereof, optionally together with a nucleotide sequence encoding a membrane anchor sequence.

According to another embodiment, the nucleic acid is isolated from *Vetiveria zizanioides* (L.) Nash.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

According to a more preferred embodiment, the at least one nucleic acid according to any of the above embodiments comprises a nucleotide sequence that has been obtained by modifying SEQ ID NO:3, 4 or the complement thereof. Preferably said nucleic acid consists of a nucleotide sequence that has been obtained by modifying SEQ ID NO:3, 4 or the complement thereof.

The nucleic acids comprising a sequence obtained by mutation of SEQ ID NO:3, 4 or the complement thereof are encompassed by the invention, provided that the sequences they comprise share at least the defined percentage of identity with the corresponding fragments of SEQ ID NO:3, 4 or the complement thereof and provided that they encode a polypeptide having a cytochrome P450 activity, as defined in any of the above embodiments. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

The present invention also provides a method for oxidizing at least one terpene compound comprising a) contacting said terpene compound with at least one polypeptide of the invention in the presence of a cytochrome P450 reductase (CPR);

b) optionally, isolating the oxidized terpene produced in step a).

The terpene compound oxidized by the polypeptide of the invention and the polypeptide of the invention itself are as defined in any of the embodiments described above.

The method can be carried out in vitro as well as in vivo, as will be explained in details further on.

When the method is carried out in vitro, the polypeptide of the invention to be contacted with the terpene compound and the CPR can be obtained by extraction from any organism expressing it, using standard protein or enzyme extraction technologies. If the host organism is an unicellular organism or cell releasing the polypeptide of the invention into the culture medium, for example when no membrane anchor is present, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate. When P450s and CPRs comprise a membrane anchor sequence, such as natural P450s and CPRs in plants, they are associated with membranes and are therefore located in the membrane fraction of cells lysates. The membrane fraction (microsoms) can be easily separated from the other protein fractions by differential centrifugations of the crude cell lysate using known methods.

For the in vitro method the polypeptide of the invention and the CPR can independently be provided in isolated form or as part of a protein extract and is suspended in a buffer solution at optimal pH. If adequate, salts, DTT, NADPH, NADH, FAD, FMN and other kinds of enzymatic co-factors, may be added in order to optimize enzyme activity. Appropriate conditions are described in more details in the Examples further on.

The terpene compound is then added to the suspension or solution, which is then incubated at optimal temperature, for example between 15 and 40° C., preferably between 25 and 35° C., more preferably at 30° C. After incubation, the oxidized terpene produced may be isolated from the incubated solution by standard isolation procedures, such as solvent extraction and distillation, optionally after removal of polypeptides from the solution.

The CPR must be present while the P450 and the terpene compound are in contact.

According to another preferred embodiment, the method for oxidizing terpene compounds is carried out in vivo. In this case, step a) of the above-described method comprises cultivating a non-human host organism or cell transformed to express at least one polypeptide of the invention in the presence of a terpene compound to be oxidized under conditions conducive to the oxidation of the terpene compound, said organism or cell further expressing a CPR.

The terpene compound and the polypeptide are as defined in any embodiment of the present invention.

In one embodiment of such process, the terpene compound to be oxidized is produced by the host organism or cell expressing the polypeptide of the invention. In this case, the terpene compound is produced in the host organism or cell by a terpene synthase capable of catalyzing the formation of said terpene compound from an acyclic terpene precursor. Said terpene synthase can either be produced naturally by the host organism or cell, or where the host organism or cell does not express such terpene synthase naturally, it can be transformed to do so.

In an alternative embodiment, in the case where a host cell is used or when the host organism is a microorganism, the terpene compound to be oxidized can be added to the culture medium of said cell or microorganism. The terpene compound will permeate through the membrane of the cell or microorganism, thus being available for reaction with the polypeptide of the invention expressed by said host cell or microorganism.

According to a more preferred embodiment, the method further comprises, prior to step a), transforming a non human organism or cell with at least one nucleic acid of the invention, so that said organism or cell expresses at least one polypeptide of the invention. The polypeptide and the nucleic acid are as defined in any of the embodiments described above.

Carrying out the method in vivo is particularly advantageous since it is possible to carry out the method without previously isolating the polypeptide. The reaction occurs directly within the organism or cell transformed to express the polypeptide.

For catalytic activity, P450s must be used in combination with a P450-reductase (CPR) which is capable of transferring electrons from NADPH (Nicotinamide adenine dinucleotide phosphate, reduced form) to the P450 active site, so as to reconstitute the P450 activity. The CPR must be present both for carrying out the process in vitro and in vivo. When the method is carried out in vivo, the CPR can either be present naturally in the host organism or cell, or such organism or cell can be transformed to express a CPR prior to, simultaneously with or after transformation to express the polypeptide of the invention. In a preferred embodiment of the invention the host cell or organism is transformed with a fusion polypeptide comprising both the polypeptide of the invention and the CPR.

In another preferred embodiment the CPR is a plant CPR. Most preferably it is derived from an *Arabidopsis thaliana* CPR.

The non-human organism or cell can advantageously be further transformed with at least one gene encoding a polypeptide involved in the metabolism of production of acyclic terpene precursors such as geranyl pyrophosphate, farnesyl pyrophosphate or geranylgeranyl pyrophosphate. Such polypeptides include for example enzymes of the MEP pathway, of the MVA pathway and/or prenyl transferases.

Transforming a non-human organism or cell with a polypeptide having a cytochrome P450 activity and with a CPR, or with a fusion polypeptide comprising both, in the presence of a terpene compound to be oxidized, as described in any of the embodiments of the invention, is sufficient for the oxidation of the terpene to take place. Nevertheless, further transformation with at least one enzyme involved in the production of an acyclic terpene precursor and/or of isopentenyl diphosphate (IPP) or dimethylallyl diphosphate (DMAPP), has the advantage of increasing the amount of terpene compound available to be oxidized.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects of the present invention and in the Examples.

Methods to transform organisms, for example microorganisms, so that they express a terpene synthase are already known in the art. Such methods can for example be found in WO 2010/134004, which describes transformation of diverse host organisms and cells with a zizaene synthase, i.e. an enzyme capable of catalyzing the production of zizaene from farnesyl pyrophosphate.

To carry out the invention in vivo, the host organism or cell is cultivated under conditions conducive to the production of the oxidized terpene. Such conditions are any conditions leading to growth of the host organism or cell. Preferably, such conditions are designed for optimal growth of the host organism or cell. Accordingly, if the host is a transgenic plant, optimal growth conditions are provided, such as optimal light, water and nutrient conditions, for example. If the host is a unicellular organism, conditions conducive to the production of the oxidized terpene may comprise addition of suitable cofactors to the culture medium of the host. In addition, a culture medium may be selected, so as to maximize terpene oxidation. Optimal culture conditions are known to the person skilled in the art and are not specific to the present invention. Examples of suitable conditions are described in a more detailed manner in the following Examples.

Non-human host organisms suitable to carry out the method of the invention in vivo may be any non-human multicellular or unicellular organisms. In a preferred embodiment, the non-human host organism used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism used to carry out the method of the invention in vivo is a microorganism. Any microorganism can be used but according to an even more preferred embodiment said microorganism is a bacteria or fungus. Preferably said fungus is yeast. Most preferably, said bacteria is *E. coli* and said yeast is *Saccharomyces cerevisiae*.

Several of these organisms do not produce the terpene to be oxidized naturally. To be suitable to carry out the method of the invention, these organisms have to be transformed to produce said terpene. They can be so transformed either prior to, simultaneously with or after transformation with the nucleic acid described according to any of the above embodiments, as explained above.

Isolated higher eukaryotic cells can also be used, instead of complete organisms, as hosts to carry out the method of the invention in vivo. Suitable eukaryotic cells may be any non-human cell, but are preferably plant cells.

An important tool for transforming host organisms or cells suitable to carry out the method of the invention in vivo is an expression vector comprising a nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for producing or making polypeptides of the invention, as disclosed further below.

Recombinant non-human host organisms and cells transformed to harbor at least one nucleic acid according to any embodiment of the present invention are also very useful tools to carry out the method of the invention. Such non-human host organisms and cells are therefore another object of the present invention. In a preferred embodiment, such host organism or cell heterologously expresses or over-expresses a polypeptide according to any embodiment of the present invention.

According to a preferred embodiment, the non-human host organism or cell further expresses a P450-reductase (CPR), as described above. The CPR can either be present naturally in the host organism or cell or such organism or cell can be transformed to express a CPR prior to, simultaneously with or after transformation to express the polypeptide of the invention. In a preferred embodiment of the invention the host cell or organism is transformed to express a fusion polypeptide comprising both the polypeptide of the invention and the CPR.

In another preferred embodiment, the organism or cell is capable of producing the terpene to be oxidized. This is the case when the organism or cell expresses a terpene synthase capable of catalyzing the formation of said terpene. In the case where the host organism or cell does not express such terpene synthase naturally, it can be transformed prior to, simultaneously with or after transformation with the polypeptide having a P450 activity.

The non-human organism or cell can advantageously be further transformed with at least one gene encoding a polypeptide involved in the metabolism of production of acyclic terpene precursor such as geranyl pyrophosphate, farnesyl pyrophosphate or geranylgeranyl pyrophosphate. Such polypeptides include for example enzymes of the MEP pathway, of the MVA pathway and/or prenyl transferases. Transforming a non-human organism or cell capable of producing a terpene compound with a polypeptide of the invention and with a CPR, or with a fusion polypeptide comprising both, as described in any of the embodiments of the invention, is sufficient for the oxidation of the terpene to take place. Nevertheless, further transformation with at least one enzyme involved in the production of an acyclic terpene precursor and/or of isopentenyl diphosphate (IPP) or dimethylallyl diphosphate (DMAPP), has the advantage of increasing the amount of terpene available to be oxidized.

Types of non-human host organisms and cells of the invention are as described in any embodiment of the method for oxidizing a terpene compound.

The term "transformed" refers to the fact that the host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., Cloning Vectors: A Laboratory Manual, 1985, Elsevier, New York and Sambrook et al., Molecular Cloning: A Laboratory Manual, 2$^{nd}$ edition, 1989, Cold Spring Harbor Laboratory Press. Cloning and expression vectors for higher plants and/or plant cells in particular are available to the skilled person. See for example Schardl et al. Gene 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

In order to carry out the method for oxidizing a terpene compound in vitro, as described herein above, it is very advantageous to provide a method of making a polypeptide of the invention. Therefore, the invention provides a method for producing a polypeptide of the present invention comprising a) culturing a non-human host organism or cell transformed to harbor at least one nucleic acid according to the invention and expresses or over-expresses at least one polypeptide of the invention;

b) isolating the polypeptide of the invention from the non-human host organism or cell cultured in step a).

According to a preferred embodiment, said method further comprises, prior to step a), transforming a non-human host organism or cell with at least one nucleic acid according to the invention so that it expresses or over-expresses a polypeptide according to the invention.

Transformation and culture of the non-human host organism or cell can be carried out as described above for the method of producing an oxidized terpene in vivo. Step b) may be performed using any technique well known in the art to isolate a particular polypeptide from an organism or cell.

A "polypeptide variant" as referred to herein means a polypeptide capable of catalyzing the oxidation of a terpene compound of Formula (I) and having a sufficient percentage of sequence identity according to any of the above embodiments. Such variant polypeptides are encoded by nucleotidic sequences that have undergone one or more deletions, insertions or substitutions.

Variants can comprise conservatively substituted sequences, meaning that a given amino acid residue is replaced by a residue having similar physicochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65, 1991). Other such conservative substitutions, for example substitutions of entire regions having similar hydrophobicity characteristics, are well known. The polypeptides of the invention can also be subjected to non conservative substitutions, so as to generate more diverse variants, provided that such variants retain the desired cytochrome P450 activity. Variants can also be produced by deletion and insertion of nucleotide(s) into the nucleic acid sequence encoding for the variant polypeptide.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, or by artificially programming mutations of nucleotide sequences coding for the polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides.

Therefore, in an embodiment, the present invention provides a method for preparing a variant polypeptide capable of catalyzing the oxidation of a terpene compound and comprising the steps of:

(a) selecting a nucleic acid according to any of the embodiments exposed above;

(b) modifying the selected nucleic acid to obtain at least one mutant nucleic acid;

(c) transforming host cells or unicellular organisms with the mutant nucleic acid sequence to express a polypeptide encoded by the mutant nucleic acid sequence;

(d) screening the polypeptide for at least one modified cytochrome P450 activity; and, (e) optionally, if the polypeptide has no desired variant cytochrome P450 activity, repeat the process steps (a) to (d) until a polypeptide with a desired variant cytochrome P450 activity is obtained;

(f) optionally, if a polypeptide having a desired variant cytochrome P450 activity was identified in step d), isolating the corresponding mutant nucleic acid obtained in step (c).

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. Proc Natl Acad Sci USA., 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, a nucleic acid encoding the polypeptide comprising SEQ ID NO:3, 4 or the complement thereof may be recombined with any other nucleic acid encoding a cytochrome P450, for example isolated from an organism other than Vetiveria zizanioides (L.) Nash. Thus, mutant nucleic acids may be obtained and separated, which may be used for transforming a host cell according to standard procedures, for example such as disclosed in the present Examples.

In step (d), the polypeptide obtained in step (c) is screened for at least one modified cytochrome P450 activity. Examples of desired modified cytochrome P450 activity, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present Examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

All the publications mentioned in this application are incorporated by reference to disclose and describe the methods and/or materials in connection with which the publications are cited.

DESCRIPTION OF THE DRAWINGS

FIG. 3: N-terminal (membrane anchor) modifications introduced in the two vetiver P450s for an improved heterologous expression in E. coli.

FIG. 5: Sequence of the spacer region between the P450 and CPR in the bi-cistronic constructs. The DNA and amino acid sequences at the end of the P450 and at the beginning of the CPR are shown.

FIG. 6: GCMS analysis of bioconversion of (+)-zizaene with E. coli expressing the vetiver P450 VzP521-16 and a CPR from arabisdopsis (tcATR1). A. Total ion chromatogram. B. Mass spectra of the substrate (1) and products (2 to 4) with the identity and structure of the corresponding compounds.

SPECIFIC EMBODIMENTS OF THE INVENTION OR EXAMPLES

The invention will now be described in further detail by way of the following Examples.

Example 1

RNA Extraction and cDNA Library Construction

Vetiver (Vetiveria zizanioides (L.) Nash) plants were obtained from a plant nursery (The Austral Plants Company, Les Avirons, The Reunion Island, France). The plants were cultivated in pots in a green house (Lullier Agronomy research Station, Geneva, Switzerland) and were propagated vegetatively by dividing six months to one-year-old clumps. For harvesting of the roots, the plants were removed from the pots and rinsed with tap water.

For extraction of RNA, roots from several plants were combined: young plants (4 to 6 months after propagation), old plants with a well-developed dense root system (1 to 2 years after propagation) and young plants dried at room temperature for 24 to 36 hours after being removed from the pots. The roots were cut off from the aerial part of the plants and frozen in liquid nitrogen. The roots were first roughly chopped in liquid nitrogen using a Waring Blendor (Waring Laboratory, Torrington, USA) and then ground to a fine powder using a mortar and pestle. Total RNA was extracted following the procedure described in Kolosova et al (Kolosova N, Miller B, Ralph S, Ellis B E, Douglas C, Ritland K, and Bohlmann J, Isolation of high-quality RNA from gymnosperm and angiosperm trees. J. Biotechniques, 36(5), 821-4, 2004) with the following modifications. A volume of 20 ml of extraction buffer was used for 2 grams of ground tissue and the extraction buffer was supplemented with 2% (w/v) of PVP (polyvinylpyrrolidone, Sigma-Aldrich). For the CTAB (cethyltrimethylammonium bromide, Sigma-Aldrich) extraction, the nucleic acid pellet was resuspended in 2 ml TE buffer (10 mM Tris-HCl, pH 8, 1 mM EDTA) and the extraction was performed with 2 ml of 5M NaCl and 1 ml 10% CTAB. For the isopropanol precipitation, the nucleic acid pellet was dissolved in 500 µl TE. The final RNA pellet was resuspended in 50 µl water.

The adaptor-ligated double stranded cDNA library was prepared from 1 µg of mRNA using the Marathon™ cDNA Amplification Kit (Clontech, Takara Bio Europe) following the manufacturer's protocol.

Example 2

Design of P450-Specific Oligonucleotides

Figure 2:
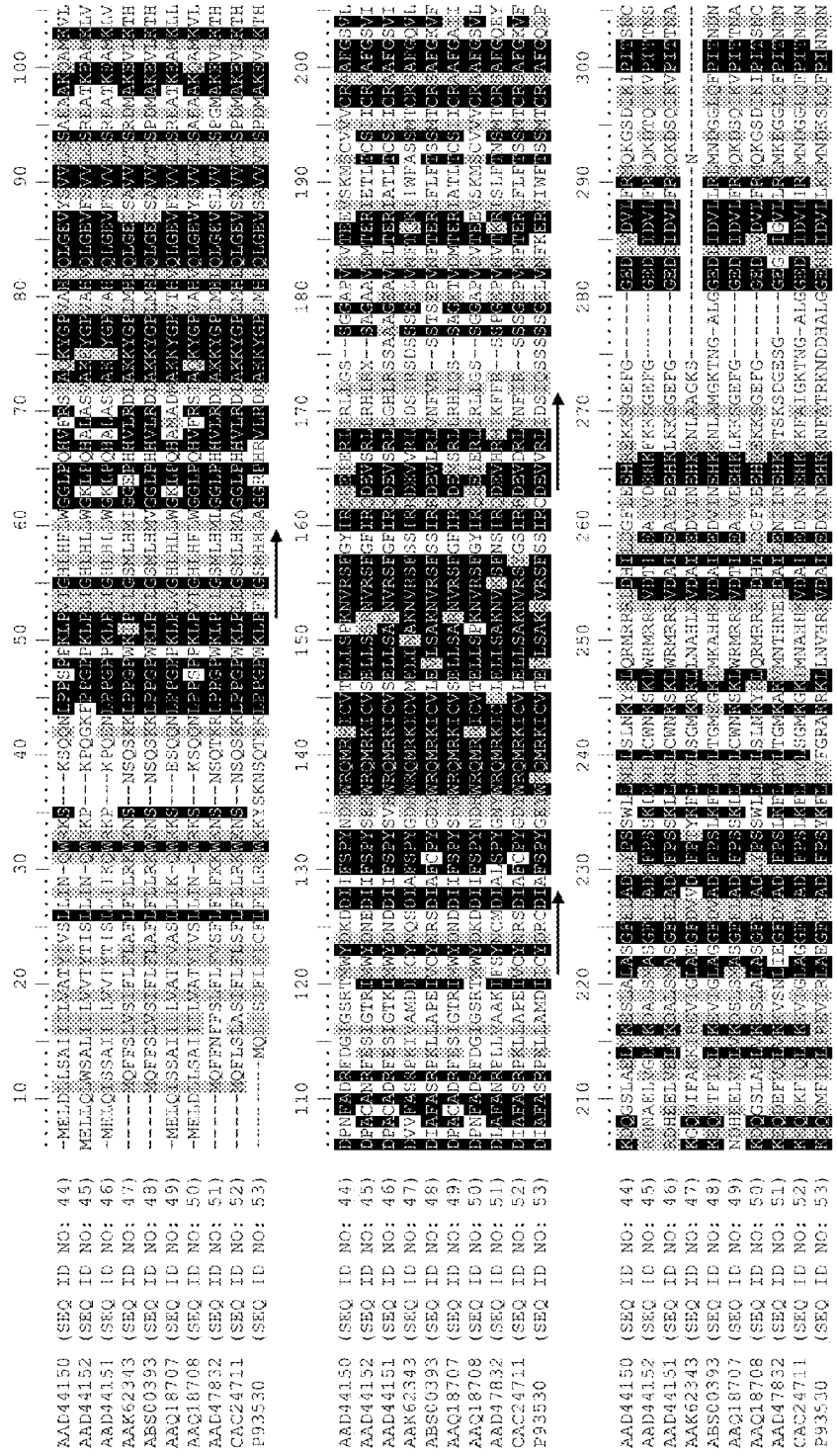
FIG. 2: Alignment of the amino acid sequences of selected P450 monooxygenases with defined terpene hydroxylase activity (prior art). The conserved regions found in all P450 enzymes are underlined. The six regions used to design the terpene-hydroxylase-specific oligonucleotides are underlined with arrows. The direction of the arrows indicates the orientation of the oligonucleotides.
Figure 2:

To design oligonucleotides specific for plant P450s with terpene hydroxylase activity, amino acid sequences from known terpene hydroxylating P450s were selected: a limonene 6-hydroxylase from spearmint (GenBank access No. AAD44150 SEQ ID NO: 44), two limonene 3-hydroxylases from peppermint (GenBank access No. AAD44152 SEQ ID NO: 45) and AAD44151 SEQ ID NO: 46), an epi-aristolochene hydroxylase from tobacco (Genbank access. No. AAK62343 SEQ ID NO: 47), a premnaspirodiene hydroxylase from *Hyoscyamus muticus* (GenBank access No. ABS00393 SEQ ID NO: 48), two limonene hydroxylases from scotch spearmint (Genbank access. No. AAQ18707 SEQ ID NO: 49 and AAQ18708 SEQ ID NO: 50), a diterpene hydroxylase from tobacco (Genbank access. No. AAD47832 SEQ ID NO: 51) and two members from the CYP71D family, Cyp71D4 from potato (Genbank access. No. CAC24711 SEQ ID NO: 52) and CYP71D6 from chaco potato (Genbank access. No. P93530 SEQ ID NO: 53). The sequences were aligned with the ClustalW program (Thompson, J. D., Higgins, D. G. and Gibson, T. J. (1994); CLUSTAL W: improving the sensitivity of progressive multiple sequence alignment through sequence weighting, position specific gap penalties and weight matrix choice; Nucleic Acids Res. 22, 4673-4680). The alignment is presented in FIG. 2.

In order to design oligonucleotides to be used for PCR amplifications of fragments of homologous P450 cDNAs, conserved regions were selected in this alignment. Parameters such as conservation of amino acids across all sequences and presence of amino acids with low codon degeneracy were considered in the selection of these regions. In addition, because plant genomes contain a large number of P450s involved in many different metabolism, regions related to functions common to all P450s were deliberately avoided. Those regions include for instance the heme-binding domain flanking the perfectly conserved cystein residue which covalently binds the heme-iron via its thiolate side chain (PFGxGRRICPG motif in our alignment SEQ ID NO: 41), the so called 'meander' (FxPERF motif in our alignment SEQ ID NO: 42) presumably involved in the interaction with the redox-partner protein and in the stabilization of heme-protein association, and the I helix region located in the active site on the distal side of the heme ((A/G)GTETSS motif SEQ ID NO: 43) and involved in proton transfer and oxygen activation. Six conserved regions putatively characteristic of plant terpene monooxygenases were thus selected (underlined with arrows in FIG. 1).

Hybrid primers containing a 3' degenerated core and a 5' consensus clamp were designed from these regions following the Consensus-Degenerated Hybrid Oligonucleotide Primers (CODEHOP) strategy (Rose T. M., Schultz E. R., Henikoff J. G, Pietrokovski S., McCallum C. M., and Nenikoff S.; 1998; Consensus-degenerated hybrid oligonucleotide primers for amplification of distantly related sequences; Nucleic Acids Research 26(7), 1628-1635) and using the online interface of the computer program available at http://blocks.fhcrc.org/blocks/codehop.html. Oligonucleotides were designed to have a degenerated core of 11 to 15 bases with a maximum degeneracy of 192 and an annealing temperature between 60 and 64° C. Using this approach, three sense primers (P450-Terp-F1 to F3 (SEQ ID NO:5 to 7)) and four anti-sense primers (P450-Terp-R1 to R4 (SEQ ID NO:8 to 11) were designed from the six conserved regions shown in FIG. 1 (Table 1).

TABLE 1

Terpene-hydroxylase-specific oligonucleotides. The sequence of the degenerated core of each primer is indicated in lower case and the consensus clamp is indicated in upper case. The nucleotide sequences are indicated from the 5' to the 3' end for the forward primers and from the 3' to the 5' end for the reverse primers. The degeneracy in the nucleotides sequences is indicated using the IUPAC one letter code.

| Primer name | Nucleotide sequence and correspond consensus amino acid sequence. |
|---|---|
| P450-terp-F1 (SEQ ID NO: 5) | GPVMHVQLGE (SEQ ID NO: 55)<br>5'-GGCCCGGTGATGCACGTGcarytnggnga-3' |
| P450-terp-F2 (SEQ ID NO: 6) | PYGDHWRQMR (SEQ ID NO: 56)<br>5'-CCGTACAGCGACCACTGGmrncaratgmg-3' |
| P450-terp-F3 (SEQ ID NO: 7) | SMTCRAAFG (SEQ ID NO: 57)<br>5'-GCTCCATGACCTGCCGGdsngcnttygg-3' |
| P450-terp-R1 (SEQ ID NO: 8) | VIKETMRMH (SEQ ID NO: 58)<br>3'-cannanttyctCTGGTACGCCTACGT-5' |
| P450-terp-R2 (SEQ ID NO: 9) | ETMRMHPP (SEQ ID NO: 59)<br>3'-ctytgndankcCTACGTGGGCGGC-5' |
| P450-terp-R3 (SEQ ID NO: 10) | FGLANVYLP (SEQ ID NO: 60)<br>3'-aarccnrancgGTTGCAGATGGAGGGC-5' |
| P450-terp-R4 (SEQ ID NO: 11) | HFDWKLPTG (SEQ ID NO: 61)<br>3'-gtraarctraccttyGACGGCTTCCC-5' |

Example 3

PCR Amplification of Vetiver P450 cDNAs

The primers described in Example 2 were used for the amplification of P450 cDNA fragments by PCR from the vetiver cDNA library. The PCRs were performed using the Advantage® 2 Polymerase Mix (Clontech, Takara Bio Europe). Each PCR mixture contained, in a total volume of 50 µL, 5 µL of Advantage® 2 PCR Buffer, 200 µM dNTPs, 200 nM each oligonucleotide primer, 5 µL of 200-fold diluted cDNA, 1 µL of Advantage® 2 Polymerase Mix. The following conditions were used for the amplifications:

3 minutes of denaturation at 94° C.;
 15 cycles of
  1 minute denaturation at 94° C.,
  1 min of annealing at 65° C. for the first cycle and minus one degree for each following cycle, and
  2 minutes extension at 72° C.;
 20 cycles of
  1 minutes denaturation at 94° C.,
  1 min of annealing at 58° C. and
  2 minutes extension at 72° C.; and
 finally 10 minutes extension at 72° C.

Different PCR were performed with the possible combinations of terpene-hydroxylase-specific sense and anti-sense primers. Amplicons with the expected size were cloned into the pCR®2.1-TOPO vector using the TOPO TA cloning Kit (Invitrogen, Carlsbad, Calif.), the inserts were subject to DNA sequencing and the sequence compared against the GenBank non-redundant protein database (NCBI) using the BLASTX algorithm (Altschul, S. F., Gish, W., Miller, W., Myers, E. W., and Lipman, D. J. (1990) J. Mol. Biol. 215, 403-410).

Several combination of primers (P450-terp-F1 (SEQ ID NO:5) with P450-terp-R2 (SEQ ID NO:9), P450-terp-F3 (SEQ ID NO:7) with P450-terp-R3 (SEQ ID NO:10), and P450-terp-F1 (SEQ ID NO:5) with P450-terp-R4 (SEQ ID NO:11)) provided DNA fragments with the expected size and with sequences showing homology to P450s sequences. Only fragments showing homology with characterized terpene monooxygenases were retained (approximately 50% of the fragments sequenced). The selected DNA sequences were aligned and a 1167-bp consensus DNA sequence (CA521 (SEQ ID NO:12) was deduced. The amino acid sequence deduced from CA521 showed identity as high as 45% with known plant terpene monooxygenases.

Full-length sequences were obtained with the technique of Rapid Amplification of cDNA Ends (RACE). The Marathon™ cDNA Amplification Kit (Clontech, Takara Bio Europe) was used for all RACE experiments. Typical RACE reaction mixtures contain, in a final volume of 50 μl, 5 μl Advantage® 2 PCR Buffer (Clontech, Takara Bio Europe), 200 μM each dNTP, 1 μl Advantage® 2 Polymerase Mix (Clontech, Takara Bio Europe), 200 μM adaptor-specific primer, 200 μM cDNA-specific primer and 5 μl of 200 fold diluted adaptor-ligated vetiver roots cDNA. Amplification was performed on an Eppendorf Mastercycler Gradiant thermal cycler. The thermal Cycling conditions were as follows: 1 min at 94° C., 5 cycles of 30 sec at 94° C. and 3 min at 72° C., 5 cycles of 30 sec at 94° C. and 3 min at 70° C., 20 cycles of 30 sec at 94° C. and 3 min at 68° C. When necessary a second round of amplification was performed using nested oligonucleotides. Amplicons with the expected size were cloned into the pCR®2.1-TOPO vector (Invitrogen, Carlsbad, Calif.) and the inserts were subject to DNA sequencing and the sequence compared against the GenBank non-redundant protein database (NCBI) using the BLASTX algorithm (Altschul, S. F., Gish, W., Miller, W., Myers, E. W., and Lipman, D. J. (1990) J. Mol. Biol. 215, 403-410).

For amplification of the CA-521 ends, sense and antisense oligonucleotides were deduced from the PCR-generated DNA fragments and were used in 3'RACE and 5'RACE: CA521-F1 (SEQ ID NO:13), CA521-F2 (SEQ ID NO:14), CA521-R1 (SEQ ID NO:15) and CA521-R2 (SEQ ID NO:16). Using the sense oligonucleotides, we obtained a 500 bp fragment (CA635 (SEQ ID NO:17)), sharing an overlap of 176 identical residues with the CA521 fragment. This CA635 fragment contained an additional 138 pb coding region, including the stop codon, followed by a 3' untranslated region. The 5'RACE provided a 426 bp fragment (CA884 (SEQ ID NO:18)) containing the missing 243 bp coding region at the 5'end.

Oligonucleotides were designed from the start and stop region of the reconstituted full-length sequence, CA521-start (SEQ ID NO:19), CA521-stop (SEQ ID NO:20), and used as primers for the amplification of the full-length cDNA. This amplification was performed using the Pfu DNA polymerase (Promega, Madison, Wis., USA), in a final volume of 50 μl containing 5 μl of Pfu DNA polymerase 10× buffer, 200 μM each dNTP, 0.4 μM each primer, 2.9 units Pfu DNA polymerase and 2.5 μl of the 200 fold-diluted vetiver cDNA. The thermal cycling conditions were as follows: 1.5 min at 95° C.; 30 cycles of 45 sec at 95° C., 30 sec at 64° C. and 4 min at 72° C.; and 10 min at 72° C. The PCR products were cloned into the pCR®2.1-TOPO vector using the TOPO TA cloning Kit (Invitrogen, Carlsbad, Calif.) and the DNA sequence was controlled. From the sequencing of several clones, two distinct DNA sequences (VzP521-11 (SEQ ID NO:21) and VzP521-16 (SEQ ID NO:22)) sharing 93% sequence identity, were retained. The deduced amino acid sequences, composed of 513 and 514 residues respectively, shared 89% identity. The amino acid sequence identity of VzP521-11 (SEQ ID NO:23) and VzP521-16 (SEQ ID NO:24) with the closest match in sequence databases are listed below.

| Accession numbers, denomination, organism | VzP521-11 | VzP521-16 |
|---|---|---|
| EER94164, hypothetical protein, *Sorghum bicolor* | 68% | 67% |
| ACF87848, unknown protein, *Zea mays* | 67% | 67% |
| EER96012, hypothetical protein, *Sorghum bicolor* | 65% | 65% |
| ACF86186, unknown protein, *Zea mays* | 65% | 64% |
| EER96013, hypothetical protein, *Sorghum bicolor* | 65% | 64% |
| EER92230, hypothetical protein, *Sorghum bicolor* | 63% | 61% |
| EAY78666, hypothetical protein, *Oryza sativa* | 61% | 61% |
| AAP53961, cytochrome P450 family protein, *Oryza sativa* | 61% | 60% |
| BAD17264, putative cytochrome P450, *Oryza sativa* | 59% | 58% |

The amino acid sequences identities with the closest publically available and functionally characterized proteins are listed in the table below:

| Accession numbers, function, organism | VzP521-11 | VzP521-16 |
|---|---|---|
| AAD44151, AAQ18706, AAD44152, AAT39473, AAQ18708, limonene hydroxylase, *Mentha* species. | 43 to 45% | 43 to 45% |
| AAK62432, premnaspirodiene oxygenase, *Hyoscyamus muticus*. | 50% | 48% |
| AAK62432, epi-aristolochene oxidase, *Nicotiana tabacum* | 46% | 45% |
| ADF43083, germacrene A oxidase, *Bernadesia spinosa* | 44% | 44% |
| ADM86719, valencene oxidase, *Chicorium intybus* | 45% | 46% |
| AF43081, germacrene A oxidase, *Saussura costus* | 43% | 44% |

The polypeptides VzP521-11 (SEQ ID NO:23) and VzP521-16 (SEQ ID NO:24) comprise one part which is a membrane anchor and an active region that is responsible of the catalytic P450 activity. The active regions of VZP521-11 and VzP521-16 are represented in SEQ ID NO: 1 and 2, respectively. The nucleic acid sequence encoding for these active sequences are represented in SEQ ID NO:3 and 4, respectively.

Example 4

Heterologous Expression of Vetiver P450s in Bacteria

In eukaryote P450 monooxygenases, the N-terminal sequence of the protein constitute a membrane anchor essential for the membrane localization of these enzymes. This part of the protein, delimited by a proline-rich domain (PPGP in 521-11 (SEQ ID NO:23) and 521-16 (SEQ ID NO:24)), is not essential for the control of the specificity of the enzymatic activity. This region can thus be modified by deletion, insertion or mutation without effect on the catalytic activity. However, specific modification of the N-terminal region of eukaryote P450s, including plant P450s, have been shown to have a positive effect on the levels of detected recombinant proteins when expressed in microorganisms (Halkier et al (1995) *Arch. Biochem. Biophys.* 322, 369-377; Haudenschield et al (2000) *Arch. Biochem. Biophys.* 379, 127-136). Thus, based on these previous observations the membrane anchor region of the P450s VzP521-11 and VzP521-16 were redesigned to introduce the modification shown in FIG. 3.

The modified cDNAs were obtained by PCR as follows. A first fragment corresponding to the membrane anchor region was amplified using the primers Pfus-NdeI (SEQ ID NO:25) and 521_fus_r (SEQ ID NO:26) (with the plasmid P2-2-48 (Haudenschield et al (2000) *Arch. Biochem. Biophys.* 379, 127-136) as template. Two other fragments were amplified using the primers 521-fus-f (SEQ ID NO:27) and 521-Hind (SEQ ID NO:28) and either the VzP521-11 (SEQ ID NO:21) or VzP521-16 (SEQ ID NO:22) cDNA as the template. A second round of PCR was performed using as template the first PCR product and either of the two latter PCR products and as primers Pfus-NdeI (SEQ ID NO:25) and 521-Hind (SEQ ID NO:28). All PCR were performed with the Pfu DNA polymerase (Promega, Madison, Wis., USA), in a final volume of 50 μl containing 5 μl of Pfu DNA polymerase 10× buffer, 200 μM each dNTP, 0.4 μM each primer, 2.9 units Pfu DNA polymerase and 2.5 μl of the 200 fold-diluted vetiver cDNA. The thermal cycling conditions were as follows: 1.5 min at 95° C.; 30 cycles of 45 sec at 95° C., 30 sec at 64° C. and 4 min at 72° C.; and a final step of 10 min at 72° C. The two PCR products, VzP521-11-1 (SEQ ID NO:37) and VzP521-16-1 (SEQ ID NO:38), were digested with the NdeI and HindIII restriction enzymes and ligated into the pCWori expression plasmid (Barnes H. J (1996) *Method Enzymol.* 272, 3-14) providing the plasmids pCW-218-521-11 and pCW-218-521-16 containing respectively the cDNA encoding for the N-terminal modified VzP521-11 and VzP521-16 P450s (VzP521-11-1 (SEQ ID NO:35) and VzP521-16-1 (SEQ ID NO:36) amino acid sequences).

For heterologous expression, the JM109 *E. coli* cells were transformed with the 218-521-11 or 218-521-16 expression plasmids. Single colonies of transformants were used to inoculated cultures of 5 mL LB medium containing 50 μg/mL ampicillin. The cells are grown for 10 to 12 hours at 37° C. The cultures were then used to inoculate 250 mL TB Medium (Terrific Broth) supplemented with 50 μg/mL ampicillin and 1 mM Thiamine HCL. The cultures were incubated at 28° C. for 3-4 h with moderate shaking (200 rpm) before 75 mg/L δ-aminolevulinic acid (sigma) and 1 mM IPTG (Isopropyl β-D-1-thiogalactopyranoside) was added, and the cultures were maintained at 28° C. for 24-48 h with 200 rpm shaking.

The expression of the P450 enzymes can be evaluated qualitatively and quantitatively by measuring the CO-binding spectrum (Omura, T. & Sato, R. (1964) *J. Biol. Chem.* 239, 2379-2387) in the *E. coli* protein fractions. For protein extraction, the cells are centrifuged (10 min, 5000 g, 4° C.) and resuspended in 35 mL ice-cold buffer 1 (100 mM Tris-HCl pH 7.5, 20% glycerol, 0.5 mM EDTA). One volume of 0.3 mg/ml lysozyme (from chicken egg white, Sigma-Aldrich) in water was added and the suspension left 10-15 min at 4° C. with agitation. The suspension is centrifuged 10 min at 7000 g and 4° C. and the pellet is resuspended in 20 mL buffer 2 (25 mM $KPO_4$ pH 7.4, 0.1 mM EDTA, 0.1 mM DTT, 20% glycerol). The suspension is subject to one cycle of freeze-thaw at −80° C., 0.5 mM PMSF (phenylmethylsulfonyl fluoride, Sigma-Aldrich) is added and the suspension is sonicated 3 times for 20 sec. The suspension is centrifuged 10 min at 10000 g (to remove cell debries) and the supernatant is recovered and centrifuged 2 hours at 100,000 g. The pellet (membrane protein fraction) is resuspended in 2-3 ml of buffer 3 (50 mM Tris-HCl pH 7.4, 1 mM EDTA, 20% glycerol). To measure the CO-spectrum, the protein fraction is diluted (1/10) in buffer 3 to a final volume of 2 mL. Some crystals of sodium dithionite ($Na_2S_2O_4$) are added, the sample is divided into two cuvettes and the baseline recorded between 370 and 500 nm. The sample cuvette is then saturated with carbon monoxide and the difference spectrum is recorded. The concentration of P450 enzyme can be estimated from the amplitude of the peak at 450 nm using the extension coefficient for the reduced CO complex of 91 $mM^{-1} \cdot cm^{-1}$ (Omura, T. & Sato, R. (1964) J. Biol. Chem. 239, 2379-2387).

Figure 4:
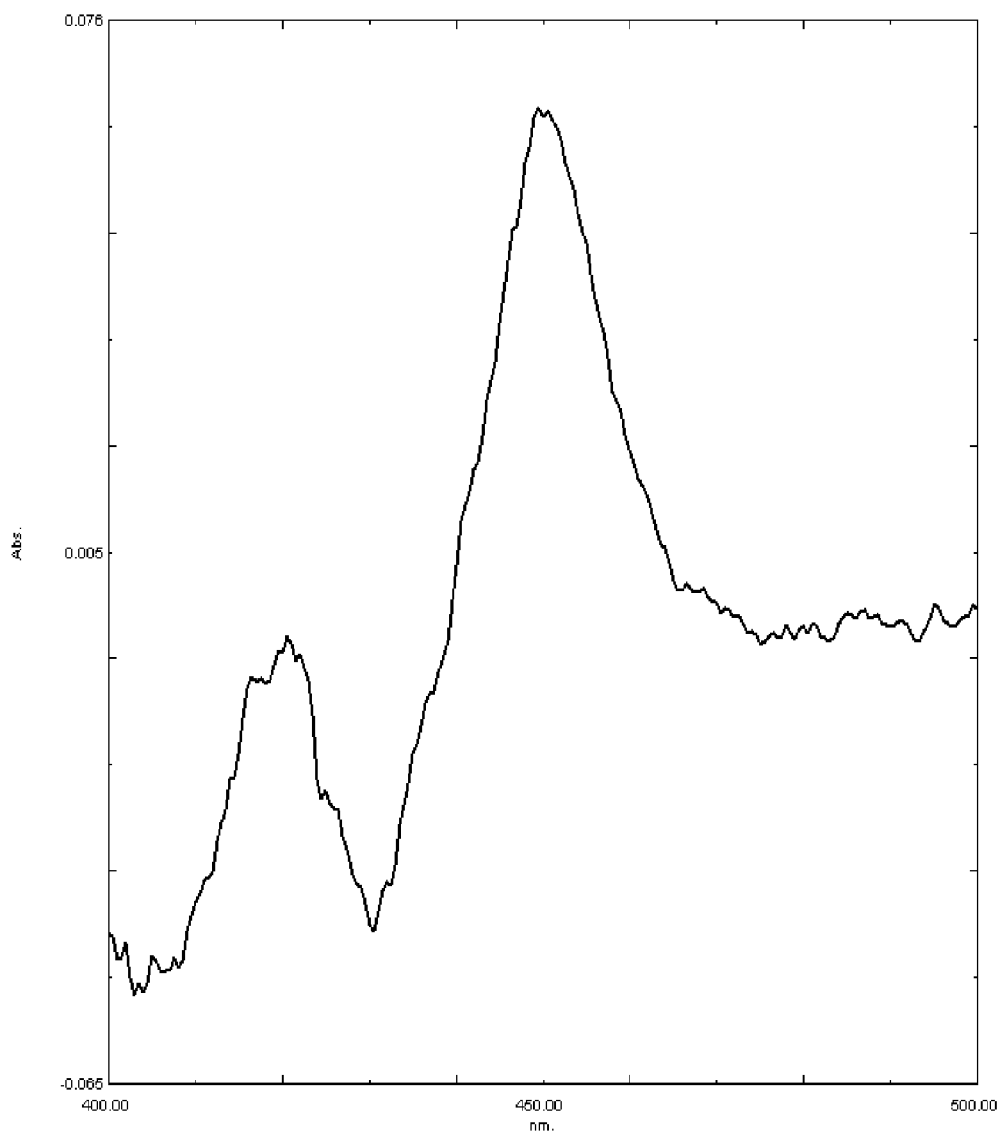
FIG. 4: Representative CO-differential spectrum obtained with the VzP521-11 recombinant protein.

Following this procedure, typical CO-spectra with a maximum absorbance at 450 nm were measured for the recombinant VzP521-11-1 (SEQ ID NO:35) and VzP521-16-1 (SEQ ID NO:36) proteins, attesting for a proper folding into functional P450 enzymes (FIG. 4).

Example 5

Heterologous Expression of Plant P450-Reductases in Bacteria

To reconstitute the activity of plant P450s, the presence of a second membrane protein is essential. This protein, the P450-reductase (CPR), is involved in the transfer of electrons from NADPH (Nicotinamide adenine dinucleotide phosphate, reduced form) to the P450 active site. It has been shown that a CPR from one plant can complement the activity of P450 enzyme from another plant (Jensen and Moller (2010) *Phytochemsitry* 71, 132-141).

Several CPR-encoding nucleotidic sequences have been reported from different plant sources. For instance, two distinct CPRs, ATR1 and ATR2 (NCBI access. No. CAA46814.1 and CAA46815), have been identified in *Arabidopsis thaliana* (Urban et al (1997) *J. Biol. Chem.* 272(31) 19176-19186). These CPRs have been shown to complement several P450 enzymes from various plant species. A cDNA (sequence tcATR1-opt (SEQ ID NO:29) encoding for a truncated version of ATR1 (17 N-terminal amino acid deletion) was synthesized using a codon usage optimal for the expression in *E. coli* (DNA 2.0, Menlo Park, Calif., USA) and including NcoI and BamHI restriction sites at the 5'-end and 3'-end, respectively. This cDNA was ligated into the pJ206 plasmid (DNA2.0, Menlo Park, Calif., USA) providing the plasmid pJ206-tcATR1-opt. The insert was digested from the pJ206-tcATR1-opt plasmid with the NcoI and BamHI restriction enzymes and ligated between the corresponding restriction sites of the pACYCDuet-1 expression plasmid (Novagen, Merck Chemicals) providing the plasmid pACYC-tcATR1-opt. Functional expression of CPRs in *E. coli* cells can be estimated following the enzymatic reduction of cytochrome C. The plasmid pACYC-tcATR1-opt was used to transform B121(DE3) (Novagen) or JM109(DE3) (Promega, Madisson, Wis., USA) *E. coli* cells. Culture conditions, protein expression and cell-free protein preparation were made as described in Example 4. The proteins are diluted in 1 mL Tris pH 7.4 supplemented with 5 μM FAD, 5 μM FMN, 40 mM cytochrome C (sigma-Aldrich), 1 mM $MgCl_2$. The reaction is initiated by addition of 0.12 mmoles NADPH (Sigma). The reduction of cytochrome C is recorded by measuring the increase of OD at 550 nm over 0.5 to 2 minutes. The reductase specific activity (in mUnits/μL) was calculated using the following formula: (ODend-ODstrat)/21/time (sec)/Vol (μL)×60000 (in mUnits/μL). Typically activity measured with the recombinant ATR1 ranged between 7 and 10 mUnits/mL.

Example 6

Coexpression of a P450 and a P450 Reductase Using Two Plasmids

For a whole cell biotransformation using plant P450s, co-expression of the P450 and CPR proteins in a single host cell is required. This co-expression can be obtained using two plasmids. For example, BL21 Star™(DE3) *E. coli* cells (Invitrogen, Carlsbad, Calif.) were co-transformed with the plasmid pACYC-tcATR1-opt and the plasmid pCW-218-521-11 or pCW-218-521-16. Transformed cells were selected on carbenicillin (50 μg/ml) and chloramphenicol (34 μg/ml) LB-agarose plates. Single colonies were used to inoculate 5 mL liquid LB medium supplemented with the same antibiotics. The culture was incubated overnight at 37° C. The next day 2 to 250 mL of TB medium supplemented with the same antibiotics and 1 mM Thiamine HCL were inoculated with 0.2 mL of the overnight culture. After 6 hours incubation at 37° C., the culture was cooled down to 28° C. and 1 mM IPTG and 75 mg/L δ-aminolevulinic acid were added. The culture was maintained from 24 to 36 hours. Protein fractions were prepared as described in Example 4 and the expression of the recombinant P450 and CPR was evaluated using the procedure described in Examples 4 and 5, respectively.

Example 7

Co-Expression of a P450 and a P450 Reductases from a Single Plasmid

Expression plasmids with a bi-cistronic construct (SEQ ID: NO 54) comprising a cDNA encoding for a vetiver P450 and a cDNA encoding for CPR were prepared. The constructs were designed to insert between the two coding regions a spacer sequence including a ribosome binding site (RBS) (see FIG. 5).

The tcATR1-opt cDNA (SEQ ID NO:29) synthesized with *E. coli* optimal codon usage (DNA 2.0, Menlo Park, Calif., USA) was modified to add at the 5'-end, before the start codon, a 30 bp extension containing the spacer sequence (SEQ ID NO:30) and the RBS sequence. The tcATR1-opt cDNA was amplified using the primers 2390-CPR-F2 (SEQ ID NO:31) and 2390-CPR-R2b (SEQ ID NO:32) using the Pfu DNA polymerase (Promega, Madison, Wis., USA), in a final volume of 50 μl containing 5 μl of Pfu DNA polymerase 10× buffer, 200 μM each dNTP, 0.4 μM each primer, 2.9 units Pfu DNA polymerase and 2.5 μl of the 50 ng of pJ206-tcATR1-opt plasmid. The thermal cycling conditions were as follows: 1.5 min at 95° C.; 30 cycles of 45 sec at 95° C., 30 sec at 60° C. and 4 min at 72° C.; and 10 min at 72° C. After purification on agarose gel, the PCR product was ligated in the pCW-218-521-11 and pCW-218-521-16 plasmids digested by HindIII using the In-Fusion® Dry-Down PCR Cloning Kit (Clontech, Takara Bio Europe) following the manufacturer instruction. The resulting two plasmids pCW-2391-521-11 and pCW-2392-521-16 contain the bi-cistronic constructs consisting of the VzP521-11-1 and VzP521-16-1 sequences respectively followed by the tcATR1-opt sequence.

*E. coli* cells were transformed with one of these two plasmids and the membrane protein fractions were prepared as described in Example 4. The P450 and CPR expression was verified following the CO-binding spectra and the NADPH reduction assays as described in Examples 4 and 5.

Example 8

Bioconversion of Zizaene to Khusimol Using Whole Cells of *E. coli* Expressing the Vetiver P450s and CPR The oxidation of (+)-zizaene can be performed using whole *E. coli* cells expressing the vetiver P450s and a CPR (bioconversion). Zizaene was prepared using engineered *E. coli* cells following the method described in the patent WO 2010/134004 and using the sesquiterpene synthase with the sequence accession number HI931369.

In brief, BL21Star™(DE3) *E. coli* cells (Invitrogen Ltd) were transformed with the plasmid pACYC-4506 and the plasmid pETDuet-VzZS-opt. The plasmid pACYC-4506 contains the genes encoding for the five enzymes of a biosynthetic pathway converting mevalonic acid to FPP: a mevalonate kinase (MvaK1), a phosphomevalonate kinase (MvaK2), a mevalonate diphosphate decarboxylase (MvaD), an isopentenyl diphosphate isomerase (idi) and farnesyl diphosphate synthase (FPS). To construct this plasmid, the FPS gene was amplified from *S. cerevisiae* genomic DNA and ligated in the first multiple cloning site (MCS) of the pACYCDuet-1 and an operon encoding the genes for a MvaK1, a MvaK2, a MvaD and an idi was amplified from genomic DNA of *Streptococcus pneumoniae* (ATCC BAA-334) and ligated into the second MCS. The pETDuet-VzZS-opt contains a codon optimized version of the vetiver (+)-zizaene synthase (as described in SEQ ID NO:11 of WO 2010/134004).

Single colonies of transformed cells were used to inoculate 5 mL of LB medium supplemented with carbenicillin (50 mg/ml) and chloramphenicol (34 mg/ml). Cultures were incubated overnight at 37° C. The next day 1 L of Terrific Broth (TB) medium supplemented with the same antibiotics were inoculated with 1/100 volume of the overnight culture. After 6 h incubation at 37° C., cultures were cooled down to 28° C. and 1 mM IPTG, 2 g/L mevalonic acid prepared by dissolving mevalonolactone (Sigma-Aldrich) in 0.5N NaOH at a concentration of 1 g/mL and incubating the solution for 30 min at 37° C.), and 100 g/L of Amberlite™ XAD™-4 resin (Rhom and Haas) were added to the cultures. After 48 h incubation, the resin was recovered, rinsed with water and eluted with 3 volumes of diethyl-ether. The solvent was removed and the product purified by silica gel flash-chromatography using n-hexane as solvent. The fractions containing (+)-zizaene were pooled, the solvent removed by distillation and the residue was used as substrate for the oxidation assays.

*E. coli* cells (BL21Star™(DE3) *E. coli* cells (Invitrogen Ltd) or JM109(DE3) (Promega)) were transformed with the plasmids pCW-2391-521-11 or pCW-2392-521-16 or cells were co-transformed with the plasmids pCW-218-521-11 or pCW-218-521-16 and pACYC-tcATR1-opt and were grown in TB medium supplemented with 3% glycerol or LB medium supplemented with 1% glucose. The cultures were incubated at 37° C. until reaching an optical density of 1. The cultures were then transferred to 28° C., 1 mM IPTG and 74 μg/ml δ-aminolevulinic acid were added and the culture were incubated for 24 hours.

The cells were harvested in exponential growing phase, centrifuged and resuspended in 0.5 volume of potassium phosphate buffer 50 mM pH 7.0 supplemented with 5% glycerol or 3% glucose. The substrate ((+)-zizaene) was added to a final concentration of 0.5 mg/ml as mixture composed of 10 mg Tween® 20 (sigma-Aldrich), 10 mg antifoam (Erol DF, PMC Ouvrie, Lesquin, France), 20 mg (+)-zizaene and 1 ml water. The conversion was allowed to proceed for 24 hours at 20° C. with moderate shaking. The media were extracted with 2 volumes of ethyl-acetate and the extracts were analyzed by GCMS on an Agilent 6890 Series GC system connected to an Agilent 5975 mass detector. The GC was equipped with 0.25 mm inner diameter by 30 m SPB-1 capillary column (Supelco, Bellefonte, Pa.). The carrier gas was He at a constant flow of 1 mL/min. The initial oven temperature was 50° C. (1 min hold) followed by a gradient of 10° C./min to 300° C. The identification of the products was based on the comparison of the mass spectra and retention indices with authentic standards and internal databases.

Figure 7:
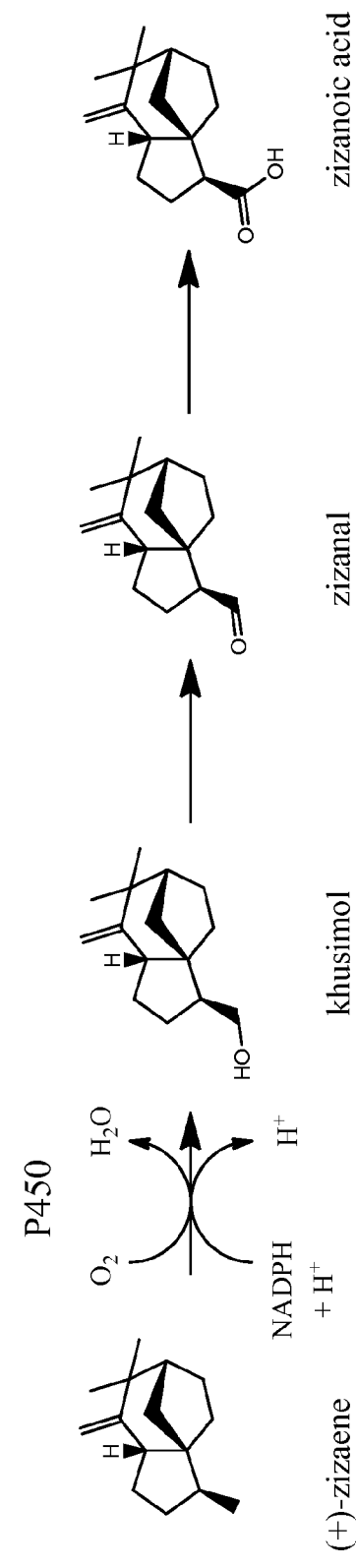
FIG. 7: Scheme showing the successive steps of the enzymatic oxidation of zizaene.

In these conditions the oxidation of (+)-zizaene was observed with cells containing the VzP521-11-1 and VzP521-16-1 recombinant proteins. Three products were observed and identified by GCMS analysis: khusimol, zizanal and zizanoic acid, resulting from the successive oxidation of (+)-zizaene (FIG. 6). The VzP521-11-1 and VzP521-162-1 enzymes catalyse thus the oxidation of (+)-zizaene to khusimol. The further oxidation of khusimol to zizanal and zizanoic acid could be catalysed by the recombinant P450s or by endogenous E. coli enzymatic activities (FIG. 7).

Example 9

Bioconversion of Other Monoterpene and Sesquiterpene Molecules Using Whole Cells of E. coli Expressing the Vetiver P450s and CPR E. coli cells expressing the vetiver P450s and a CPR were prepared, grown and the bioconversions performed using resting cells in potassium phosphate buffer as described in Example 8.

Figure 1:
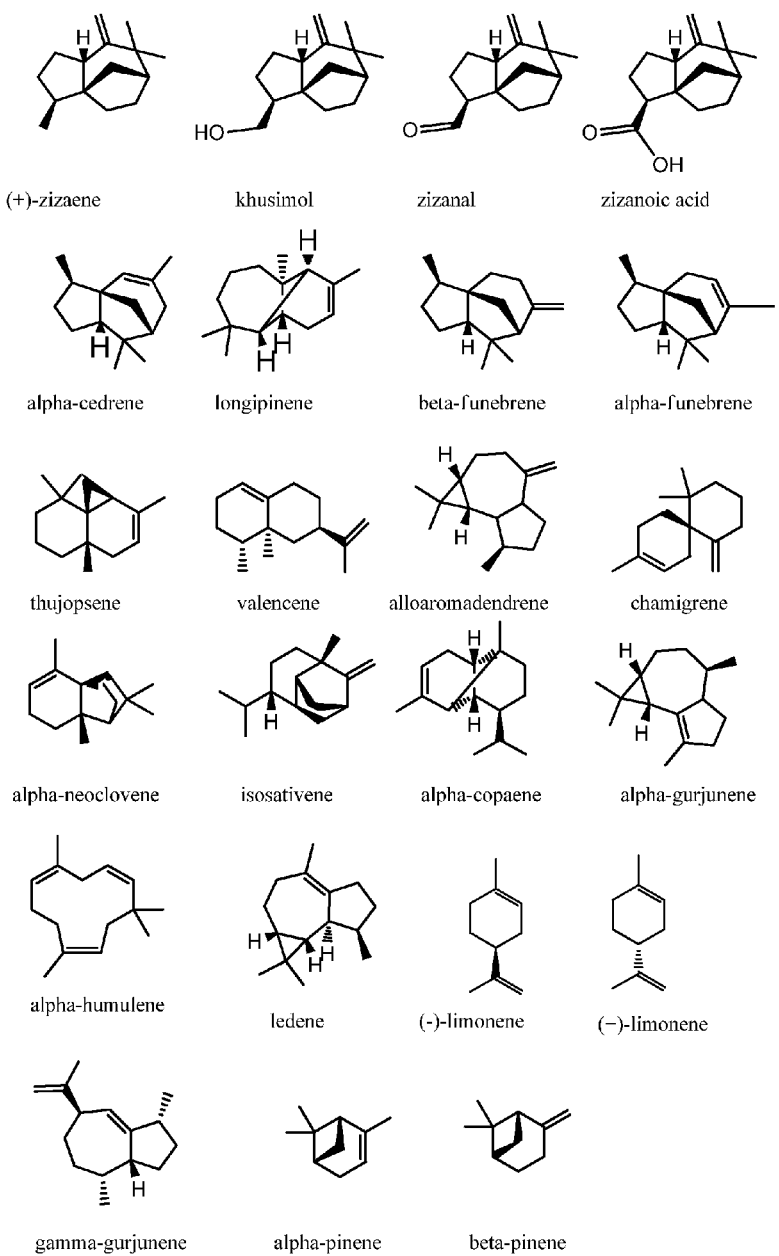
FIG. 1: Structures of cited compounds.
Figure 8:
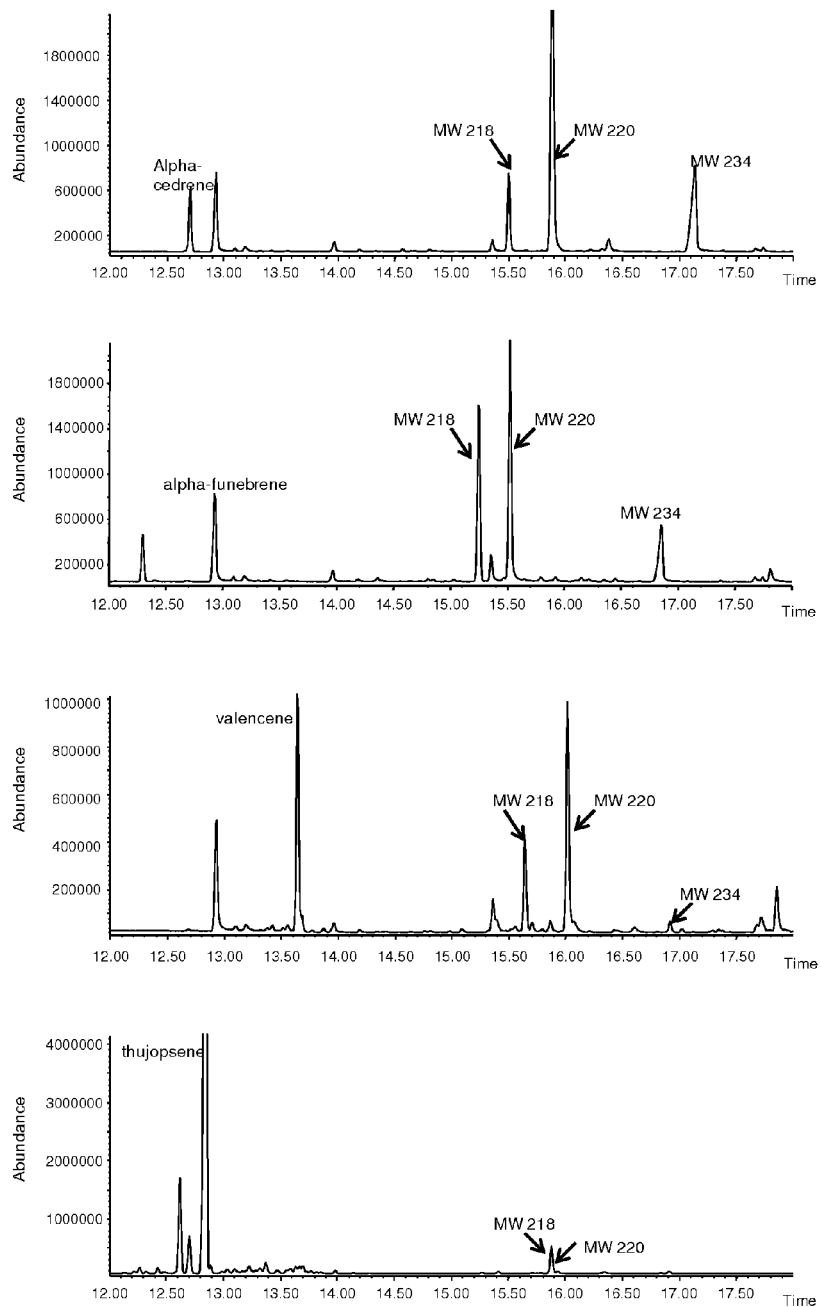
FIG. 8: Total ion chromatogram of the GCMS analysis of the bioconversion of several terpene molecules by the vetiver P450s. The peaks corresponding to the substrate are indicated and the molecular weights of the products are indicated.
Figure 9:
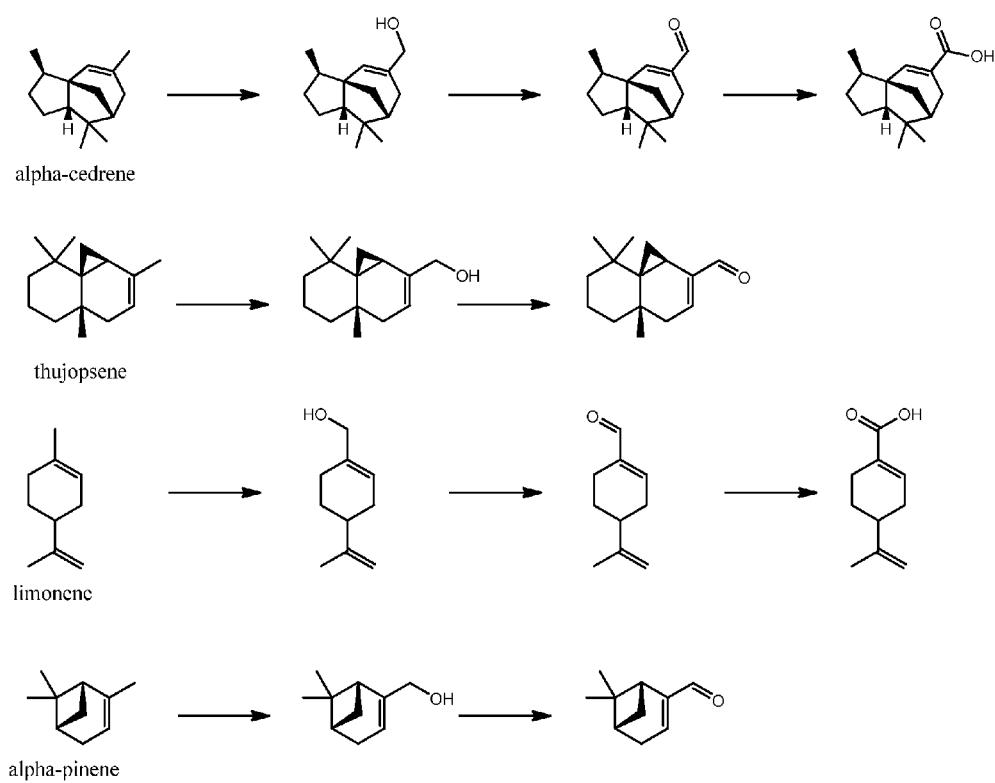
FIG. 9: Scheme showing the bioconversion by the vetiver P450s of several terpene molecules for which the products were identified.

Assays were performed with several terpene molecules and the formation of oxygenated terpene molecules was evaluated using GCMS analysis as described in Example 8. In addition to (+)-zizaene, bioconversion was observed with the following molecules: (+)-limonene, (−)-limonene, alpha-pinene, alpha-cedrene, alpha-longipinene, alpha-funebrene, thujopsene, valencene, beta-chamigrene, alloaromadendrene, alpha neoclovenene, isosativene, ledene, alpha-humulene, alpha gurjunene, gamma-gurjunene, beta-funebrene, alpha-copaene, alpha-gurjunene and beta-pinene. The structures of these molecules are shown in FIG. 1. Examples of chromatograms from GCMS analysis of these bioconversions are shown in FIG. 8. For some of the substrates tested, the products could be identified and are shown in FIG. 9.

Example 10

In-Vitro Oxidation of Compounds Using the Vetiver P450s

The oxidation of sesquiterpene using the P450s from vetiver can also be performed in-vitro using cell lysates or partially purified protein.

E. coli cells (BL21Star™(DE3) E. coli cells (Invitrogen Ltd) or JM109(DE3) (Promega)) were transformed with the plasmids pCW-2391-521-11 or pCW-2392-521-16 or cells were co-transformed with the plasmids pCW-218-521-11 or pCW-218-521-16 and pACYC-tcATR1-opt. The cells culture conditions, the expression of the proteins and the membrane proteins preparation were as described in Examples 4 and 5. These protein fractions were used for in-vitro conversion of (+)-zizaene or the terpene molecules listed in Example 9. Typical assays are composed of 20 to 50 µL of proteins, 0.4 mg NADPH (Sigma), 5 µM FAD (Flavin adenine dinucleotide, Sigma), 5 µM FMN (Flavin mononucleotide, Sigma), 0.05 mg (+)-zizaene in a total volume of 1 mL of 100 mM Tris buffer pH 7.4. In some assays, NADPH-reconstitution system was added and consisted of 25 mM glucose 6-phosphate (Sigma) and 6 mUnits glucose 6-phosphate dehydrogenase (Sigma). Assays were incubated 2 to 12 hours at 30° C. Samples were then extracted twice with one volume of ethyl acetate and analyzed by GCMS as described in Example 8.

Using his approach the same products are obtained as when using whole E. coli cells as described in Examples 8 and 9.

Example 11

In-Vivo Production of Khusimol in Engineered Cells

The oxidized products of (+)-zizaene can also be produced in E. coli cells engineered to produce sesquiterpenes from a carbon source such as glucose or glycerol. Plasmids were prepared consisting of the pCWori (Barnes H. J (1996) Method Enzymol. 272, 3-14) plasmid containing an operon composed of the P450, the P450-reductase and the terpene synthase. Two plasmids were thus prepared by inserting an RBS sequence and the optimized sequence encoding for the (+)-zizaene synthase (VzZS) after the stop codon of the CPR sequence in the pCW-2391-521-11 or pCW-2392-521-16.

Figure 10:
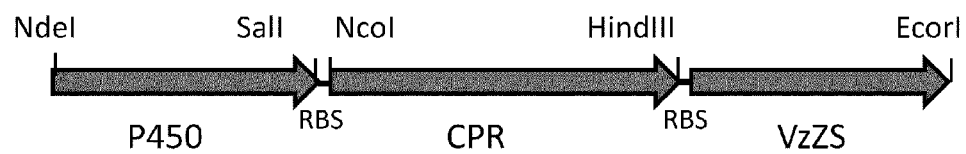
FIG. 10: Organisation of the artificial operon designed for the co-expression in E. coli of the vetiver P450s, a CPR and the zizanene synthase.

The VzZS was amplified from pETDuet-VzZS-opt plasmid (as described in WO 2010/134004) using the primers 2401-VzZS-F (SEQ ID NO:33) and 2401-VzZS-R (SEQ ID NO:34). The PCR was performed using the Pfu DNA polymerase (Promega, Madison, Wis., USA), in a final volume of 50 µl containing 5 µl of Pfu DNA polymerase 10× buffer, 200 µM each dNTP, 0.4 µM each primer, 2.9 units Pfu DNA polymerase and 50 ng of template. The thermal cycling conditions were as follows: 1.5 min at 95° C.; 30 cycles of 45 sec at 95° C., 30 sec at 60° C. and 4 min at 72° C.; and 10 min at 72° C. The PCR product was purified and ligated in the pCW-2391-521-11 or pCW-2392-521-16 plasmids digested with the HindIII and EcorI restriction enzymes. This ligation was performed using the In-Fusion® Dry-Down PCR Cloning Kit (Clontech, Takara Bio Europe) following the manufacturer's instructions. The resulting plasmids pCW-2401-521-11 and pCW-2402-521-16 contain an insert consisting of the VzP521-11-1 or VzP521-16-1 sequence respectively, the tcATR1-opt sequence (P450 reductase) and the VzZS sequence ((+)-zizaene synthase) (FIG. 10).

Another expression plasmid was prepared containing two operons consisting of the genes encoding the enzymes for a complete mevalonate pathway. A first synthetic operon consisting of an Escherichia coli acetoacetyl-CoA thiolase (atoB), a Staphylococcus aureus HMG-CoA synthase (mvaS), a Staphylococcus aureus HMG-CoA reductase (mvaA) and a Saccharomyces cerevisiae FPP synthase (ERG20) genes was chemically synthetized (DNA2.0, Menlo Park, Calif., USA) and ligated into the NcoI-BamHI digested pACYCDuet-1 vector (Invitrogen) yielding pACYC-29258. The genes of this plasmid encode for the enzymes necessary for the conversion of acetyl-CoA to mevalonate and for a FPP synthase. The second operon contains the genes encoding for the four enzymes necessary for the conversion of mevalonate to IPP and DMAPP and was amplified from the plasmid pACYC-4506 (Example 8) using the primers: 5'-AAGGAGATATACATAT-GACAAAAAAAAGTTGGTGTCGGTCAGG-3' (SEQ ID NO: 39) and 5'-CTTTACCAGACTCGAGTTACGC-CTTTTTCATCTGATCCTTTGC-3' (SEQ ID NO: 40). The resulting amplicon was cloned into the NdeI-XhoI digested pACYC-29258 vector using the In-Fusion 2.0 Dry-Down PCR Cloning Kit (Clontech) providing the pACYC-29258-4506 vector.

OverExpress™ C43(DE3) *E. coli* cells (Lucigen® Corporation) were co-transformed with the plasmid pACYC-29258-4506 and the plasmid pCW-2401-521-11 or the plasmid pCW-2402-521-16. Single colonies of transformed cells were used to inoculate 5 mL of LB medium supplemented with carbenicillin (100 µg/ml) and chloramphenicol (17 µg/ml). The cultures were incubated overnight at 37° C. and used to inoculate M9 medium supplemented with 2 g/L yeast extract, 3% glycerol, 10 µM $FeSO_4$, 100 µg/ml carbenicillin and 17 µg/ml chloramphenicol. The cultures were incubated 6 h at 37° C., cooled down to 25° C. and 0.1 mM IPTG, 74 µg/ml δ-aminolevulinic acid and 1/10 volume dodecane were added. After 48 hours, the cultures were extracted with 2 volumes of tert-Butyl methyl ether (MTBE) and the extracts analyzed by GCMS as described in Example 8, except for the oven temperature that was initially set at 80° C. with one minute hold, followed by gradient of 10° C./min to 300° C.

Figure 11:
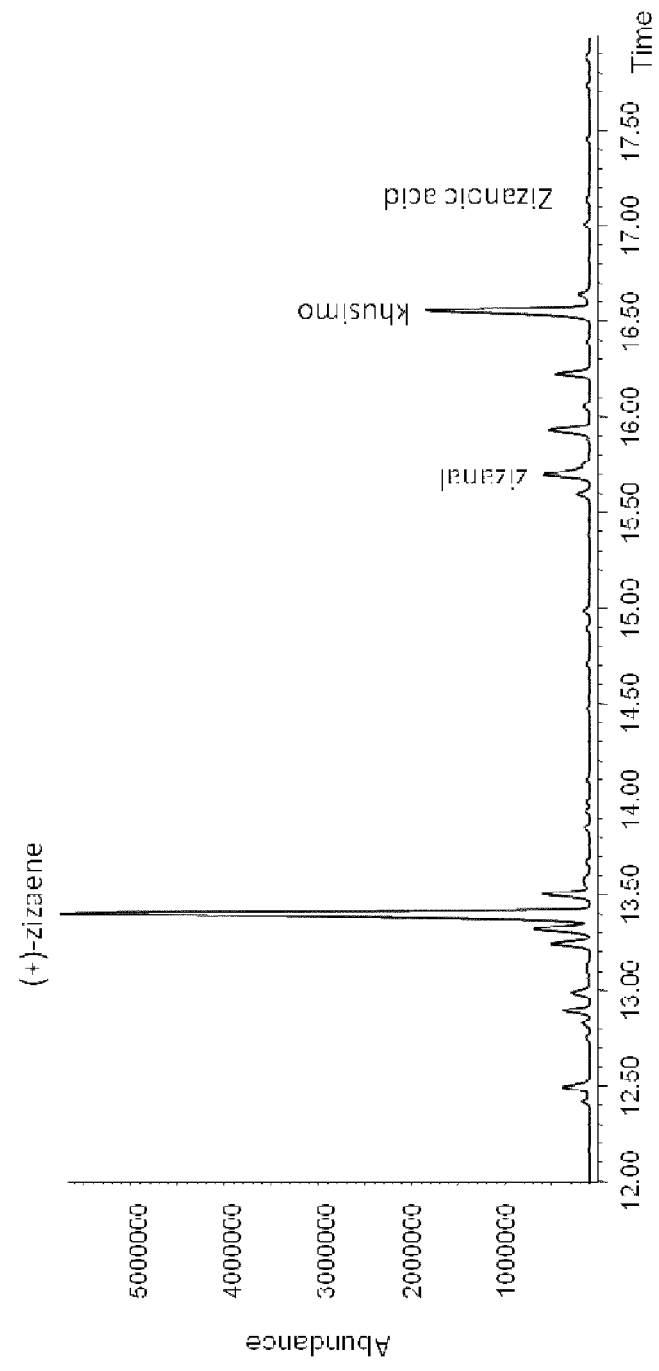
FIG. 11: Total ion chromatogram of a GCMS analysis of the sesquiterpene produced by E. coli cells expressing the (+)-zizaene synthase, the vetiver P450 VzP521-16-1 and the arabidopsis CPR, together with the enzymes for production of FPP using an heterologous mevalonate pathway.

The sesquiterpene (+)-zizaene and the derived alcohol and aldehyde (khusimol and zizanal) were detected. The zizanoic acid was also found as minor product (FIG. 11). This experiment shows that, in the engineered cells, the sesquiterpene (+)-zizaene is produced and is oxidized by the heterologous P450 and CPR complex.

This example shows that an *E. coli* cell transformed to express a polypeptide according to the invention is capable of oxidizing terpene compounds such as zizaene, provided that it is used in combination with a P450-reductase. The other enzymes with which the *E. coli* cell is transformed are not essential for such oxidation. Indeed the oxidized terpene is also produced when an *E. coli* cell is transformed with the cytochrome P450, the reductase and the terpene synthase only, but in lower amount. Such other enzymes with which the *E. coli* cell is transformed, are added for the unique purpose of increasing the amount of terpene available as substrate for the cytochrome P450.

SEQUENCE LISTING

```
<160> NUMBER OF SEQ ID NOS: 61

<210> SEQ ID NO 1
<211> LENGTH: 472
<212> TYPE: PRT
<213> ORGANISM: Vetiveria zizanioides

<400> SEQUENCE: 1

Trp Thr Leu Pro Val Ile Gly Ser Leu His His Val Ile Thr Tyr Pro
1               5                   10                  15

Asn Leu His Arg Ala Leu His Gly Leu Ala Gln Lys Tyr Gly Pro Val
            20                  25                  30

Met Met Phe Arg Leu Gly Glu Val Pro Met Met Val Val Ser Ser Pro
        35                  40                  45

Ala Ala Ala Gln Glu Ala Leu Lys Thr Asn Asp Ile Ala Phe Ala Asp
    50                  55                  60

Arg Tyr Thr Asn Ala Thr Ile Gly Ala Leu Thr Phe His Gly Glu Asp
65                  70                  75                  80

Met Ala Phe Ala Pro Tyr Gly Glu Arg Trp Arg Gln Leu Arg Lys Ile
                85                  90                  95

Cys Val Leu Glu Leu Leu Ser Ala Ala Arg Val Gln Ser Phe Arg His
            100                 105                 110

Ile Arg Ala Glu Glu Val Ser Arg Leu Val Gly Lys Leu Ala Ala Ser
        115                 120                 125

Ala Ala Ala Gly Glu Ala Val His Leu Asn Lys Ile Val Ala Lys Phe
    130                 135                 140

Val Asn Asp Thr Ile Val Arg Glu Ala Val Gly Ser Gly Ser Lys His
145                 150                 155                 160

Gln Asp Glu Tyr Leu Asn Ser Ile Asp Val Ala Leu Arg Gln Thr Met
                165                 170                 175

Gly Val Ala Leu Ala Asp Leu Phe Pro Ser Ser Arg Leu Ile Gln Met
            180                 185                 190

Ile Asp Thr Ala Pro Arg Lys Val Leu Ala Ala Arg Asn Asn Met Glu
        195                 200                 205
```

Arg Ile Leu Glu Glu Ile Ile Asn Glu Thr Lys Ala Met Asp Arg
210                 215                 220

Gly Asp Gly Gln Lys Lys Val Glu Gly Ile Leu Gly Val Leu Leu Arg
225                 230                 235                 240

Leu Gln Lys Glu Gly Ser Thr Pro Val Pro Leu Thr Asn Glu Val Ile
            245                 250                 255

Val Thr Val Met Phe Asp Met Phe Gly Ala Gly Ser Asp Thr Ser Ser
            260                 265                 270

Thr Leu Leu Thr Trp Cys Met Met Glu Leu Val Arg Ser Pro Pro Thr
        275                 280                 285

Met Ala Lys Val Gln Asp Glu Val Arg Glu Ala Phe Lys Gly Lys Lys
        290                 295                 300

Glu Ser Thr Ile Ile Thr Glu Asp Asp Leu Lys Gly Leu Thr Tyr Leu
305                 310                 315                 320

Lys Gln Val Ile Lys Glu Ala Leu Arg Met His Pro Pro Val Pro Leu
            325                 330                 335

Leu Leu Pro Arg Lys Cys Arg Glu Thr Cys Lys Val Met Gly Tyr Asp
            340                 345                 350

Ile Pro Lys Gly Thr Val Val Phe Ala Asn Ala Trp Ala Ile Gly Arg
            355                 360                 365

Asp Pro Lys Tyr Trp Glu Asp Pro Glu Glu Phe Lys Pro Glu Arg Phe
370                 375                 380

Asp Lys Ser Asn Val Asp Tyr Lys Gly Thr Asn Phe Glu Tyr Leu Pro
385                 390                 395                 400

Phe Gly Ser Gly Arg Arg Ile Cys Pro Gly Ile Asn Leu Gly Leu Cys
            405                 410                 415

Asn Ile Glu Leu Ala Leu Ala Ser Leu Leu Tyr His Phe Asp Trp Lys
            420                 425                 430

Leu Pro Asn Gly Met Glu Pro Lys Asp Ile Asp Met Gly Glu Ala Gln
            435                 440                 445

Gly Leu Ile Ala Ser Lys Lys Thr Asn Leu Thr Leu His Pro Val Thr
450                 455                 460

Arg Ile Ala Pro Ala Gly Phe Asn
465                 470

<210> SEQ ID NO 2
<211> LENGTH: 473
<212> TYPE: PRT
<213> ORGANISM: Vetiveria zizanioides

<400> SEQUENCE: 2

Trp Thr Leu Pro Val Ile Gly Ser Leu His His Val Ile Thr Tyr Pro
1               5                   10                  15

Asn Leu Gln Arg Ala Leu Arg Val Leu Ala Gln Lys Tyr Gly Pro Val
            20                  25                  30

Met Met Phe Gln Leu Gly Glu Val Pro Met Met Val Val Ser Ser Pro
        35                  40                  45

Ala Ala Ala Gln Glu Val Leu Lys Thr Asn Asp Leu Thr Phe Ala Asp
    50                  55                  60

Arg Tyr Thr Asn Ala Thr Ile Gly Ala Leu Thr Phe His Gly Glu Asp
65                  70                  75                  80

Met Val Phe Ala Pro Tyr Gly Glu Arg Trp Arg Gln Leu Arg Lys Ile
                85                  90                  95

Cys Met Leu Glu Leu Leu Ser Ala Ala Arg Val Gln Ser Phe Arg His

```
                100                 105                 110
Ile Arg Glu Glu Val Ala Arg Leu Val Gly Asn Ile Ala Thr Ser
            115                 120                 125
Ala Ala Ala Gly Glu Ala Val His Leu Asn Lys Met Val Ser Arg Phe
    130                 135                 140
Val Asn Asp Thr Val Val Arg Glu Ala Val Gly Ser Gly Ser Lys His
145                 150                 155                 160
Gln Glu Glu Tyr Leu Ser Ser Leu Asn Val Ala Leu Arg Gln Thr Met
                165                 170                 175
Gly Val Ala Val Ala Asp Leu Phe Pro Ser Ser Arg Leu Met Gln Met
            180                 185                 190
Ile Asp Thr Ala Pro Arg Lys Val Leu Ala Ala Arg Asn Asn Met Val
        195                 200                 205
Arg Ile Leu Glu Glu Ile Ile Lys Glu Thr Lys Glu Ala Met Glu Cys
    210                 215                 220
Gly Asp Gly Gln Glu Lys Val Glu Gly Ile Leu Gly Val Leu Leu Arg
225                 230                 235                 240
Leu Gln Lys Glu Gly Ser Thr Pro Val Pro Leu Thr Asn Glu Val Ile
                245                 250                 255
Val Thr Val Met Phe Asp Met Phe Gly Ala Gly Ser Asp Thr Ser Ser
            260                 265                 270
Thr Leu Leu Thr Trp Cys Met Thr Glu Leu Val Arg Ser Pro Pro Thr
        275                 280                 285
Met Ala Lys Val Gln Asp Glu Val Arg Gln Ala Ile Lys Gly Lys Lys
    290                 295                 300
Gln Ser Pro Ile Val Ile Thr Glu Asp Asp Leu Lys Gly Leu Thr Tyr
305                 310                 315                 320
Leu Lys Gln Val Ile Lys Glu Thr Leu Arg Met His Thr Pro Leu Pro
                325                 330                 335
Leu Leu Leu Pro Arg Lys Cys Arg Glu Thr Cys Lys Val Met Gly Tyr
            340                 345                 350
Asp Ile Pro Lys Gly Thr Val Val Phe Ala Asn Ala Trp Ala Ile Cys
        355                 360                 365
Arg Asp Pro Lys Tyr Trp Glu Asp Ser Glu Glu Phe Lys Pro Glu Arg
    370                 375                 380
Phe Asp Lys Ser Ser Leu Asp Tyr Lys Gly Thr Asn Phe Glu Tyr Leu
385                 390                 395                 400
Pro Phe Gly Ser Gly Arg Arg Ile Cys Pro Gly Ile Asn Leu Gly Leu
                405                 410                 415
Gly Asn Ala Glu Ile Ala Leu Ala Ser Leu Leu Tyr His Phe Asp Trp
            420                 425                 430
Lys Leu Pro Asp Gly Met Glu Pro Lys Asp Val Asn Met Glu Glu Ala
        435                 440                 445
Gln Gly Leu Val Ala Ser Lys Lys Thr Asn Leu Thr Leu Tyr Pro Val
    450                 455                 460
Thr Arg Ile Ala Pro Ala Gly Phe Asn
465                 470

<210> SEQ ID NO 3
<211> LENGTH: 1419
<212> TYPE: DNA
<213> ORGANISM: Vetiveria zizanioides

<400> SEQUENCE: 3
```

```
tggacgctgc cggtgatcgg cagcctccac cacgtgatca cctaccccaa cctccaccgc    60
gcactgcacg ggctggcgca gaagtacggt ccggtgatga tgttccggct cggcgaggtg   120
ccaatgatgg tggtgtcgtc gccggcggcc gcgcaggagg ccctcaagac gaacgacatc   180
gccttcgccg accggtacac caacgccacc atcggcgcgc tcaccttcca tggcgaggac   240
atggcgttcg cgccctacgg cgagcggtgg cgccagctcc gcaagatctg cgtgctggag   300
ctgctcagcg ccgcccgggt gcagtcgttc cgccacatcc gggcggagga ggtgtcgcgg   360
ctcgtcggga aactcgccgc gtccgccgcc gccggcgaag ctgtccacct caacaagatt   420
gtcgcgaagt tcgtcaacga caccatcgtg agggaggcgg tcggcagcgg gagcaagcac   480
caggacgagt acctcaactc catcgacgta gccctccggc agacaatggg ggtcgccctc   540
gccgacctct ccccgtcttc gaggctcata cagatgattg acacggcacc ccggaaggtg   600
ctcgcggccc ggaacaacat ggagcgcatc ctcgaggaaa tcatcaacga gaccaaggaa   660
gccatggacc gcggcgacgg ccagaagaag gtggagggca tcctcggtgt cctgctgagg   720
ctccagaagg aaggcagcac gccggtcccg ctcaccaacg aggtcatcgt tacggtgatg   780
tttgacatgt ttggcgctgg cagcgacacc tcgtcgacct tgctgacctg gtgcatgatg   840
gagctagtcc ggtcaccgcc gacgatggcc aaagtgcaag acgaggtgcg agaggccttc   900
aaagggaaga aggagagcac catcatcact gaagacgacc tcaaggggct cacctacctc   960
aagcaagtga tcaaggaggc cctgaggatg caccctccgg tgccctcct gcttccaagg  1020
aagtgtcgcg agacgtgcaa ggtcatgggc tacgacattc ccaagggcac ggtagtgttc  1080
gctaacgcat gggcaatcgg cagggatccc aagtattggg aggatccaga ggagttcaag  1140
ccagagcgat tcgacaagag caatgtggac tacaagggaa caaactttga gtacctgccg  1200
tttggatctg gccgtcggat ttgtcccggc ataaacctag gcttgtgcaa cattgagctc  1260
gcgttggcga gccttctata tcactttgac tggaagctgc cgaacggaat ggagcccaaa  1320
gacatagata tgggagaggc tcaagggtta atcgccagta agaaaacaaa cctaaccctg  1380
caccctgtga ctcgcattgc gccggccggt tttaattaa                         1419
```

<210> SEQ ID NO 4
<211> LENGTH: 1422
<212> TYPE: DNA
<213> ORGANISM: Vetiveria zizanioides

<400> SEQUENCE: 4

```
tggacgctgc cggtgatcgg cagcctccac cacgtgatta cctaccccaa cctccaacgt    60
gcactgcgcg tgctggcgca gaagtacggg ccagtgatga tgttccagct cggcgaggtg   120
ccaatgatgg tggtgtcgtc gccagccgcc gcgcaggagg tcctcaagac gaacgacctc   180
accttcgccg acaggtacac caacgctacc atcggcgcgc tcaccttcca tggcgaggac   240
atggtgttcg cgccctacgg cgagcggtgg cgccagctcc gcaaaatctg catgctagag   300
ctgctcagcg ccgcccgggt tcagtcgttc cgccacatcc gggaggagga ggtggcgcgg   360
cttgtgggga acatcgccac gtctgctgcc gccggcgaag ccgtccacct caacaagatg   420
gtctcgaggt tcgtcaacga caccgtcgtg agggaggcgg tcggcagcgg gagcaagcac   480
caggaagagt acctcagctc cctcaacgta gccctccggc agacaatggg ggtagccgtc   540
gccgacctct ccccgtcttc caggctcatg cagatgattg acacggcacc ccggaaggtg   600
ctcgcagccc ggaacaacat ggtgcgcatc ctcgaggaaa tcatcaagga gaccaaggaa   660
gccatggaat gcggcgacgg ccaggagaag gtggagggca tcctcggtgt gctgctgagg   720
```

```
ctccagaagg aaggcagcac gccggtcccg ctcaccaacg aggtcatcgt tacggtgatg    780
tttgacatgt ttggcgccgg cagcgacacc tcatcgacct tgctgacctg gtgcatgaca    840
gagctagtcc ggtcaccgcc gacaatggcc aaagtgcaag atgaggtgcg acaggccatc    900
aaagggaaga agcagagccc catcgtcatc actgaagacg acctcaaggg gctcacctac    960
ctcaagcaag tgatcaagga gaccctgagg atgcacactc ctttgcccct cctgcttcca   1020
aggaagtgtc gtgagacgtg caaggtcatg ggctacgaca ttcccaaggg cacggtagtg   1080
ttcgctaacg cgtgggcaat ctgcagggat cctaagtatt gggaggattc agaggagttc   1140
aagccagagc gattcgacaa gagcagtttg gactacaagg gaacaaactt tgagtacctg   1200
ccgtttggat ctggccgtcg gatttgtcct ggcataaatc ttgggttggg taacgctgaa   1260
atcgcgctag ccagccttct atatcacttt gactggaagc tacctgatgg aatgcaaccc   1320
aaggacgtaa atatggaaga ggctcaaggg ttagtcgcca gtaagaaaac aaacttaacc   1380
ctgtaccctg ttactcgcat tgcgccggcc ggtttttaatt aa                     1422
```

```
<210> SEQ ID NO 5
<211> LENGTH: 29
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 5
ggcccggtga tgcacgtgca rytnggnga                                       29

<210> SEQ ID NO 6
<211> LENGTH: 29
<212> TYPE: DNA
<213> ORGANISM: Artificial sequence
<220> FEATURE:
<223> OTHER INFORMATION: Syntehtic primer
<220> FEATURE:
<221> NAME/KEY: misc_feature
<222> LOCATION: (21)..(21)
<223> OTHER INFORMATION: n is a, c, g, or t

<400> SEQUENCE: 6
ccgtacagcg accactggmr ncaratgmg                                       29

<210> SEQ ID NO 7
<211> LENGTH: 28
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 7
```

```
gctccatgac ctgccggdsn gcnttygg                                           28

<210> SEQ ID NO 8
<211> LENGTH: 26
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 8
cannanttyc tctggtacgc ctacgt                                             26

<210> SEQ ID NO 9
<211> LENGTH: 24
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 9
ctytgndank cctacgtggg cggc                                               24

<210> SEQ ID NO 10
<211> LENGTH: 27
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 10
aarccnranc ggttgcagat ggagggc                                            27

<210> SEQ ID NO 11
<211> LENGTH: 26
<212> TYPE: DNA
<213> ORGANISM: Artificial sequence
<220> FEATURE:
<223> OTHER INFORMATION: Synthetic primer

<400> SEQUENCE: 11
gtraarctra ccttygacgg cttccc                                             26

<210> SEQ ID NO 12
<211> LENGTH: 1164
<212> TYPE: DNA
<213> ORGANISM: Vetiveria zizanioides
```

<400> SEQUENCE: 12

```
ccaatgatgg tggtgtcgtc gccagccgct gcgaaggggg tcctcaagac gaacgacatc    60
accttcgccg acaggtacac caacgccacc atcggcgcgc tcaccttcca tggcgaggac   120
atggtgttcg tgcccctacgg cgagcggtgg cgccagctcc gcaaaatcta catgctggag   180
ctgctcagcg ccgcccgggt tcagtcattc cgccacatcc gggaggagga ggtggcgcgg   240
cttgtgggga acatcgccac gtctgctgcc gccggcgaag ccatccacct caacaagatg   300
gtctcgaggt tcgtcaacga caccgtcgtg acggaggcgg tcggcagcgg gagcaagcac   360
caggaagagt acctcagctc cctcgacgta gccctccggc agacaatggg ggtagccgtc   420
gccgacctct tcccgtcttc caagctcatg cagatgattg acacggcacc ccggaaggtg   480
ctcgcagccc ggaacaacat ggtgcgcatc ctcgaggaaa tcatcaagga gaccaaggaa   540
gccatggaat gcggcgacgg ccaggagaag gtggagggca tcctcggtgt gctgctgagg   600
ctccagaagg aaggcagcac gccggtcccg ctcaccaacg aggtcatcgt tacggtgatg   660
tttgacatgt ttggcgccgg cagcgacacc tcatcgacct tgctgacctg gtgcatgaca   720
gagctagtcc ggtcaccgcc gacaatggcc aaagtgcaag atgaggtgcg acaggccatc   780
aaagggaaga agcagagccc catcgtcatc actgaagacg acctcaaggg gctcacctac   840
ctcaagcaag tgatcaagga gaccctgagg atgcacactc ctttgccccct cctgcttcca   900
aggaagtgtc gtgagacgtg caaggtcatg ggctacgaca ttcccaaggg cacggtagtg   960
ttcgctaacg cgtgggcaat ctgcagggat cctaagtatt gggaggattc agaggagttc  1020
aagccagagc gattcgacaa gagcagtttg gactacaagg gaacaaactt tgagtacctg  1080
ccgtttggat ctggccgtcg gatttgtcct ggcataaatc ttgggttggg taacgctgaa  1140
atcgcgctag ccagccttct atat                                         1164
```

<210> SEQ ID NO 13
<211> LENGTH: 25
<212> TYPE: DNA
<213> ORGANISM: Artificial sequence
<220> FEATURE:
<223> OTHER INFORMATION: Synthetic primer

<400> SEQUENCE: 13

```
gctaacgcgt gggcaatctg caggg                                          25
```

<210> SEQ ID NO 14
<211> LENGTH: 28
<212> TYPE: DNA
<213> ORGANISM: Artificial sequence
<220> FEATURE:
<223> OTHER INFORMATION: Synthetic primer

<400> SEQUENCE: 14

```
gttcaagcca gagcgattcg acaagagc                                       28
```

<210> SEQ ID NO 15
<211> LENGTH: 23
<212> TYPE: DNA
<213> ORGANISM: Artificial sequence
<220> FEATURE:
<223> OTHER INFORMATION: Synthetic primer

<400> SEQUENCE: 15

```
gactgaacccc gggcggcgct gag                                           23
```

<210> SEQ ID NO 16
<211> LENGTH: 26
<212> TYPE: DNA
<213> ORGANISM: Artificial sequence
<220> FEATURE:
<223> OTHER INFORMATION: Synthetic primer

<400> SEQUENCE: 16
cgaacaccat gtcctcgcca tggaag                                         26

<210> SEQ ID NO 17
<211> LENGTH: 500
<212> TYPE: DNA
<213> ORGANISM: Vetiveria zizanioides

<400> SEQUENCE: 17
atcctaagta ttgggaggat tcagaggagt tcaagccaga gcgattcgac aagagcagtt    60
tggactacaa gggaacaaac tttgagtacc tgccgtttgg atctggccgt cggatttgtc   120
ctggcataaa tcttgggttg ggtaacgctg aaatcgcgct agccagcctt ctatatcact   180
ttgactggaa gctgcctgat ggaatggaac ccaaggacgt aaatatgaaa gaggctcaag   240
ggttagtcgc cagtaagaaa acaaacttaa ccctgtaccc tgttactcgc attgcgccgg   300
ccggttttaa ttaatgcgaa ataaggcgg ctggctgggc acaataatgt ggtgcgcgaa    360
ctagtatgca actagtactg gatagatgga aaatactgta agtggcagga tcggaatgat   420
gaattgatac gtatatatgc caactatgta ttccggctag ctgccatata ttttgtaaaa   480
aaaaaaaaaa aaaaaaaaaa                                              500

<210> SEQ ID NO 18
<211> LENGTH: 426
<212> TYPE: DNA
<213> ORGANISM: Vetiveria zizanioides

<400> SEQUENCE: 18
tagaattcag cggccgctga attctacaca tccaatctca aagataatct agcagggaaa    60
gggaacttgc cactccacta tggaggacac taagatcctc gtcgccgtgg tgtccgtgtg   120
cgtgcttgtt gtggtcctct ccaagctcaa gaagtccctg ctgctcggcg cgaaaccgaa   180
gcttaacctg cccccagggc catggacgct gccggtgatc ggcagcctcc accacgtgat   240
tacctacccc aacctccaac gtgcactgcg cgtgctggcg cagaagtacg ggccagtgat   300
gatgttccag ctcggcgagg tgccaatgat ggtggtgtcg tcgccagccg ccgcgcagga   360
ggtcctcaag acgaacgacc tcaccttcgc cgacaggtac accaacgcta ccatcggcgc   420
gctcac                                                             426

<210> SEQ ID NO 19
<211> LENGTH: 27
<212> TYPE: DNA
<213> ORGANISM: Artificial sequence
<220> FEATURE:
<223> OTHER INFORMATION: Synthetic primer

<400> SEQUENCE: 19
atggaggata ctaagatcct cgtcgcc                                        27

<210> SEQ ID NO 20
<211> LENGTH: 26
<212> TYPE: DNA
<213> ORGANISM: Artificial sequence

```
<220> FEATURE:
<223> OTHER INFORMATION: Synthetic primer

<400> SEQUENCE: 20
attaattaaa accggccggc gcaatg                                          26

<210> SEQ ID NO 21
<211> LENGTH: 1542
<212> TYPE: DNA
<213> ORGANISM: Vetiveria zizanioides

<400> SEQUENCE: 21
atggaggata ctaagatcct cgtcgccgcg gtgtccgtgt gcgtgcttct tgtggtcctc      60
tccaagctca agaagtccct gctgcccggc gcgaaaccaa agcttaacct gccccaggg     120 ccatggacgc tgccggtgat cggcagcctc caccacgtga tcacctaccc caacctccac     180
cgcgcactgc acgggctggc gcagaagtac ggtccggtga tgatgttccg gctcggcgag     240
gtgccaatga tggtggtgtc gtcgccggcg gccgcgcagg aggccctcaa gacgaacgac     300
atcgccttcg ccgaccggta caccaacgcc accatcggcg cgctcacctt ccatggcgag     360
gacatggcgt tcgcgcccta cggcgagcgg tggcgccagc tccgcaagat ctgcgtgctg     420
gagctgctca gcgccgcccg ggtgcagtcg ttccgccaca tccgggcgga ggaggtgtcg     480
cggctcgtcg ggaaactcgc gcgtccgcc gccgccggcg aagctgtcca cctcaacaag      540
attgtcgcga agttcgtcaa cgacaccatc gtgagggagg cggtcggcag cgggagcaag     600
caccaggacg agtacctcaa ctccatcgac gtagccctcc ggcagacaat ggggtcgcc      660 ctcgccgacc tcttcccgtc ttcgaggctc atacagatga ttgacacggc accccggaag     720
gtgctcgcgg cccggaacaa catggagcgc atcctcgagg aaatcatcaa cgagaccaag     780
gaagccatgg accgcggcga cggccagaag aaggtggagg gcatcctcgg tgtcctgctg     840
aggctccaga aggaaggcag cacgccggtc ccgctcacca acgaggtcat cgttacggtg     900
atgtttgaca tgtttggcgc tggcagcgac acctcgtcga ccttgctgac ctggtgcatg     960
atggagctag tccggtcacc gccgacgatg gccaaagtgc aagacgaggt gcgagaggcc    1020
ttcaaaggga agaaggagag caccatcatc actgaagacg acctcaaggg gctcacctac    1080
ctcaagcaag tgatcaagga ggccctgagg atgcaccctc cggtgcccct cctgcttcca    1140
aggaagtgtc gcgagacgtg caaggtcatg ggctacgaca ttcccaaggg cacggtagtg    1200
ttcgctaacg catgggcaat cggcagggat cccaagtatt gggaggatcc agaggagttc    1260
aagccagagc gattcgacaa gagcaatgtg gactacaagg gaacaaactt tgagtacctg    1320
ccgtttggat ctggccgtcg gatttgtccc ggcataaacc taggcttgtg caacattgag    1380
ctcgcgttgg cgagccttct atatcacttt gactggaagc tgccgaacgg aatggagccc    1440
aaagacatag atatgggaga ggctcaaggg ttaatcgcca gtaagaaaac aaacctaacc    1500
ctgcaccctg tgactcgcat tgcgccggcc ggttttaatt aa                       1542

<210> SEQ ID NO 22
<211> LENGTH: 1545
<212> TYPE: DNA
<213> ORGANISM: Vetiveria zizanioides

<400> SEQUENCE: 22
atggaggata ctaagatcct cgtcgccgtg gtgtccgtgt gcgtgcttgt tgtggtcctc      60 tcca

```
ccatggacgc tgccggtgat cggcagcctc caccacgtga ttacctaccc caacctccaa      180
cgtgcactgc gcgtgctggc gcagaagtac gggccagtga tgatgttcca gctcggcgag      240
gtgccaatga tggtggtgtc gtcgccagcc gccgcgcagg aggtcctcaa gacgaacgac      300
ctcaccttcg ccgacaggta caccaacgct accatcggcg cgctcacctt ccatggcgag      360
gacatggtgt tcgcgcccta cggcgagcgg tggcgccagc tccgcaaaat ctgcatgcta      420
gagctgctca gcgccgcccg ggttcagtcg ttccgccaca tccgggagga ggaggtggcg      480
cggcttgtgg ggaacatcgc cacgtctgct gccgccggcg aagccgtcca cctcaacaag      540
atggtctcga ggttcgtcaa cgacaccgtc gtgagggagg cggtcggcag cgggagcaag      600
caccaggaag agtacctcag ctccctcaac gtagccctcc ggcagacaat ggggg tagcc      660
gtcgccgacc tcttcccgtc ttccaggctc atgcagatga ttgacacggc accccggaag      720
gtgctcgcag cccggaacaa catggtgcgc atcctcgagg aaatcatcaa ggagaccaag      780
gaagccatgg aatgcggcga cggccaggag aaggtggagg gcatcctcgg tgtgctgctg      840
aggctccaga aggaaggcag cacgccggtc ccgctcacca acgaggtcat cgttacggtg      900
atgtttgaca tgtttggcgc cggcagcgac acctcatcga ccttgctgac ctggtgcatg      960
acagagctag tccggtcacc gccgacaatg gccaaagtgc aagatgaggt gcgacaggcc     1020
atcaaaggga gaagcagag ccccatcgtc atcactgaag acgacctcaa ggggctcacc     1080
tacctcaagc aagtgatcaa ggagaccctg aggatgcaca ctcctttgcc cctcctgctt     1140
ccaaggaagt gtcgtgagac gtgcaaggtc atgggctacg acattcccaa gggcacggta     1200
gtgttcgcta acgcgtgggc aatctgcagg gatcctaagt attgggagga ttcagaggag     1260
ttcaagccag agcgattcga caagagcagt ttggactaca agggaacaaa ctttgagtac     1320
ctgccgtttg gatctggccg tcggatttgt cctggcataa atcttgggtt gggtaacgct     1380
gaaatcgcgc tagccagcct tctatatcac tttgactgga agctacctga tggaatggaa     1440
cccaaggacg taaatatgga agaggctcaa gggttagtcg ccagtaagaa aacaaactta     1500
accctgtacc ctgttactcg cattgcgccg ccggttttta attaa                     1545
```

<210> SEQ ID NO 23
<211> LENGTH: 513
<212> TYPE: PRT
<213> ORGANISM: Vetiveria zizanioides

<400> SEQUENCE: 23

```
Met Glu Asp Thr Lys Ile Leu Val Ala Ala Val Ser Val Cys Val Leu
1               5                   10                  15

Leu Val Val Leu Ser Lys Leu Lys Ser Leu Leu Pro Gly Ala Lys
            20                  25                  30

Pro Lys Leu Asn Leu Pro Pro Gly Pro Trp Thr Leu Pro Val Ile Gly
        35                  40                  45

Ser Leu His His Val Ile Thr Tyr Pro Asn Leu Gln Arg Ala Leu His
    50                  55                  60

Gly Leu Ala Gln Lys Tyr Gly Pro Val Met Met Phe Arg Leu Gly Glu
65                  70                  75                  80

Val Pro Met Met Val Val Ser Ser Pro Ala Ala Gln Glu Ala Leu
                85                  90                  95

Lys Thr Asn Asp Ile Ala Phe Ala Asp Arg Tyr Thr Asn Ala Thr Ile
            100                 105                 110

Gly Ala Leu Thr Phe His Gly Glu Asp Met Ala Phe Ala Pro Tyr Gly
        115                 120                 125
```

Glu Arg Trp Arg Gln Leu Arg Lys Ile Cys Val Leu Glu Leu Leu Ser
130                 135                 140

Ala Ala Arg Val Gln Ser Phe Arg His Ile Arg Ala Glu Glu Val Ser
145                 150                 155                 160

Arg Leu Val Gly Lys Leu Ala Ser Ala Ala Gly Glu Ala Val
                165                 170                 175

His Leu Asn Lys Ile Val Ala Lys Phe Val Asn Asp Thr Ile Val Arg
                180                 185                 190

Glu Ala Val Gly Ser Gly Ser Lys His Gln Asp Glu Tyr Leu Asn Ser
            195                 200                 205

Ile Asp Val Ala Leu Arg Gln Thr Met Gly Val Ala Leu Ala Asp Leu
210                 215                 220

Phe Pro Ser Ser Arg Leu Ile Gln Met Ile Asp Thr Ala Pro Arg Lys
225                 230                 235                 240

Val Leu Ala Ala Arg Asn Asn Met Glu Arg Ile Leu Glu Glu Ile Ile
                245                 250                 255

Asn Glu Thr Lys Glu Ala Met Asp Arg Gly Asp Gly Gln Lys Lys Val
            260                 265                 270

Glu Gly Ile Leu Gly Val Leu Leu Arg Leu Gln Lys Glu Gly Ser Thr
            275                 280                 285

Pro Val Pro Leu Thr Asn Glu Val Ile Val Thr Val Met Phe Asp Met
290                 295                 300

Phe Gly Ala Gly Ser Asp Thr Ser Ser Thr Leu Leu Thr Trp Cys Met
305                 310                 315                 320

Met Glu Leu Val Arg Ser Pro Pro Thr Met Ala Lys Val Gln Asp Glu
                325                 330                 335

Val Arg Glu Ala Phe Lys Gly Lys Lys Glu Ser Thr Ile Ile Thr Glu
            340                 345                 350

Asp Asp Leu Lys Gly Leu Thr Tyr Leu Lys Gln Val Ile Lys Glu Ala
            355                 360                 365

Leu Arg Met His Pro Pro Val Pro Leu Leu Leu Pro Arg Lys Cys Arg
370                 375                 380

Glu Thr Cys Lys Val Met Gly Tyr Asp Ile Pro Lys Gly Thr Val Val
385                 390                 395                 400

Phe Ala Asn Ala Trp Ala Ile Gly Arg Asp Pro Lys Tyr Trp Glu Asp
                405                 410                 415

Pro Glu Glu Phe Lys Pro Glu Arg Phe Asp Lys Ser Asn Val Asp Tyr
            420                 425                 430

Lys Gly Thr Asn Phe Glu Tyr Leu Pro Phe Gly Ser Gly Arg Arg Ile
            435                 440                 445

Cys Pro Gly Ile Asn Leu Gly Leu Cys Asn Ile Glu Leu Ala Leu Ala
450                 455                 460

Ser Leu Leu Tyr His Phe Asp Trp Lys Leu Pro Asn Gly Met Glu Pro
465                 470                 475                 480

Lys Asp Ile Asp Met Gly Glu Ala Gln Gly Leu Ile Ala Ser Lys Lys
                485                 490                 495

Thr Asn Leu Thr Leu His Pro Val Thr Arg Ile Ala Pro Ala Gly Phe
            500                 505                 510

Asn

<210> SEQ ID NO 24
<211> LENGTH: 514
<212> TYPE: PRT

<213> ORGANISM: Vetiveria zizanioides

<400> SEQUENCE: 24

```
Met Glu Asp Thr Lys Ile Leu Val Ala Val Val Ser Val Cys Val Leu
1               5                   10                  15

Val Val Val Leu Ser Lys Leu Lys Lys Ser Leu Leu Leu Gly Ala Lys
                20                  25                  30

Pro Lys Leu Asn Leu Pro Pro Gly Pro Trp Thr Leu Pro Val Ile Gly
            35                  40                  45

Ser Leu His His Val Ile Thr Tyr Pro Asn Leu Gln Arg Ala Leu Arg
        50                  55                  60

Val Leu Ala Gln Lys Tyr Gly Pro Val Met Met Phe Gln Leu Gly Glu
65                  70                  75                  80

Val Pro Met Met Val Ser Ser Pro Ala Ala Gln Glu Val Leu
                85                  90                  95

Lys Thr Asn Asp Leu Thr Phe Ala Asp Arg Tyr Thr Asn Ala Thr Ile
                100                 105                 110

Gly Ala Leu Thr Phe His Gly Glu Asp Met Val Phe Ala Pro Tyr Gly
            115                 120                 125

Glu Arg Trp Arg Gln Leu Arg Lys Ile Cys Met Leu Glu Leu Leu Ser
    130                 135                 140

Ala Ala Arg Val Gln Ser Phe Arg His Ile Arg Glu Glu Val Ala
145                 150                 155                 160

Arg Leu Val Gly Asn Ile Ala Thr Ser Ala Ala Ala Gly Glu Ala Val
                165                 170                 175

His Leu Asn Lys Met Val Ser Arg Phe Val Asn Asp Thr Val Val Arg
            180                 185                 190

Glu Ala Val Gly Ser Gly Ser Lys His Gln Glu Glu Tyr Leu Ser Ser
        195                 200                 205

Leu Asn Val Ala Leu Arg Gln Thr Met Gly Val Ala Val Ala Asp Leu
210                 215                 220

Phe Pro Ser Ser Arg Leu Met Gln Met Ile Asp Thr Ala Pro Arg Lys
225                 230                 235                 240

Val Leu Ala Ala Arg Asn Asn Met Val Arg Ile Leu Glu Glu Ile Ile
                245                 250                 255

Lys Glu Thr Lys Glu Ala Met Glu Cys Gly Asp Gly Gln Glu Lys Val
            260                 265                 270

Glu Gly Ile Leu Gly Val Leu Leu Arg Leu Gln Lys Glu Gly Ser Thr
        275                 280                 285

Pro Val Pro Leu Thr Asn Glu Val Ile Val Thr Val Met Phe Asp Met
    290                 295                 300

Phe Gly Ala Gly Ser Asp Thr Ser Ser Thr Leu Leu Thr Trp Cys Met
305                 310                 315                 320

Thr Glu Leu Val Arg Ser Pro Pro Thr Met Ala Lys Val Gln Asp Glu
                325                 330                 335

Val Arg Gln Ala Ile Lys Gly Lys Lys Gln Ser Pro Ile Val Ile Thr
            340                 345                 350

Glu Asp Asp Leu Lys Gly Leu Thr Tyr Leu Lys Gln Val Ile Lys Glu
        355                 360                 365

Thr Leu Arg Met His Thr Pro Leu Pro Leu Leu Pro Arg Lys Cys
    370                 375                 380

Arg Glu Thr Cys Lys Val Met Gly Tyr Asp Ile Pro Lys Gly Thr Val
385                 390                 395                 400
```

```
Val Phe Ala Asn Ala Trp Ala Ile Cys Arg Asp Pro Lys Tyr Trp Glu
            405                 410                 415

Asp Ser Glu Glu Phe Lys Pro Glu Arg Phe Asp Lys Ser Ser Leu Asp
        420                 425                 430

Tyr Lys Gly Thr Asn Phe Glu Tyr Leu Pro Phe Gly Ser Gly Arg Arg
        435                 440                 445

Ile Cys Pro Gly Ile Asn Leu Gly Leu Gly Asn Ala Glu Ile Ala Leu
    450                 455                 460

Ala Ser Leu Leu Tyr His Phe Asp Trp Lys Leu Pro Asp Gly Met Glu
465                 470                 475                 480

Pro Lys Asp Val Asn Met Glu Glu Ala Gln Gly Leu Val Ala Ser Lys
                485                 490                 495

Lys Thr Asn Leu Thr Leu Tyr Pro Val Thr Arg Ile Ala Pro Ala Gly
            500                 505                 510

Phe Asn

<210> SEQ ID NO 25
<211> LENGTH: 28
<212> TYPE: DNA
<213> ORGANISM: Artificial sequence
<220> FEATURE:
<223> OTHER INFORMATION: Synthetic primer

<400> SEQUENCE: 25
tactgacata tggctctgtt attagcag                                        28

<210> SEQ ID NO 26
<211> LENGTH: 36
<212> TYPE: DNA
<213> ORGANISM: Artificial sequence
<220> FEATURE:
<223> OTHER INFORMATION: Synthetic primer

<400> SEQUENCE: 26
ggcagcgtcc atgggcccgg ggggaacttc ccttgg                               36

<210> SEQ ID NO 27
<211> LENGTH: 42
<212> TYPE: DNA
<213> ORGANISM: Artificial sequence
<220> FEATURE:
<223> OTHER INFORMATION: Synthetic primer

<400> SEQUENCE: 27
gaagttcccc ccgggcccat ggacgctgcc ggtgatcggc ag                        42

<210> SEQ ID NO 28
<211> LENGTH: 39
<212> TYPE: DNA
<213> ORGANISM: Artificial sequence
<220> FEATURE:
<223> OTHER INFORMATION: Synthetic primer

<400> SEQUENCE: 28
aaagaaaagc ttaattaaaa ccggccggcg caatgcgag                            39

<210> SEQ ID NO 29
<211> LENGTH: 2039
<212> TYPE: DNA
<213> ORGANISM: Artificial sequence
<220> FEATURE:
<223> OTHER INFORMATION: Synthetic cDNA encoding truncated ATR1
```

<400> SEQUENCE: 29

| | | | | | |
|---|---|---|---|---|---|
| ccatgggcac | ggatagcctg | agcgacgacg | tagtactggt | catcgccacg | accagcctgg | 60 |
| cgctggtggc | aggttttgtc | gtcctgctgt | ggaaaaagac | gaccgccgat | cgtagcggtg | 120 |
| agctgaaacc | gttgatgatc | ccgaagtctt | tgatggcaaa | agacgaggat | gacgatctgg | 180 |
| atctgggtag | cggtaaaacg | cgtgtcagca | ttttcttcgg | tactcagacg | ggcacggcgg | 240 |
| agggttttgc | caaggcgctg | agcgaagaga | ttaaagcacg | ctatgaaaaa | gcggcggtta | 300 |
| aagtgatcga | tctggatgac | tacgcggcag | acgacgatca | gtacgaagaa | aagctgaaga | 360 |
| aagaaaccct | ggcattcttc | tgcgttgcga | cctatggtga | cggtgaaccg | accgacaatg | 420 |
| ctgcccgctt | ttacaagtgg | ttcacggaag | agaatgaacg | tgacattaaa | ctgcagcaat | 480 |
| tggcgtacgg | tgtgtttgcg | ctgggcaacc | gtcaatatga | acacttcaat | aagattggta | 540 |
| ttgttctgga | cgaagagttg | tgtaagaagg | gcgctaagcg | cctgatcgag | gttggtttgg | 600 |
| gtgatgatga | ccaatccatc | gaagatgact | tcaacgcttg | gaaagagtcc | ttgtggagcg | 660 |
| aactggataa | actgctgaag | gacgaggacg | ataaaagcgt | cgcgaccccg | tacaccgccg | 720 |
| ttattccgga | gtatcgtgtc | gtcacccacg | acccgcgttt | tactacgcaa | aagtcgatgg | 780 |
| agagcaatgt | ggcgaatggt | aacaccacca | tcgacatcca | tcatccgtgt | cgtgttgatg | 840 |
| tggccgtgca | aaaagaactg | catactcatg | agagcgaccg | cagctgtatc | cacctggagt | 900 |
| ttgatattag | ccgcacgggc | atcacctatg | aaaccggcga | tcatgttggt | gtctacgcgg | 960 |
| agaatcacgt | cgagattgtg | aagaggcgg | gcaagctgct | gggccactcg | ctggatctgg | 1020 |
| ttttcagcat | tcatgcggat | aaagaggacg | gtagccctct | ggaaagcgct | gtgccacctc | 1080 |
| cgttcccagg | cccgtgcacc | ctgggcaccg | gtctggcgcg | ttatgcggac | ctgctgaacc | 1140 |
| cgccacgtaa | gagcgcgctg | gttgcgctgg | cggcgtatgc | gaccgagccg | tctgaggcag | 1200 |
| agaaactgaa | acacctgacc | agcccggatg | gtaaggacga | gtacagccag | tggattgtgg | 1260 |
| cgtcccaacg | tagcctgctg | gaagtcatgg | cagccttccc | gtccgctaaa | ccgccgctgg | 1320 |
| gcgtgttttt | cgcagcaatt | gctccgcgcc | tgcaaccgcg | ttattacagc | atcagcagca | 1380 |
| gcccgcgtct | ggcaccgagc | cgcgtgcacg | ttacgtctgc | actggtctac | ggtccgaccc | 1440 |
| cgaccggccg | tattcacaag | ggtgtgtgtt | ctacttggat | gaaaaacgcg | gttccggccg | 1500 |
| aaaagtccca | cgaatgcagc | ggtgccccga | tctttattcg | tgcgagcaat | ttcaagttgc | 1560 |
| cttccaatcc | gagcacccg | atcgtcatgg | ttggtccggg | tacgggcctg | cgcgccgtttc | 1620 |
| gcggtttcct | gcaggagcgt | atggcactga | aagaggatgg | cgaagagctg | ggtagcagct | 1680 |
| tgctgttttt | cggttgccgc | aaccgtcaga | tggatttcat | ctacgaggac | gagttgaaca | 1740 |
| actttgtgga | ccaaggtgtt | atcagcgaac | tgatcatggc | gttttctcgc | gaaggtgcac | 1800 |
| agaaagagta | cgttcagcac | aaaatgatgg | agaaggcagc | acaggtgtgg | gatttgatta | 1860 |
| aagaagaagg | ctacctgtac | gtgtgcggcg | acgccaaggg | tatggcccgt | gacgtgcacc | 1920 |
| gtacgctgca | taccatcgtt | caggagcaag | agggcgttag | ctccagcgag | gcggaggcaa | 1980 |
| ttgttaagaa | actgcagacc | gagggccgct | atctgcgtga | cgtctggtaa | tgaggatcc | 2039 |

<210> SEQ ID NO 30
<211> LENGTH: 31
<212> TYPE: DNA
<213> ORGANISM: Artificial sequence
<220> FEATURE:
<223> OTHER INFORMATION: Synthetic spacer

<400> SEQUENCE: 30

```
agctgtcgac taactttaag aaggagatat a                              31
```

<210> SEQ ID NO 31
<211> LENGTH: 67
<212> TYPE: DNA
<213> ORGANISM: Artificial sequence
<220> FEATURE:
<223> OTHER INFORMATION: Synthetic primer

<400> SEQUENCE: 31

```
ggttttaatt aagctgtcga ctaactttaa gaaggagata tatccatggg cacggatagc    60
ctgagcg                                                               67
```

<210> SEQ ID NO 32
<211> LENGTH: 55
<212> TYPE: DNA
<213> ORGANISM: Artificial sequence
<220> FEATURE:
<223> OTHER INFORMATION: Synthetic primer

<400> SEQUENCE: 32

```
tatcatcgat aagctgaatt cttaagcttc attaccagac gtcacgcaga tagcg          55
```

<210> SEQ ID NO 33
<211> LENGTH: 49
<212> TYPE: DNA
<213> ORGANISM: Artificial sequence
<220> FEATURE:
<223> OTHER INFORMATION: Synthetic primer

<400> SEQUENCE: 33

```
tctggtaatg aagcttaaga aggagatata aatatggcta ctacggctg                 49
```

<210> SEQ ID NO 34
<211> LENGTH: 47
<212> TYPE: DNA
<213> ORGANISM: Artificial sequence
<220> FEATURE:
<223> OTHER INFORMATION: Synthetic primer

<400> SEQUENCE: 34

```
tcgataagct gaattctcat taaaccggaa tcaggttgac atacaag                   47
```

<210> SEQ ID NO 35
<211> LENGTH: 513
<212> TYPE: PRT
<213> ORGANISM: Artificial sequence
<220> FEATURE:
<223> OTHER INFORMATION: Synthetic recombinant VzP521-11-1 protein

<400> SEQUENCE: 35

Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Thr Leu Pro Val Ile Gly
        35                  40                  45

Ser Leu His His Val Ile Thr Tyr Pro Asn Leu Gln Arg Ala Leu His
    50                  55                  60

Gly Leu Ala Gln Lys Tyr Gly Pro Val Met Met Phe Arg Leu Gly Glu
65                  70                  75                  80

Val Pro Met Met Val Val Ser Ser Pro Ala Ala Ala Gln Glu Ala Leu

```
            85                  90                  95
Lys Thr Asn Asp Ile Ala Phe Ala Asp Arg Tyr Thr Asn Ala Thr Ile
            100                 105                 110

Gly Ala Leu Thr Phe His Gly Glu Asp Met Ala Phe Ala Pro Tyr Gly
            115                 120                 125

Glu Arg Trp Arg Gln Leu Arg Lys Ile Cys Val Leu Glu Leu Leu Ser
        130                 135                 140

Ala Ala Arg Val Gln Ser Phe Arg His Ile Arg Ala Glu Glu Val Ser
145                 150                 155                 160

Arg Leu Val Gly Lys Leu Ala Ala Ser Ala Ala Gly Glu Ala Val
                165                 170                 175

His Leu Asn Lys Ile Val Ala Lys Phe Val Asn Asp Thr Ile Val Arg
            180                 185                 190

Glu Ala Val Gly Ser Gly Ser Lys His Gln Asp Glu Tyr Leu Asn Ser
            195                 200                 205

Ile Asp Val Ala Leu Arg Gln Thr Met Gly Val Ala Leu Ala Asp Leu
        210                 215                 220

Phe Pro Ser Ser Arg Leu Ile Gln Met Ile Asp Thr Ala Pro Arg Lys
225                 230                 235                 240

Val Leu Ala Ala Arg Asn Asn Met Glu Arg Ile Leu Glu Glu Ile Ile
                245                 250                 255

Asn Glu Thr Lys Glu Ala Met Asp Arg Gly Asp Gly Gln Lys Lys Val
            260                 265                 270

Glu Gly Ile Leu Gly Val Leu Leu Arg Leu Gln Lys Glu Gly Ser Thr
        275                 280                 285

Pro Val Pro Leu Thr Asn Glu Val Ile Val Thr Val Met Phe Asp Met
290                 295                 300

Phe Gly Ala Gly Ser Asp Thr Ser Ser Thr Leu Leu Trp Cys Met
305                 310                 315                 320

Met Glu Leu Val Arg Ser Pro Pro Thr Met Ala Lys Val Gln Asp Glu
                325                 330                 335

Val Arg Glu Ala Phe Lys Gly Lys Lys Glu Ser Thr Ile Ile Thr Glu
            340                 345                 350

Asp Asp Leu Lys Gly Leu Thr Tyr Leu Lys Gln Val Ile Lys Glu Ala
        355                 360                 365

Leu Arg Met His Pro Pro Val Pro Leu Leu Pro Arg Lys Cys Arg
        370                 375                 380

Glu Thr Cys Lys Val Met Gly Tyr Asp Ile Pro Lys Gly Thr Val Val
385                 390                 395                 400

Phe Ala Asn Ala Trp Ala Ile Gly Arg Asp Pro Lys Tyr Trp Glu Asp
                405                 410                 415

Pro Glu Glu Phe Lys Pro Glu Arg Phe Asp Lys Ser Asn Val Asp Tyr
            420                 425                 430

Lys Gly Thr Asn Phe Glu Tyr Leu Pro Phe Gly Ser Gly Arg Arg Ile
        435                 440                 445

Cys Pro Gly Ile Asn Leu Gly Leu Cys Asn Ile Glu Leu Ala Leu Ala
        450                 455                 460

Ser Leu Leu Tyr His Phe Asp Trp Lys Leu Pro Asn Gly Met Glu Pro
465                 470                 475                 480

Lys Asp Ile Asp Met Gly Glu Ala Gln Gly Leu Ile Ala Ser Lys Lys
                485                 490                 495

Thr Asn Leu Thr Leu His Pro Val Thr Arg Ile Ala Pro Ala Gly Phe
            500                 505                 510
```

Asn

<210> SEQ ID NO 36
<211> LENGTH: 514
<212> TYPE: PRT
<213> ORGANISM: Artificial sequence
<220> FEATURE:
<223> OTHER INFORMATION: Synthetic recombinant VzP521-16-1 protein

<400> SEQUENCE: 36

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Thr Leu Pro Val Ile Gly
        35                  40                  45

Ser Leu His His Val Ile Thr Tyr Pro Asn Leu Gln Arg Ala Leu Arg
    50                  55                  60

Val Leu Ala Gln Lys Tyr Gly Pro Val Met Met Phe Gln Leu Gly Glu
65                  70                  75                  80

Val Pro Met Met Val Ser Ser Pro Ala Ala Gln Glu Val Leu
                85                  90                  95

Lys Thr Asn Asp Leu Thr Phe Ala Asp Arg Tyr Thr Asn Ala Thr Ile
            100                 105                 110

Gly Ala Leu Thr Phe His Gly Glu Asp Met Val Phe Ala Pro Tyr Gly
        115                 120                 125

Glu Arg Trp Arg Gln Leu Arg Lys Ile Cys Met Leu Glu Leu Leu Ser
    130                 135                 140

Ala Ala Arg Val Gln Ser Phe Arg His Ile Arg Glu Glu Glu Val Ala
145                 150                 155                 160

Arg Leu Val Gly Asn Ile Ala Thr Ser Ala Ala Ala Gly Glu Ala Val
                165                 170                 175

His Leu Asn Lys Met Val Ser Arg Phe Val Asn Asp Thr Val Val Arg
            180                 185                 190

Glu Ala Val Gly Ser Gly Ser Lys His Gln Glu Glu Tyr Leu Ser Ser
        195                 200                 205

Leu Asn Val Ala Leu Arg Gln Thr Met Gly Val Ala Val Ala Asp Leu
    210                 215                 220

Phe Pro Ser Ser Arg Leu Met Gln Met Ile Asp Thr Ala Pro Arg Lys
225                 230                 235                 240

Val Leu Ala Ala Arg Asn Asn Met Val Arg Ile Leu Glu Glu Ile Ile
                245                 250                 255

Lys Glu Thr Lys Glu Ala Met Glu Cys Gly Asp Gly Gln Glu Lys Val
            260                 265                 270

Glu Gly Ile Leu Gly Val Leu Leu Arg Leu Gln Lys Glu Gly Ser Thr
        275                 280                 285

Pro Val Pro Leu Thr Asn Glu Val Ile Val Thr Val Met Phe Asp Met
    290                 295                 300

Phe Gly Ala Gly Ser Asp Thr Ser Ser Thr Leu Leu Thr Trp Cys Met
305                 310                 315                 320

Thr Glu Leu Val Arg Ser Pro Thr Met Ala Lys Val Gln Asp Glu
                325                 330                 335

Val Arg Gln Ala Ile Lys Gly Lys Lys Gln Ser Pro Ile Val Ile Thr
            340                 345                 350
```

Glu Asp Asp Leu Lys Gly Leu Thr Tyr Leu Lys Gln Val Ile Lys Glu
            355                 360                 365

Thr Leu Arg Met His Thr Pro Leu Pro Leu Leu Pro Arg Lys Cys
370                 375                 380

Arg Glu Thr Cys Lys Val Met Gly Tyr Asp Ile Pro Lys Gly Thr Val
385                 390                 395                 400

Val Phe Ala Asn Ala Trp Ala Ile Cys Arg Asp Pro Lys Tyr Trp Glu
                405                 410                 415

Asp Ser Glu Glu Phe Lys Pro Glu Arg Phe Asp Lys Ser Ser Leu Asp
                420                 425                 430

Tyr Lys Gly Thr Asn Phe Glu Tyr Leu Pro Phe Gly Ser Gly Arg Arg
            435                 440                 445

Ile Cys Pro Gly Ile Asn Leu Gly Leu Gly Asn Ala Glu Ile Ala Leu
450                 455                 460

Ala Ser Leu Leu Tyr His Phe Asp Trp Lys Leu Pro Asp Gly Met Glu
465                 470                 475                 480

Pro Lys Asp Val Asn Met Glu Glu Ala Gln Gly Leu Val Ala Ser Lys
                485                 490                 495

Lys Thr Asn Leu Thr Leu Tyr Pro Val Thr Arg Ile Ala Pro Ala Gly
            500                 505                 510

Phe Asn

<210> SEQ ID NO 37
<211> LENGTH: 1542
<212> TYPE: DNA
<213> ORGANISM: Artificial sequence
<220> FEATURE:
<223> OTHER INFORMATION: Synthetic cDNA encoding vetiver VzP521-11-1

<400> SEQUENCE: 37

```
atggctctgt tattagcagt tttttggtcg gcgcttataa tcctcgtagt aacctacacc      60
atatccctcc taatcaacca atggcgaaaa ccgaaacccc aagggaagtt cccccccggc     120
ccatggacgc tgccggtgat cggcagcctc caccacgtga tcacctaccc caacctccac     180
cgcgcactgc acgggctggc gcagaagtac ggtccggtga tgatgttccg gctcggcgag     240
gtgccaatga tggtggtgtc gtcgccggcg ccgcgcagg aggccctcaa gacgaacgac      300
atcgccttcg ccgaccggta caccaacgcc accatcggcg cgctcacctt ccatggcgag     360
gacatggcgt tcgcgcccta cggcgagcgg tggcgccagc tccgcaagat ctgcgtgctg     420
gagctgctca cgccgcccg ggtgcagtcg ttccgccaca tccgggcgga ggaggtgtcg      480
cggctcgtcg ggaaactcgc cgcgtccgcc gccgcggcg aagctgtcca cctcaacaag      540
attgtcgcga gttcgtcaa cgacaccatc gtgagggagg cggtcggcag cgggagcaag      600
caccaggacg agtacctcaa ctccatcgac gtagccctcc ggcagacaat ggggtcgcc      660
ctcgccgacc tcttcccgtc ttcgaggctc atacagatga ttgacacggc accccggaag     720
gtgctcgcgg cccggaacaa catggagcgc atcctcgagg aaatcatcaa cgagaccaag     780
gaagccatgg accgcggcga cggccagaag aaggtggagg catcctcgg tgtcctgctg      840
aggctccaga aggaaggcag cacgccggtc ccgctcacca acgaggtcat cgttacggtg     900
atgtttgaca tgtttggcgc tggcagcgac acctcgtcga ccttgctgac ctggtgcatg     960
atggagctag tccggtcacc gccgacgatg gccaaagtgc aagacgaggt gcgagaggcc    1020
ttcaaaggga agaggagag caccatcatc actgaagacg acctcaaggg gctcacctac    1080
ctcaagcaag tgatcaagga ggccctgagg atgcaccctc cggtgcccct cctgcttcca    1140
```

```
aggaagtgtc gcgagacgtg caaggtcatg ggctacgaca ttcccaaggg cacggtagtg    1200
ttcgctaacg catgggcaat cggcagggat cccaagtatt gggaggatcc agaggagttc    1260
aagccagagc gattcgacaa gagcaatgtg gactacaagg gaacaaactt tgagtacctg    1320
ccgtttggat ctggccgtcg gatttgtccc ggcataaacc taggcttgtg caacattgag    1380
ctcgcgttgg cgagccttct atatcacttt gactggaagc tgccgaacgg aatggagccc    1440
aaagacatag atatgggaga ggctcaaggg ttaatcgcca gtaagaaaac aaacctaacc    1500
ctgcaccctg tgactcgcat gcgccggcc ggttttaatt aa                        1542
```

<210> SEQ ID NO 38
<211> LENGTH: 1545
<212> TYPE: DNA
<213> ORGANISM: Artificial sequence
<220> FEATURE:
<223> OTHER INFORMATION: Synthetic cDNA encoding vetiver VzP521-16-1

<400> SEQUENCE: 38

```
atggctctgt tattagcagt tttttggtcg gcgcttataa tcctcgtagt aacctacacc     60
atatccctcc taatcaacca atggcgaaaa ccgaaacccc aagggaagtt ccccccgggc    120
ccatggacgc tgccggtgat cggcagcctc caccacgtga ttacctaccc caacctccaa    180
cgtgcactgc gcgtgctggc gcagaagtac gggccagtga tgatgttcca gctcggcgag    240
gtgccaatga tggtggtgtc gtcgccagcc gccgcgcagg aggtcctcaa gacgaacgac    300
ctcaccttcg ccgacaggta caccaacgct accatcggcg cgctcacctt ccatggcgag    360
gacatggtgt tcgcgcccta cggcgagcgg tggcgccagc tccgcaaaat ctgcatgcta    420
gagctgctca gcgccgcccg ggttcagtcg ttccgccaca tccgggagga ggaggtggcg    480
cggcttgtgg ggaacatcgc cacgtctgct gccgccggcg aagccgtcca cctcaacaag    540
atggtctcga ggttcgtcaa cgacaccgtc gtgagggagg cggtcggcag cgggagcaag    600
caccaggaag agtacctcag ctccctcaac gtagccctcc ggcagacaat ggggtagcc     660 gtcgccgacc tcttcccgtc ttccaggctc atgcagatga ttgacacggc accccggaag    720
gtgctcgcag cccggaacaa catggtgcgc atcctcgagg aaatcatcaa ggagaccaag    780
gaagccatgg aatgcggcga cggccaggag aaggtggagg gcatcctcgg tgtgctgctg    840
aggctccaga aggaaggcag cacgccggtc ccgctcacca acgaggtcat cgttacggtg    900
atgtttgaca tgtttggcgc cggcagcgac acctcatcga ccttgctgac ctggtgcatg    960
acagagctag tccggtcacc gccgacaatg gccaaagtgc aagatgaggt gcgacaggcc    1020
atcaaaggga agaagcagag ccccatcgtc atcactgaag acgacctcaa ggggctcacc    1080
tacctcaagc aagtgatcaa ggagaccctg aggatgcaca ctccctttgcc cctcctgctt    1140 ccaaggaagt gtcgtgagac gtgcaaggtc atgggctacg acattcccaa gggcacggta    1200
gtgttcgcta acgcgtgggc aatctgcagg gatcctaagt attgggagga ttcagaggag    1260
ttcaagccag agcgattcga caagagcagt ttggactaca agggaacaaa ctttgagtac    1320
ctgccgtttg gatctggccg tcggatttgt cctggcataa atcttgggtt gggtaacgct    1380
gaaatcgcgc tagccagcct tctatatcac tttgactgga agctacctga tggaatggaa    1440
cccaaggacg taaatatgga agaggctcaa gggttagtcg ccagtaagaa aacaaactta    1500
accctgtacc ctgttactcg cattgcgccg gccggttttta attaa                    1545
```

<210> SEQ ID NO 39

```
<211> LENGTH: 43
<212> TYPE: DNA
<213> ORGANISM: Artificial sequence
<220> FEATURE:
<223> OTHER INFORMATION: Synthetic primer

<400> SEQUENCE: 39
aaggagatat acatatgaca aaaaaaagtt ggtgtcggtc agg                    43

<210> SEQ ID NO 40
<211> LENGTH: 43
<212> TYPE: DNA
<213> ORGANISM: Artificial sequence
<220> FEATURE:
<223> OTHER INFORMATION: Synthetic primer

<400> SEQUENCE: 40
ctttaccaga ctcgagttac gccttttttca tctgatcctt tgc                   43

<210> SEQ ID NO 41
<211> LENGTH: 11
<212> TYPE: PRT
<213> ORGANISM: Artificial sequence
<220> FEATURE:
<221> NAME/KEY: MOD_RES
<222> LOCATION: (4)..(4)
<223> OTHER INFORMATION: Synthetic peptide. Xaa can encompass any amino
      acid

<400> SEQUENCE: 41

Pro Phe Gly Xaa Gly Arg Arg Ile Cys Pro Gly
1               5                   10

<210> SEQ ID NO 42
<211> LENGTH: 6
<212> TYPE: PRT
<213> ORGANISM: Artificial sequence
<220> FEATURE:
<221> NAME/KEY: MOD_RES
<222> LOCATION: (2)..(2)
<223> OTHER INFORMATION: Synthetic peptide. Xaa can encompass any amino
      acid

<400> SEQUENCE: 42

Phe Xaa Pro Glu Arg Phe
1               5

<210> SEQ ID NO 43
<211> LENGTH: 7
<212> TYPE: PRT
<213> ORGANISM: Artificial sequence
<220> FEATURE:
<221> NAME/KEY: MOD_RES
<222> LOCATION: (1)..(1)
<223> OTHER INFORMATION: Synthetic peptide. Xaa can encompass either
      Alanine or Glycine

<400> SEQUENCE: 43

Xaa Gly Thr Glu Thr Ser Ser
1               5

<210> SEQ ID NO 44
<211> LENGTH: 496
<212> TYPE: PRT
<213> ORGANISM: Mentha spicata

<400> SEQUENCE: 44

Met Glu Leu Asp Leu Leu Ser Ala Ile Ile Ile Leu Val Ala Thr Tyr
```

```
1               5                   10                  15
Ile Val Ser Leu Leu Ile Asn Gln Trp Arg Lys Ser Lys Ser Gln Gln
                    20                  25                  30

Asn Leu Pro Pro Ser Pro Pro Lys Leu Pro Val Ile Gly His Leu His
                    35                  40                  45

Phe Leu Trp Gly Gly Leu Pro Gln His Val Phe Arg Ser Ile Ala Gln
            50                  55                  60

Lys Tyr Gly Pro Val Ala His Val Gln Leu Gly Glu Val Tyr Ser Val
65                  70                  75                  80

Val Leu Ser Ser Ala Glu Ala Lys Gln Ala Met Lys Val Leu Asp
                85                  90                  95

Pro Asn Phe Ala Asp Arg Phe Asp Gly Ile Gly Ser Arg Thr Met Trp
                100                 105                 110

Tyr Asp Lys Asp Asp Ile Ile Phe Ser Pro Tyr Asn Asp His Trp Arg
            115                 120                 125

Gln Met Arg Arg Ile Cys Val Thr Glu Leu Leu Ser Pro Lys Asn Val
        130                 135                 140

Arg Ser Phe Gly Tyr Ile Arg Gln Glu Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Cys Arg Ala Ala Phe Gly Ser Val
                180                 185                 190

Leu Lys Asp Gln Gly Ser Leu Ala Glu Leu Val Lys Glu Ser Leu Ala
            195                 200                 205

Leu Ala Ser Gly Phe Glu Leu Ala Asp Leu Tyr Pro Ser Ser Trp Leu
        210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255

Lys Ser Gly Glu Phe Gly Gly Glu Asp Ile Val Asp Val Leu Phe Arg
                260                 265                 270

Met Gln Lys Gly Ser Asp Ile Lys Ile Pro Ile Thr Ser Asn Cys Ile
            275                 280                 285

Lys Gly Phe Ile Phe Asp Thr Phe Ser Ala Gly Ala Glu Thr Ser Ser
        290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
                340                 345                 350

Leu Lys Glu Thr Leu Arg Leu His Pro Pro Phe Pro Leu Ile Pro Arg
            355                 360                 365

Gln Ser Arg Glu Glu Cys Glu Val Asn Gly Tyr Thr Ile Pro Ala Lys
        370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
                405                 410                 415

Arg Asp Phe Met Gly Asn Asp Phe Glu Phe Ile Pro Phe Gly Ala Gly
                420                 425                 430
```

```
Arg Arg Ile Cys Pro Gly Leu His Phe Gly Leu Ala Asn Val Glu Ile
        435                 440                 445

Pro Leu Ala Gln Leu Leu Tyr His Phe Asp Trp Lys Leu Pro Gln Gly
    450                 455                 460

Met Thr Asp Ala Asp Leu Asp Met Thr Glu Thr Pro Gly Leu Ser Gly
465                 470                 475                 480

Pro Lys Lys Lys Asn Val Cys Leu Val Pro Thr Leu Tyr Lys Ser Pro
                485                 490                 495

<210> SEQ ID NO 45
<211> LENGTH: 498
<212> TYPE: PRT
<213> ORGANISM: Mentha piperita

<400> SEQUENCE: 45

Met Glu Leu Leu Gln Leu Trp Ser Ala Leu Ile Ile Leu Val Val Thr
1               5                   10                  15

Tyr Thr Ile Ser Leu Leu Ile Asn Gln Trp Arg Lys Pro Lys Pro Gln
                20                  25                  30

Gly Lys Phe Pro Pro Gly Pro Pro Lys Leu Pro Leu Ile Gly His Leu
            35                  40                  45

His Leu Leu Trp Gly Lys Leu Pro Gln His Ala Leu Ala Ser Val Ala
        50                  55                  60

Lys Glu Tyr Gly Pro Val Ala His Val Gln Leu Gly Glu Val Phe Ser
65                  70                  75                  80

Val Val Leu Ser Ser Arg Glu Ala Thr Lys Glu Ala Met Lys Leu Val
                85                  90                  95

Asp Pro Ala Cys Ala Asn Arg Phe Glu Ser Ile Gly Thr Arg Ile Met
            100                 105                 110

Trp Tyr Asp Asn Glu Asp Ile Ile Phe Ser Pro Tyr Ser Glu His Trp
        115                 120                 125

Arg Gln Met Arg Lys Ile Cys Val Ser Glu Leu Leu Ser Ser Arg Asn
    130                 135                 140

Val Arg Ser Phe Gly Phe Ile Arg Gln Asp Glu Val Ser Arg Leu Leu
145                 150                 155                 160

Arg His Leu Arg Ser Ser Ala Gly Ala Ala Val Asp Met Thr Glu Arg
                165                 170                 175

Ile Glu Thr Leu Thr Cys Ser Ile Ile Cys Arg Ala Ala Phe Gly Ser
            180                 185                 190

Val Ile Arg Asp Asn Ala Glu Leu Val Gly Leu Val Lys Asp Ala Leu
        195                 200                 205

Ser Met Ala Ser Gly Phe Glu Leu Ala Asp Met Phe Pro Ser Ser Lys
    210                 215                 220

Leu Leu Asn Leu Leu Cys Trp Asn Lys Ser Lys Leu Trp Arg Met Arg
225                 230                 235                 240

Arg Arg Val Asp Thr Ile Leu Glu Ala Ile Val Asp Glu His Lys Phe
                245                 250                 255

Lys Lys Ser Gly Glu Phe Gly Gly Glu Asp Ile Ile Asp Val Leu Phe
            260                 265                 270

Arg Met Gln Lys Asp Thr Gln Ile Lys Val Pro Ile Thr Thr Asn Ser
        275                 280                 285

Ile Lys Ala Phe Ile Phe Asp Thr Phe Ser Ala Gly Thr Glu Thr Ser
    290                 295                 300

Ser Thr Thr Thr Leu Trp Val Leu Ala Glu Leu Met Arg Asn Pro Ala
```

```
                305                 310                 315                 320
Val Met Ala Lys Ala Gln Ala Glu Val Arg Ala Ala Leu Lys Glu Lys
                    325                 330                 335

Thr Asn Trp Asp Val Asp Val Gln Glu Leu Lys Tyr Met Lys Ser
                340                 345                 350

Val Val Lys Glu Thr Met Arg Met His Pro Pro Ile Pro Leu Ile Pro
                355                 360                 365

Arg Ser Cys Arg Glu Glu Cys Val Val Asn Gly Tyr Thr Ile Pro Asn
            370                 375                 380

Lys Ala Arg Ile Met Ile Asn Val Trp Ser Met Gly Arg Asn Pro Leu
385                 390                 395                 400

Tyr Trp Glu Lys Pro Asp Thr Phe Trp Pro Glu Arg Phe Asp Gln Val
                405                 410                 415

Ser Lys Asp Phe Met Gly Asn Asp Phe Glu Phe Val Pro Phe Gly Ala
                420                 425                 430

Gly Arg Arg Ile Cys Pro Gly Leu Asn Phe Gly Leu Ala Asn Val Glu
            435                 440                 445

Val Pro Leu Ala Gln Leu Leu Tyr His Phe Asp Trp Lys Leu Ala Glu
450                 455                 460

Gly Met Lys Pro Ser Asp Met Asp Met Ser Glu Ala Glu Gly Leu Thr
465                 470                 475                 480

Gly Ile Leu Lys Asn Asn Leu Leu Leu Val Pro Thr Pro Tyr Asp Pro
                485                 490                 495

Ser Ser

<210> SEQ ID NO 46
<211> LENGTH: 500
<212> TYPE: PRT
<213> ORGANISM: Mentha piperita

<400> SEQUENCE: 46

Met Glu Leu Gln Ile Ser Ser Ala Ile Ile Leu Val Val Thr Tyr
1               5                   10                  15

Thr Ile Ser Leu Leu Ile Ile Lys Gln Trp Arg Lys Pro Lys Pro Gln
                20                  25                  30

Glu Asn Leu Pro Pro Gly Pro Lys Leu Pro Leu Ile Gly His Leu
            35                  40                  45

His Leu Leu Trp Gly Lys Leu Pro Gln His Ala Leu Ala Ser Val Ala
        50                  55                  60

Lys Gln Tyr Gly Pro Val Ala His Val Gln Leu Gly Glu Val Phe Ser
65                  70                  75                  80

Val Val Leu Ser Ser Arg Glu Ala Thr Lys Glu Ala Met Lys Leu Val
                85                  90                  95

Asp Pro Ala Cys Ala Asp Arg Phe Glu Ser Ile Gly Thr Lys Ile Met
                100                 105                 110

Trp Tyr Asp Asn Asp Asp Ile Ile Phe Ser Pro Tyr Ser Val His Trp
            115                 120                 125

Arg Gln Met Arg Lys Ile Cys Val Ser Glu Leu Leu Ser Ala Arg Asn
        130                 135                 140

Val Arg Ser Phe Gly Phe Ile Arg Gln Asp Glu Val Ser Arg Leu Leu
145                 150                 155                 160

Gly His Leu Arg Ser Ser Ala Ala Gly Glu Ala Val Asp Leu Thr
                165                 170                 175

Glu Arg Ile Ala Thr Leu Thr Cys Ser Ile Ile Cys Arg Ala Ala Phe
```

```
            180               185               190
Gly Ser Val Ile Arg Asp His Glu Glu Leu Val Glu Leu Val Lys Asp
            195               200               205
Ala Leu Ser Met Ala Ser Gly Phe Glu Leu Ala Asp Met Phe Pro Ser
            210               215               220
Ser Lys Leu Leu Asn Leu Leu Cys Trp Asn Lys Ser Lys Leu Trp Arg
225               230               235               240
Met Arg Arg Arg Val Asp Ala Ile Leu Glu Ala Ile Val Glu His
                245               250               255
Lys Leu Lys Lys Ser Gly Glu Phe Gly Gly Glu Asp Ile Ile Asp Val
            260               265               270
Leu Phe Arg Met Gln Lys Asp Ser Gln Ile Lys Val Pro Ile Thr Thr
            275               280               285
Asn Ala Ile Lys Ala Phe Ile Phe Asp Thr Phe Ser Ala Gly Thr Glu
            290               295               300
Thr Ser Ser Thr Thr Thr Leu Trp Val Met Ala Glu Leu Met Arg Asn
305               310               315               320
Pro Glu Val Met Ala Lys Ala Gln Ala Glu Val Arg Ala Ala Leu Lys
                325               330               335
Gly Lys Thr Asp Trp Asp Val Asp Val Gln Glu Leu Lys Tyr Met
                340               345               350
Lys Ser Val Val Lys Glu Thr Met Arg Met His Pro Ile Pro Leu
            355               360               365
Ile Pro Arg Ser Cys Arg Glu Glu Cys Glu Val Asn Gly Tyr Thr Ile
            370               375               380
Pro Asn Lys Ala Arg Ile Met Ile Asn Val Trp Ser Met Gly Arg Asn
385               390               395               400
Pro Leu Tyr Trp Glu Lys Pro Glu Thr Phe Trp Pro Glu Arg Phe Asp
                405               410               415
Gln Val Ser Arg Asp Phe Met Gly Asn Asp Phe Glu Phe Ile Pro Phe
                420               425               430
Gly Ala Gly Arg Arg Ile Cys Pro Gly Leu Asn Phe Gly Leu Ala Asn
                435               440               445
Val Glu Val Pro Leu Ala Gln Leu Leu Tyr His Phe Asp Trp Lys Leu
            450               455               460
Ala Glu Gly Met Asn Pro Ser Asp Met Asp Met Ser Glu Ala Glu Gly
465               470               475               480
Leu Thr Gly Ile Arg Lys Asn Asn Leu Leu Val Pro Thr Pro Tyr
                485               490               495
Asp Pro Ser Ser
            500

<210> SEQ ID NO 47
<211> LENGTH: 473
<212> TYPE: PRT
<213> ORGANISM: Nicotiana tabacum

<400> SEQUENCE: 47

Met Glu Phe Phe Ser Leu Val Ser Ile Phe Leu Phe Ser Phe Leu
1               5               10              15
Phe Leu Leu Arg Lys Cys Lys Asn Ser Asn Ser Gln Thr Lys Gln Leu
                20              25              30
Pro Pro Gly Pro Trp Lys Ile Pro Ile Leu Gly Ser Met Leu His Met
            35              40              45
```

```
Leu Gly Gly Glu Pro His His Ile Leu Arg Asp Leu Ala Lys Lys Tyr
 50                  55                  60

Gly Pro Ile Met His Leu Gln Phe Gly Glu Ile Ser Ala Val Val
 65                  70                  75                  80

Thr Ser Arg Glu Met Ala Lys Glu Val Leu Lys Thr His Asp Val Val
                 85                  90                  95

Phe Ala Ser Arg Pro Lys Ile Val Ala Met Asp Ile Ile Cys Tyr Asn
                100                 105                 110

Gln Ser Asp Ile Ala Phe Ser Pro Tyr Gly Asp His Trp Arg Gln Met
            115                 120                 125

Arg Lys Ile Cys Val Met Glu Leu Leu Asn Ala Lys Asn Val Arg Ser
130                 135                 140

Phe Ser Ser Ile Arg Arg Asp Glu Val Val Arg Leu Ile Asp Ser Ile
145                 150                 155                 160

Arg Ser Asp Ser Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
            180                 185                 190

Leu Lys Gly Gln Asp Val Phe Ala Lys Lys Ile Arg Glu Val Ile Gly
            195                 200                 205

Leu Ala Glu Gly Phe Asp Val Ala Asp Ile Phe Pro Ser Tyr Lys Phe
210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
                245                 250                 255

Leu Ala Thr Gly Lys Thr Asn Gly Ala Leu Gly Asp Met Phe Ala Ala
            260                 265                 270

Gly Thr Glu Thr Ser Ser Thr Thr Val Trp Ala Met Ala Glu Met
            275                 280                 285

Met Lys Asn Pro Asn Val Phe Asn Lys Ala Gln Ala Glu Val Arg Glu
290                 295                 300

Thr Phe Lys Asp Lys Val Thr Phe Asp Glu Ile Asp Ala Glu Glu Leu
305                 310                 315                 320

Glu Tyr Leu Lys Leu Val Ile Lys Glu Thr Leu Arg Leu His Pro Pro
                325                 330                 335

Ser Pro Leu Leu Val Pro Arg Glu Cys Arg Glu Asp Thr Asp Ile Asn
            340                 345                 350

Gly Tyr Thr Ile Pro Ala Lys Thr Lys Val Met Val Asn Val Trp Ala
            355                 360                 365

Leu Gly Arg Asp Pro Lys Tyr Trp Asp Asp Ala Glu Ser Phe Lys Pro
370                 375                 380

Glu Arg Phe Glu Gln Cys Ser Val Asp Phe Phe Gly Asn Asn Phe Glu
385                 390                 395                 400

Phe Leu Pro Phe Gly Gly Gly Arg Arg Ile Cys Pro Gly Met Ser Phe
                405                 410                 415

Gly Leu Ala Asn Leu Tyr Leu Pro Leu Ala Gln Leu Leu Tyr His Phe
            420                 425                 430

Asp Trp Lys Leu Pro Ser Gly Met Met Pro Gly Asp Leu Asp Leu Thr
            435                 440                 445

Glu Leu Ala Gly Ile Thr Ile Ala Arg Lys Gly Asp Leu Tyr Leu Met
450                 455                 460

Ala Thr Pro Tyr Gln Pro Ser Arg Glu
```

-continued 465 470

<210> SEQ ID NO 48
<211> LENGTH: 502
<212> TYPE: PRT
<213> ORGANISM: Hyoscyamus muticus

<400> SEQUENCE: 48

Met Gln Phe Phe Ser Leu Val Ser Ile Phe Leu Phe Leu Ser Phe Leu
1               5                   10                  15

Phe Leu Leu Arg Lys Trp Lys Asn Ser Asn Ser Gln Ser Lys Lys Leu
            20                  25                  30

Pro Pro Gly Pro Trp Lys Leu Pro Leu Leu Gly Ser Met Leu His Met
        35                  40                  45

Val Gly Gly Leu Pro His His Val Leu Arg Asp Leu Ala Lys Lys Tyr
50                  55                  60

Gly Pro Leu Met His Leu Gln Leu Gly Glu Val Ser Ala Val Val Val
65                  70                  75                  80

Thr Ser Pro Asp Met Ala Lys Glu Val Leu Lys Thr His Asp Ile Ala
                85                  90                  95

Phe Ala Ser Arg Pro Lys Leu Leu Ala Pro Glu Ile Val Cys Tyr Asn
            100                 105                 110

Arg Ser Asp Ile Ala Phe Cys Pro Tyr Gly Asp Tyr Trp Arg Gln Met
        115                 120                 125

Arg Lys Ile Cys Val Leu Glu Val Leu Ser Ala Lys Asn Val Arg Ser
130                 135                 140

Phe Ser Ser Ile Arg Arg Asp Glu Val Leu Arg Leu Val Asn Phe Val
145                 150                 155                 160

Arg Ser Ser Thr Ser Glu Pro Val Asn Phe Thr Glu Arg Leu Phe Leu
                165                 170                 175

Phe Thr Ser Ser Met Thr Cys Arg Ser Ala Phe Gly Lys Val Phe Lys
            180                 185                 190

Glu Gln Glu Thr Phe Ile Gln Leu Ile Lys Glu Val Ile Gly Leu Ala
        195                 200                 205

Gly Gly Phe Asp Val Ala Asp Ile Phe Pro Ser Leu Lys Phe Leu His
210                 215                 220

Val Leu Thr Gly Met Glu Gly Lys Ile Met Lys Ala His His Lys Val
225                 230                 235                 240

Asp Ala Ile Val Glu Asp Val Ile Asn Glu His Lys Lys Asn Leu Ala
                245                 250                 255

Met Gly Lys Thr Asn Gly Ala Leu Gly Glu Asp Leu Ile Asp Val
            260                 265                 270

Leu Leu Arg Leu Met Asn Asp Gly Gly Leu Gln Phe Pro Ile Thr Asn
        275                 280                 285

Asp Asn Ile Lys Ala Ile Ile Phe Asp Met Phe Ala Ala Gly Thr Glu
290                 295                 300

Thr Ser Ser Ser Thr Leu Val Trp Ala Met Val Gln Met Met Arg Asn
305                 310                 315                 320

Pro Thr Ile Leu Ala Lys Ala Gln Ala Glu Val Arg Glu Ala Phe Lys
                325                 330                 335

Gly Lys Glu Thr Phe Asp Glu Asn Asp Val Glu Glu Leu Lys Tyr Leu
            340                 345                 350

Lys Leu Val Ile Lys Glu Thr Leu Arg Leu His Pro Pro Val Pro Leu
        355                 360                 365

Leu Val Pro Arg Glu Cys Arg Glu Thr Glu Ile Asn Gly Tyr Thr
    370             375             380

Ile Pro Val Lys Thr Lys Val Met Val Asn Val Trp Ala Leu Gly Arg
385             390             395                 400

Asp Pro Lys Tyr Trp Asp Asp Ala Asp Asn Phe Lys Pro Glu Arg Phe
                405             410             415

Glu Gln Cys Ser Val Asp Phe Ile Gly Asn Asn Phe Glu Tyr Leu Pro
            420             425             430

Phe Gly Gly Gly Arg Arg Ile Cys Pro Gly Ile Ser Phe Gly Leu Ala
        435             440             445

Asn Val Tyr Leu Pro Leu Ala Gln Leu Leu Tyr His Phe Asp Trp Lys
450             455             460

Leu Pro Thr Gly Met Glu Pro Lys Asp Leu Asp Leu Thr Glu Leu Val
465             470             475             480

Gly Val Thr Ala Ala Arg Lys Ser Asp Leu Met Leu Val Ala Thr Pro
                485             490             495

Tyr Gln Pro Ser Arg Glu
            500

<210> SEQ ID NO 49
<211> LENGTH: 497
<212> TYPE: PRT
<213> ORGANISM: Mentha gracilis

<400> SEQUENCE: 49

Met Glu Leu Gln Ile Ser Ser Ala Ile Ile Leu Val Ala Thr Phe
1               5               10              15

Val Ala Ser Leu Leu Ile Lys Gln Trp Arg Lys Ser Glu Ser Gln Gln
                20              25              30

Asn Leu Pro Pro Gly Pro Lys Leu Pro Leu Val Gly His Leu His
            35              40              45

Leu Leu Trp Gly Lys Leu Pro Gln His Ala Met Ala Asp Met Ala Lys
        50              55              60

Lys Tyr Gly Pro Val Thr His Val Gln Leu Gly Glu Val Phe Ser Val
65              70              75              80

Val Leu Ser Ser Arg Glu Ala Thr Lys Glu Ala Met Lys Leu Leu Asp
                85              90              95

Pro Ala Cys Ala Asp Arg Phe Glu Ser Ile Gly Thr Arg Ile Met Trp
            100             105             110

Tyr Asp Asn Asp Asp Ile Ile Phe Ser Pro Tyr Ser Asp His Trp Arg
        115             120             125

Gln Met Arg Lys Ile Cys Val Ser Glu Leu Leu Ser Ala Arg Asn Val
130             135             140

Arg Ser Phe Gly Phe Ile Arg Gln Asp Glu Met Ser Arg Leu Leu Arg
145             150             155             160

His Leu Gln Ser Ser Ala Gly Glu Thr Val Asp Met Thr Glu Arg Ile
                165             170             175

Ala Thr Leu Thr Cys Ser Ile Ile Cys Arg Ala Ala Phe Gly Ala Ile
            180             185             190

Ile Asn Asp His Glu Glu Leu Val Glu Leu Val Lys Asp Ser Leu Ser
        195             200             205

Met Ala Ser Gly Phe Glu Leu Ala Asp Leu Phe Pro Ser Ser Lys Leu
210             215             220

Leu Asn Leu Leu Cys Trp Asn Lys Ser Lys Leu Trp Arg Met Arg Arg
225             230             235             240

Arg Val Asp Thr Ile Leu Glu Ala Ile Val Glu His Lys Leu Lys
                245                 250                 255

Lys Ser Gly Glu Phe Gly Gly Glu Asp Ile Ile Asp Val Leu Phe Arg
        260                 265                 270

Met Gln Lys Asp Ser Gln Ile Lys Val Pro Ile Thr Thr Asn Ala Ile
            275                 280                 285

Lys Ala Phe Ile Phe Asp Thr Phe Ser Ala Gly Thr Glu Thr Ser Ser
290                 295                 300

Thr Thr Thr Leu Trp Val Met Ala Glu Leu Met Arg Asn Pro Ala Val
305                 310                 315                 320

Met Ala Lys Ala Gln Ala Glu Val Arg Ala Ala Leu Lys Gly Lys Thr
                325                 330                 335

Ser Val Asp Val Asp Asp Val Gln Glu Leu Lys Tyr Met Lys Ser Val
            340                 345                 350

Val Lys Glu Thr Met Arg Met His Pro Pro Ile Pro Leu Ile Pro Arg
        355                 360                 365

Ser Cys Arg Glu Glu Cys Glu Val Asn Gly Tyr Lys Ile Pro Asn Lys
    370                 375                 380

Ala Arg Ile Met Ile Asn Val Trp Ser Met Gly Arg Asn Pro Leu Tyr
385                 390                 395                 400

Trp Glu Lys Pro Glu Thr Phe Trp Pro Glu Arg Phe Asp Gln Val Ser
                405                 410                 415

Arg Asp Phe Met Gly Ser Asp Phe Glu Phe Ile Pro Phe Gly Ala Gly
            420                 425                 430

Arg Arg Ile Cys Pro Gly Leu Asn Phe Gly Leu Ala Asn Val Glu Val
        435                 440                 445

Pro Leu Ala Gln Leu Leu Tyr His Phe Asp Trp Lys Leu Ala Glu Gly
    450                 455                 460

Met Lys Pro Ser Asp Met Asp Met Ser Glu Ala Glu Gly Leu Thr Gly
465                 470                 475                 480

Ile Arg Lys Asn Asn Leu Leu Val Pro Thr Pro Tyr Asn Pro Ser
                485                 490                 495

Ser

<210> SEQ ID NO 50
<211> LENGTH: 496
<212> TYPE: PRT
<213> ORGANISM: Mentha gracilis

<400> SEQUENCE: 50

Met Glu Leu Asp Leu Leu Ser Ala Ile Ile Ile Leu Val Ala Thr Tyr
1               5                   10                  15

Ile Val Ser Leu Leu Ile Asn Gln Trp Arg Lys Ser Lys Ser Gln Gln
            20                  25                  30

Asn Leu Pro Pro Ser Pro Pro Lys Leu Pro Val Ile Gly His Leu His
        35                  40                  45

Phe Leu Trp Gly Gly Leu Pro Gln His Val Phe Arg Ser Ile Ala Gln
    50                  55                  60

Lys Tyr Gly Pro Val Ala His Val Gln Leu Gly Glu Val Tyr Ser Val
65                  70                  75                  80

Val Leu Ser Ser Ala Glu Ala Ala Lys Gln Ala Met Lys Val Leu Asp
                85                  90                  95

Pro Asn Phe Ala Asp Arg Phe Asp Gly Ile Gly Ser Arg Thr Met Trp
            100                 105                 110

Tyr Asp Lys Asp Asp Ile Ile Phe Ser Pro Tyr Asn Asp His Trp Arg
            115                 120                 125

Gln Met Arg Arg Ile Cys Val Thr Glu Leu Leu Ser Pro Lys Asn Val
        130                 135                 140

Arg Ser Phe Gly Tyr Ile Arg Gln Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Cys Arg Ala Ala Phe Gly Ser Val
            180                 185                 190

Leu Lys Asp Gln Gly Ser Leu Ala Glu Leu Val Lys Glu Ser Leu Ala
            195                 200                 205

Leu Ala Ser Gly Phe Glu Leu Ala Asp Leu Tyr Pro Ser Ser Trp Leu
            210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255

Lys Ser Gly Glu Phe Gly Gly Asp Ile Val Asp Val Leu Phe Arg
            260                 265                 270

Met Gln Lys Gly Ser Asp Ile Lys Ile Pro Ile Thr Ser Asn Cys Ile
            275                 280                 285

Lys Gly Phe Ile Phe Asp Thr Phe Ser Ala Gly Ala Glu Thr Ser Ser
            290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
            340                 345                 350

Leu Lys Glu Thr Leu Arg Leu His Pro Pro Phe Pro Leu Ile Pro Arg
            355                 360                 365

Gln Ser Arg Glu Glu Cys Glu Val Asn Gly Tyr Thr Ile Pro Ala Lys
            370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
                405                 410                 415

Arg Asp Phe Met Gly Asn Asp Phe Glu Phe Ile Pro Phe Gly Ala Gly
            420                 425                 430

Arg Arg Ile Cys Pro Gly Leu His Phe Gly Leu Ala Asn Val Glu Ile
            435                 440                 445

Pro Leu Ala Gln Leu Leu Tyr His Phe Asp Trp Lys Leu Pro Gln Gly
450                 455                 460

Met Thr Asp Ala Asp Leu Asp Met Thr Glu Thr Pro Gly Leu Ser Gly
465                 470                 475                 480

Pro Lys Lys Lys Asn Val Cys Leu Val Pro Thr Leu Tyr Lys Ser Pro
                485                 490                 495

<210> SEQ ID NO 51
<211> LENGTH: 499
<212> TYPE: PRT
<213> ORGANISM: Nicotiana tabacum

<400> SEQUENCE: 51

```
Met Gln Phe Phe Asn Phe Phe Ser Leu Phe Leu Phe Val Ser Phe Leu
1               5                   10                  15

Phe Leu Phe Lys Lys Trp Lys Asn Ser Asn Ser Gln Thr Lys Arg Leu
            20                  25                  30

Pro Pro Gly Pro Trp Lys Leu Pro Ile Leu Gly Ser Met Leu His Met
        35                  40                  45

Leu Gly Gly Leu Pro His His Val Leu Arg Asp Leu Ala Lys Lys Tyr
    50                  55                  60

Gly Pro Ile Met His Leu Gln Leu Gly Glu Val Ser Leu Val Val Ile
65                  70                  75                  80

Ser Ser Pro Gly Met Ala Lys Glu Val Leu Lys Thr His Asp Leu Ala
                85                  90                  95

Phe Ala Asn Arg Pro Leu Leu Val Ala Ala Lys Ile Phe Ser Tyr Asn
            100                 105                 110

Cys Met Asp Ile Ala Leu Ser Pro Tyr Gly Asn Tyr Trp Arg Gln Met
        115                 120                 125

Arg Lys Ile Cys Leu Leu Glu Leu Leu Ser Ala Lys Asn Val Lys Ser
    130                 135                 140

Phe Asn Ser Ile Arg Gln Asp Glu Val His Arg Met Ile Lys Phe Phe
145                 150                 155                 160

Arg Ser Ser Pro Gly Lys Pro Val Asn Val Thr Lys Arg Ile Ser Leu
                165                 170                 175

Phe Thr Asn Ser Met Thr Cys Arg Ser Ala Phe Gly Gln Glu Tyr Lys
            180                 185                 190

Glu Gln Asp Glu Phe Val Gln Leu Val Lys Lys Val Ser Asn Leu Ile
        195                 200                 205

Glu Gly Phe Asp Val Ala Asp Ile Phe Pro Ser Leu Lys Phe Leu His
    210                 215                 220

Val Leu Thr Gly Met Lys Ala Lys Val Met Asn Thr His Asn Glu Leu
225                 230                 235                 240

Asp Ala Ile Leu Glu Asn Ile Ile Asn Glu His Lys Lys Thr Ser Lys
                245                 250                 255

Ser Asp Gly Glu Ser Gly Gly Glu Gly Ile Ile Gly Val Leu Leu Arg
            260                 265                 270

Leu Met Lys Glu Gly Gly Leu Gln Phe Pro Ile Thr Asn Asp Asn Ile
        275                 280                 285

Lys Ala Ile Ile Ser Asp Ile Phe Gly Gly Gly Thr Glu Thr Ser Ser
    290                 295                 300

Thr Thr Ile Asn Trp Ala Met Val Glu Met Met Lys Asn Pro Ser Val
305                 310                 315                 320

Phe Ser Lys Ala Gln Ala Glu Val Arg Glu Ile Leu Arg Gly Lys Glu
                325                 330                 335

Thr Phe Gly Glu Ile Asp Val Glu Glu Phe Lys Tyr Leu Lys Met Val
            340                 345                 350

Ile Lys Glu Thr Phe Arg Leu His Pro Pro Leu Pro Leu Leu Leu Pro
        355                 360                 365

Arg Glu Cys Arg Glu Glu Ile Asp Leu Asn Gly Tyr Thr Ile Pro Leu
    370                 375                 380

Lys Thr Lys Val Val Val Asn Ala Trp Ala Met Gly Arg Asp Pro Lys
385                 390                 395                 400

Tyr Trp Asp Asp Val Glu Ser Phe Lys Pro Glu Arg Phe Glu His Asn
                405                 410                 415
```

```
Ser Met Asp Tyr Ile Gly Asn Asn Tyr Glu Tyr Leu Pro Phe Gly Ser
        420                 425                 430

Gly Arg Arg Ile Cys Pro Gly Ile Ser Phe Gly Leu Ala Asn Val Tyr
        435                 440                 445

Phe Pro Leu Ala Gln Leu Leu Asn His Phe Asp Trp Lys Leu Pro Thr
450                 455                 460

Gly Ile Asn Pro Arg Asn Cys Asp Leu Thr Glu Ala Ala Gly Ala Ala
465                 470                 475                 480

Cys Ala Arg Lys Asn Asp Leu His Leu Ile Ala Thr Ala Tyr Gln His
                485                 490                 495

Cys Glu Glu

<210> SEQ ID NO 52
<211> LENGTH: 502
<212> TYPE: PRT
<213> ORGANISM: Solanum tuberosum

<400> SEQUENCE: 52

Met Gln Phe Leu Ser Leu Ala Ser Ile Phe Leu Phe Leu Ser Phe Leu
1               5                   10                  15

Phe Leu Leu Arg Lys Trp Lys Asn Ser Asn Ser Gln Ser Lys Lys Leu
            20                  25                  30

Pro Pro Gly Pro Trp Lys Leu Pro Leu Leu Gly Ser Met Leu His Met
        35                  40                  45

Ala Gly Gly Leu Pro His His Val Leu Arg Asp Leu Ala Lys Lys Tyr
    50                  55                  60

Gly Pro Leu Met His Leu Gln Leu Gly Glu Val Ser Ala Val Val Val
65                  70                  75                  80

Thr Ser Pro Asp Met Ala Lys Glu Val Leu Lys Thr His Asp Ile Ala
                85                  90                  95

Phe Ala Ser Arg Pro Lys Leu Leu Ala Pro Glu Ile Val Cys Tyr Asn
            100                 105                 110

Arg Ser Asp Ile Ala Phe Cys Pro Tyr Gly Asp Tyr Trp Arg Gln Met
        115                 120                 125

Arg Lys Ile Cys Val Leu Glu Leu Leu Ser Ala Lys Asn Val Arg Ser
    130                 135                 140

Tyr Gly Ser Ile Arg Arg Asp Glu Val Asp Arg Leu Val Asn Phe Ile
145                 150                 155                 160

Arg Ser Ser Ser Gly Glu Pro Val Asn Phe Thr Glu Arg Leu Phe Leu
                165                 170                 175

Phe Thr Ser Ser Met Thr Cys Arg Ser Ala Phe Gly Lys Val Phe Lys
            180                 185                 190

Glu Gln Asp Lys Phe Ile Gln Leu Ile Lys Glu Val Ile Gly Leu Ala
        195                 200                 205

Gly Gly Phe Asp Val Ala Asp Ile Phe Pro Ser Leu Lys Phe Leu His
    210                 215                 220

Val Leu Ser Gly Met Lys Gly Lys Ile Met Asn Ala His His Lys Val
225                 230                 235                 240

Asp Ala Ile Val Glu Asp Val Ile Asn Glu His Lys Lys Lys Phe Ala
                245                 250                 255

Ile Gly Lys Thr Asn Gly Ala Leu Gly Gly Glu Asp Leu Ile Asp Val
            260                 265                 270

Leu Ile Arg Leu Met Asn Asp Gly Gly Leu Gln Phe Pro Ile Thr Asn
        275                 280                 285
```

```
Asp Asn Ile Lys Ala Ile Ile Phe Asp Met Phe Ala Ala Gly Thr Glu
    290                 295                 300

Thr Ser Ser Ser Thr Leu Val Trp Ala Met Val Gln Met Met Lys Asn
305                 310                 315                 320

Pro Ser Val Ile Ala Lys Ala Gln Ala Glu Val Arg Glu Ala Phe Lys
                325                 330                 335

Asp Lys Glu Thr Phe Asp Glu Asn Asp Val Glu Glu Leu Lys Tyr Leu
            340                 345                 350

Lys Leu Val Ile Lys Glu Thr Leu Arg Leu His Pro Pro Val Pro Leu
        355                 360                 365

Leu Val Pro Arg Glu Cys Arg Glu Glu Thr Asp Ile Asn Gly Tyr Thr
    370                 375                 380

Ile Pro Val Lys Thr Lys Val Met Val Asn Val Trp Ala Leu Gly Arg
385                 390                 395                 400

Asp Pro Lys Tyr Trp Asp Asp Ala Glu Ser Phe Lys Pro Glu Arg Phe
                405                 410                 415

Glu Gln Arg Ser Val Asp Phe Val Gly Asn Asn Phe Glu Tyr Leu Pro
            420                 425                 430

Phe Gly Gly Gly Arg Arg Ile Cys Pro Gly Ile Ser Phe Gly Leu Ala
        435                 440                 445

Asn Val Tyr Leu Pro Leu Ala His Leu Leu Tyr His Phe Asp Trp Lys
    450                 455                 460

Leu Pro Ile Gly Met Glu Pro Lys Asp Leu Asn Leu Thr Glu Leu Val
465                 470                 475                 480

Gly Val Thr Ala Ala Arg Lys Asp Asp Leu Ile Leu Val Ala Thr Pro
                485                 490                 495

Tyr Glu Pro Pro Arg Gln
            500

<210> SEQ ID NO 53
<211> LENGTH: 501
<212> TYPE: PRT
<213> ORGANISM: Solanum chacoense

<400> SEQUENCE: 53

Met Gln Leu Ile Ser Ile Phe Leu Phe Ile Cys Phe Leu Phe Leu Leu
1               5                   10                  15

Arg Lys Trp Lys Lys Tyr Ser Lys Asn Ser Gln Thr Lys Lys Leu Pro
            20                  25                  30

Pro Gly Pro Trp Lys Leu Pro Phe Ile Gly Ser Met His His Leu Ala
        35                  40                  45

Gly Gly Arg Pro His Arg Val Leu Arg Asp Leu Ala Lys Lys Tyr Gly
    50                  55                  60

Pro Leu Met His Leu Gln Leu Gly Glu Val Ser Ala Val Val Val Thr
65                  70                  75                  80

Ser Pro Asp Met Ala Lys Glu Val Leu Lys Thr His Asp Ile Ala Phe
                85                  90                  95

Ala Ser Arg Pro Lys Leu Leu Ala Met Asp Ile Ile Cys Tyr Asp Arg
            100                 105                 110

Cys Asp Ile Ala Phe Ser Pro Tyr Gly Glu Tyr Trp Lys Gln Met Arg
        115                 120                 125

Lys Ile Cys Val Thr Glu Val Leu Ser Ala Lys Ser Val Arg Ser Phe
    130                 135                 140

Ser Ser Ile Arg Cys Asp Glu Val Val Arg Leu Ile Asp Ser Ile Gln
```

```
                145                 150                 155                 160
        Ser Ser Ser Ser Gly Glu Leu Val Asn Phe Lys Glu Arg Val Ile
                        165                 170                 175

Trp Phe Thr Ser Ser Met Thr Cys Arg Ser Ala Phe Gly Gln Leu Pro
                        180                 185                 190

Lys Glu Gln Asp Met Phe Ile Lys Leu Ile Arg Glu Val Ile Arg Leu
                        195                 200                 205

Ala Glu Gly Phe Asp Val Ala Asp Ile Phe Pro Ser Tyr Lys Phe Leu
                210                 215                 220

His Val Phe Gly Arg Ala Lys Arg Lys Leu Leu Asn Val His Arg Lys
        225                 230                 235                 240

Val Asp Ala Ile Val Glu Asp Val Ile Asn Glu His Lys Lys Asn Phe
                        245                 250                 255

Ala Thr Arg Lys Asn Asp Asp His Ala Leu Gly Gly Glu Asn Leu Ile
                        260                 265                 270

Asp Val Leu Leu Lys Leu Met Asn Asp Lys Ser Leu Gln Phe Pro Ile
                        275                 280                 285

Asn Asn Asp Asn Ile Lys Ala Ile Ile Ile Asp Met Phe Ala Ala Gly
                        290                 295                 300

Thr Glu Thr Ser Ser Thr Thr Thr Val Trp Ala Met Val Glu Met Leu
        305                 310                 315                 320

Lys Asn Pro Arg Val Leu Ala Lys Ala Gln Ala Glu Val Arg Glu Ala
                        325                 330                 335

Phe Arg Asn Lys Val Thr Phe Asp Glu Asn Asp Val Glu Asp Leu Lys
                        340                 345                 350

Tyr Leu Lys Leu Val Ile Lys Glu Thr Met Arg Leu His Ala Pro Ile
                        355                 360                 365

Pro Leu Leu Val Pro Arg Glu Cys Arg Lys Glu Thr Glu Ile Asn Gly
                370                 375                 380

Tyr Thr Ile Pro Val Lys Thr Lys Val Met Val Asn Val Trp Ala Leu
        385                 390                 395                 400

Gly Arg Asp Pro Lys Tyr Trp Asp Asp Val Glu Cys Phe Lys Pro Glu
                        405                 410                 415

Arg Phe Glu Gln Cys Ser Ile Asp Phe Ile Gly Asn Asn Phe Glu Tyr
                        420                 425                 430

Leu Pro Phe Gly Gly Gly Arg Arg Ile Cys Pro Gly Thr Ser Phe Gly
                        435                 440                 445

Leu Ala Asn Asp Tyr Leu Pro Leu Ala Gln Leu Leu Cys His Phe Asp
                450                 455                 460

Trp Lys Leu Pro Thr Gly Met Glu Pro Lys Asp Leu Asp Leu Thr Glu
        465                 470                 475                 480

Leu Ala Gly Met Ser Ala Ala Ser Lys Asp Asp Leu Tyr Leu Ile Ala
                        485                 490                 495

Thr Pro Tyr Gln Pro
                    500

<210> SEQ ID NO 54
<211> LENGTH: 85
<212> TYPE: DNA
<213> ORGANISM: Artificial sequence
<220> FEATURE:
<223> OTHER INFORMATION: Synthetic cDNA vetiver P450 and Cytochrome
      P450-reductase

<400> SEQUENCE: 54
```

```
cattgcgccg gccggtttta attaagctgt cgactaactt taagaaggag atatatccat    60
gggcacggat agcctgagcg acgac                                          85
```

<210> SEQ ID NO 55
<211> LENGTH: 10
<212> TYPE: PRT
<213> ORGANISM: Artificial Sequence
<220> FEATURE:
<223> OTHER INFORMATION: Synthetic peptide

<400> SEQUENCE: 55

```
Gly Pro Val Met His Val Gln Leu Gly Glu
1               5                   10
```

<210> SEQ ID NO 56
<211> LENGTH: 10
<212> TYPE: PRT
<213> ORGANISM: Artificial Sequence
<220> FEATURE:
<223> OTHER INFORMATION: Synthetic peptide

<400> SEQUENCE: 56

```
Pro Tyr Gly Asp His Trp Arg Gln Met Arg
1               5                   10
```

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

```
Ser Met Thr Cys Arg Ala Ala Phe Gly
1               5
```

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

```
Val Ile Lys Glu Thr Met Arg Met His
1               5
```

<210> SEQ ID NO 59
<211> LENGTH: 8
<212> TYPE: PRT
<213> ORGANISM: Artificial Sequence
<220> FEATURE:
<223> OTHER INFORMATION: Synthetic peptide

<400> SEQUENCE: 59

```
Glu Thr Met Arg Met His Pro Pro
1               5
```

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

```
Phe Gly Leu Ala Asn Val Tyr Leu Pro
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

His Phe Asp Trp Lys Leu Pro Thr Gly
1               5
```

What is claimed is:

1. An expression vector comprising
a nucleic acid encoding a polypeptide comprising an amino acid sequence having at least 90% sequence identity to SEQ ID NO: 1 or SEQ ID NO: 2 and having a cytochrome P450 activity characterized in that the polypeptide is capable of oxidizing at least one terpene compound selected from mono- or polycyclic monoterpenes and sesquiterpenes;
wherein the expression vector further comprises a heterologous nucleic acid comprising at least one regulatory sequence that controls transcription.

2. A non-human host organism or cell
a. transformed to harbor at least one nucleic acid encoding a polypeptide comprising an amino acid sequence having at least 90% sequence identity to SEQ ID NO: 1 or SEQ ID NO: 2 and having a cytochrome P450 activity characterized in that the polypeptide is capable of oxidizing at least one terpene compound selected from mono- or polycyclic monoterpenes and sesquiterpenes; or
b. comprising the expression vector of claim 1.

3. The non-human host organism of claim 2, wherein said non-human host organism is a plant, a prokaryote or a fungus.

4. The non-human host organism of claim 2, wherein said non-human host organism is a microorganism.

5. The non-human host organism of claim 4, wherein said microorganism is a bacteria or yeast.

6. The non-human host organism of claim 5, wherein said bacteria is E. coli and said yeast is Saccharomyces cerevisiae.

7. The non human host cell of claim 2, which is a plant cell.

8. A method for oxidizing at least one terpene compound comprising: a) contacting at least one terpene compound with at least one polypeptide comprising an amino acid sequence having at least 90% sequence identity to SEQ ID NO: 1 or SEQ ID NO: 2 and having a cytochrome P450 activity to produce an oxidized terpene; and b) optionally, isolating the oxidized terpene produced in step a);
wherein the at least one polypeptide comprises a polypeptide that is
i) produced by the non-human host organism or cell of claim 2;
ii) in a cell lysate of the non-human host organism or cell;
iii) in a culture medium used for culturing the non-human host organism or cell; and/or
iv) isolated from the non-human host organism or cell, cell lysate and/or culture medium.

9. The method of claim 8, wherein said terpene compound is selected from mono- or polycyclic monoterpenes and sesquiterpenes.

10. The method of claim 9, wherein said terpene compound is selected from the group consisting of zizaene, alpha-cedrene, alpha-longipinene, alpha-funebrene, thujopsene, valencene, beta-chamigrene, alloaromadendrene, alpha-neoclovene, isosativene, ledene, S-limonene, alpha-humulene, alpha gurjunene, alpha-pinene, beta-funebrene, R-limonene and beta-pinene.

11. The method of claim 10, characterized in that the terpene compound is selected from the group consisting of zizaene, alpha-cedrene, alpha-funebrene, valencene, and thujopsene.

12. The method of claim 10, wherein the terpene compound is further oxidized to a primary alcohol, an aldehyde, and/or a carboxylic acid.

13. The method of claim 11, wherein zizaene is further oxidized to khusimol, zizanal, and/or zizanoic acid.

14. The expression vector of claim 1, wherein the nucleic acid comprises the nucleotide sequence of SEQ ID NO: 3, SEQ ID NO: 4 or the complement thereof.

15. An expression vector comprising
a nucleic acid encoding a polypeptide comprising an amino acid sequence having at least 90% sequence identity to SEQ ID NO: 1 or SEQ ID NO: 2 and having a cytochrome P450 activity characterized in that the polypeptide is capable of oxidizing at least one terpene compound selected from mono- or polycyclic monoterpenes and sesquiterpenes;
wherein the expression vector is in the form of a viral vector, a bactriophage or a plasmid.

16. The expression vector of claim 1, wherein the nucleic acid is operably linked to at least one regulatory sequence.

17. The non-human host organism or cell of claim 2, wherein the nucleic acid comprises the nucleotide sequence of SEQ ID NO: 3, SEQ ID NO: 4 or the complement thereof.

18. A method for oxidizing at least one terpene compound comprising:
a) cultivating the non-human organism or cell of claim 2 in the presence of at least one terpene compound to be oxidized under conditions conducive to oxidation of the at least one terpene compound; and
b) optionally, isolating the oxidized terpene produced in step a).

19. The method of claim of claim 18, further comprising, prior to step a), transforming a non-human host organism or cell with at least one nucleic acid encoding the at least polypeptide having cytochrome P450 activity, so that said organism or cell expresses the at least one polypeptide.

20. The method of claim 18, wherein the non-human host organism or cell is a bacteria or yeast.

21. The method of claim 20, wherein the bacteria is *E. coli* and the yeast is *Saccharomyces cerevisiae*.

22. The method of claim 18, wherein the terpene compound is selected from the group consisting of zizaene, alpha-cedrene, alpha-longipinene, alpha-funebrene, thujopsene, valencene, beta-chamigrene, alloaromadendrene, alpha-neoclovene, isosativene, ledene, S-limonene, alpha-humulene, alpha gurjunene, alpha-pinene, beta-funebrene, R-limonene and beta-pinene.

23. The method of claim 22, wherein zizaene is further oxidized to khusimol, zizanal, and/or zizanoic acid.

* * * * *